United States Patent
Benton et al.

(10) Patent No.: US 12,409,184 B2
(45) Date of Patent: *Sep. 9, 2025

(54) ILOPROST COMPOSITIONS AND FORMULATIONS THEREOF

(71) Applicant: BTG INTERNATIONAL INC., West Conshohocken, PA (US)

(72) Inventors: Wade W. Benton, Emerald Hills, CA (US); Kevin A. Christal, Burlingame, CA (US)

(73) Assignee: BTG INTERNATIONAL INC., West Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/018,702

(22) Filed: Jan. 13, 2025

(65) Prior Publication Data

US 2025/0144117 A1    May 8, 2025

Related U.S. Application Data

(63) Continuation of application No. 18/260,778, filed as application No. PCT/US2021/045013 on Aug. 6, 2021.

(60) Provisional application No. 63/062,812, filed on Aug. 7, 2020.

(51) Int. Cl.
*A61K 31/5578* (2006.01)
*A61P 19/04* (2006.01)

(52) U.S. Cl.
CPC .......... *A61K 31/5578* (2013.01); *A61P 19/04* (2018.01)

(58) Field of Classification Search
CPC ............................ A61K 31/5578; A61P 19/00
See application file for complete search history.

(56) References Cited

U.S. PATENT DOCUMENTS

| | | |
|---|---|---|
| 5,523,321 A | 6/1996 | Stuerzebecher et al. |
| 9,517,202 B2 | 12/2016 | Chen et al. |
| 2006/0147520 A1 | 7/2006 | Ruegg |
| 2006/0276546 A1 | 12/2006 | Keith et al. |
| 2009/0215769 A1 | 8/2009 | Krahn et al. |
| 2012/0321579 A1 | 12/2012 | Edelson et al. |
| 2013/0040898 A1 | 2/2013 | Johansson |
| 2014/0200274 A1 | 7/2014 | Frank et al. |
| 2016/0206661 A1 | 7/2016 | Fraser et al. |
| 2019/0015397 A1 | 1/2019 | Truchetet et al. |
| 2019/0307834 A1 | 10/2019 | Sekar et al. |
| 2024/0299414 A1 | 9/2024 | Benton et al. |

FOREIGN PATENT DOCUMENTS

WO    2022/036234 A1    2/2022

OTHER PUBLICATIONS

Ilomedin data sheet ( 2012, downloaded from the internet on Mar. 14, 2025) (Year: 2012).*

(Continued)

*Primary Examiner* — Savitha M Rao
(74) *Attorney, Agent, or Firm* — Troutman Pepper Locke LLP

(57) ABSTRACT

The present disclosure generally relates to treatment of systemic sclerosis with symptomatic Raynaud's Phenomenon by intravenous or subcutaneous administration of iloprost or a pharmaceutically acceptable salt thereof.

12 Claims, 1 Drawing Sheet

(56) References Cited

OTHER PUBLICATIONS

Krause et al., "Pharmacokinetics and biotransformation of the prostacyclin analogue, ZK 36 374, in the monkey (*Macaca fascicularis*)," Prostaglandins, leukotrienes, and medicine 11, 325-338 (1983).
Krause et al., "Pharmacokinetics and Pharmacodynamics of Radio-Labeled Iloprost in Elderly Volunteers", European Journal of Clinical Pharmacology, 1987, vol. 32, pp. 597-605.
Krause, "Pharmacokinetics and Pharmacodynamics of the Prostacyclin Analogue Iloprost in Man," Eur. J. Clin. Pharmacol 30:61-68 (1986).
Krause, W., "Pharmacokinetics and biotransformation of the prostacyclin analogue, ZK 36 374, in the beagle dog," Prostaglandins, leukotrienes, and medicine 13, 143-151 (1984).
Kyle et al., "Placebo controlled study showing therapeutic benefit of iloprost in the treatment of Raynaud's Phenomenon," J Rheumatol. 19:1403-1406 (1992).
Lacey et al., "An Institutional Protocol for the Treatment of Severe Frostbite Injury—A 6-Year Retrospective Analysis. Journal of burn care & research," Official publication of the American Burn Association 42:817-820 (2021).
Leroy et al., "Scleroderma (systemic sclerosis): classification, subsets and pathogenesis," J Rheumatol. Feb;15(2):202-205 (1988).
Leroy, "Systemic sclerosis. A vascular perspective," Rheum Dis Clin North Am. 1996; 22(4):675-694.
Levien et al., "Advances in the treatment of Raynaud's phenomenon," Vasc Health Risk Manag., 2010, vol. 6, pp. 167-177.
Limjeerajarus et al., "Characterization of a Thermo-Sensitive Injectable Hydrogel as an Iloprost Delivery System for Dental Use", Key Engineering Materials, Aug. 3, 2020, vol. 856, pp. 391-398.
Lindemann et al., "Prostacyclin inhibits adhesion of polymorphonuclear leukocytes to human vascular endothellal cells due to adhesion molecule independent regulatory mechanisms," Basic Res. Cardiol. 98: 8-15 (2003).
Linford et al., "The evolution of the Helsinki frostbite management protocol," Burns: journal of the International Society for Burn Injuries 43, 1455-1463 (2017).
Lye et al., "Effect of iloprost (ZK36374) and prostacyclin on in vitro human cerebral arteries," Br J Pharmacol 1986; 89:691, 1 page.
Magnum et al., Hyperbaric Oxygen Therapy with Iloprost Improves DI it Salvage in Severe Frostbite Compared to Iloprost Alone. Medicina (Kaunas, Lithuania) 57, 11 pages. (2021).
Majed et al., "Molecular mechanisms regulating the vascular prostacyclin pathways and their adaptation during pregnancy and in the newborn," Pharmacological reviews 64:540-582 (2012).
Matucci-Cerinic, "Digital ulcers and outcomes assessment in scleroderma," Rheumatology (Oxford). 2008; 47 (Suppl5):v46-47.
Matucci-Cerinic et al., "Elucidating the burden of recurrent and chronic digital ulcers in systemic sclerosis: long-term results from the DUO Registry," Ann Rheum Dis. Oct. 2016; 75(10):1770-1776. Epub Nov. 26, 2015.
Matucci-Cerinic et al., "Review: evidence that systemic sclerosis is a vascular disease," Arthritis Rheum. Aug. 2013; 65(8):1953-1962.
Mayes et al., "Endothelin and endothelin receptor antagonists in systemic rheumatic disease," Arthritis and Rheum. 2003; 48(5):1190-1199.
McHugh et al., "Infusion of iloprost, a prostacyclin analogue, for treatment of Raynaud's phenomenon in systemic sclerosis," Ann Rheum Dis 47:43-47 (1988).
McIntosh et al., "Wilderness Medical Society Clinical Practice Guidelines for the Prevention and Treatment of Frostbite," 2019 Update. Wilderness & environmental medicine 30, S19-S32 (2019).
McMahon et al., "Cold weather issues in sideline and event management," Current sports medicine reports 11:135-141 (2012).
Medsger, "Epidemiology of systemic sclerosis," Clin Dermatol. Apr.-Jun. 1994; 12(2):207-16.
Mehta et al., "Frostbite injury. Prediction of tissue viability with triple-phase bone scanning," Radiology 170:511-514 (1989).

Merkel et al., "Measuring disease activity and functional status in patients with scleroderma and Raynaud's Phenomenon," Arthritis Rheum. 2002; 46(9):2410-2420.
Milio et al., "Iloprost treatment in patients with Raynaud's phenomenon secondary to systemic sclerosis and the quality of life. A new therapeutic protocol," Rheumatology. (Oxford) 45, 999-1004 (2006).
Millett et al., "Frostbite. Spectrum of Imaging Findings and Guidelines for Management," Radiographics 36, 2154-2169 (2016).
Mills et al., Frostbite. Experience with rapid rewarming and ultrasonic therapy. Part III. 1961. Alaska Medicine 35:19-27 (1993).
Modesti et al., "Acute reversible reduction of PGI platelet receptors after iloprost infusion in man," Thromb Res. 1987; 48(6):663-669.
Mohr et al., "Cold injury," Hand clinics 25:481-496 (2009).
Mouthon et al., "Impact of digital ulcers on disability and health-related quality of life in systemic sclerosis," Ann Rheum Dis. Jan. 2010; 69(1):214-217.
Musial et al., "Fibrinolytic activity of prostacyclin and iloprost in patients with peripheral arterial disease," Prostaglandins 31:61-70 (1986).
Negrini et al., "Ioprost use and medical management of systemic sclerosis-related vasculopathy in Italian tertiary referral centers: results from the PROSIT study," Clinical and experimental medicine 19, 357-366 (2019).
Nicolini et al., "Inhibitory effect of unstimulated neutrophils on platelet aggregation by release of a factor similar to endothelium-derived relaxing factor (EDRF)," Biochem Pharmacol. 1990; 40(10):2265-2269.
Nihtyanova et al., "Clinical burden of digital vasculopathy in limited and diffuse cutaneous systemic sclerosis," Ann Rheum Dis. Jan. 2008; 67(1):120-3. Epub Jul. 27, 2007.
Olschewski et al., "Pharmacodynamics and pharmacokinetics of inhaled iloprost, aerosolized by three different devices, In severe pulmonary hypertension," Chest 124, 1294-1304 (2003).
Pandey et al., "Case Report. Severe Frostbite in Extreme Altitude Climbers—The Kathmandu Iloprost Experience," Wilderness & environmental medicine 29:366-374 (2018).
Patel et al., "Intra-arterial Thrombolysis for Extremity Frostbite Decreases Digital Amputation Rates and Hospital Length of Stay," Cardiovasc. Intervent. Radiol. 40:1824-1831 (2017).
Poole et al., "Management of severe frostbite with iloprost, alteplase and heparin," A Yukon case series. CMAJ open 9, E585-E591 (2021).
Poole et al., "Treatment of severe frostbite with iloprost in northern Canada", CMAJ : Canadian Medical Association journal = journal de'lAssociation medicale canadienne, 2016, vol. 188, pp. 1255-1258.
Poole et al., Whitehorse frostbite protocol. https://yukon.ca/en/whitehorse-frostbite-protocol, 9 pages (revised 2020).
Pope et al., "Raynaud's phenomenon (primary)," BMJ Clin Evid. 2013; Oct. 10, 2013; 2013:1119, 11 pages.
Rabl et al., "Long-term cyclic intravenous iloprost in systemic sclerosis: clinical experience from a single center," Reumatismo. 2012; 64(3):158-165.
Rademaker et al., "Comparison of intravenous infusions of iloprost and oral nifedipine in treatment of Raynaud's phenomenon in patients with systemic sclerosis: a double blind randomised study," Br Med J. 298:561-564 (1989).
Rademaker et al., "Prolonged increase in digital blood flow following Iloprost infusion in patients with systemic sclerosis," Postgraduate Medical Journal 63:617-620 (1987).
Robson et al., "Evaluation of hand frostbite blister fluid as a clue to pathogenesis," The Journal of hand surgery 6, 43-47 (1981).
Rogers et al., The Effects of Rapid Rewarming on Tissue Salvage in Severe Frostbite Injury. Journal of burn care & research : official publication of the American Burn Association 43, 906-911 (2022).
Rotondo et al., "Evidence for increase in finger blood flow, evaluated by laser Doppler flowmetry, following iloprost infusion in patients with systemic sclerosis. A week-long observational longitudinal study," Scandinavian journal of rheumatology 47:311-318 (2018).
Ruan et al., "Prostacyclin therapy for pulmonary arterial hypertension," Texas Heart Institute journal 37:391-399 (2010).

(56) References Cited

OTHER PUBLICATIONS

Sadler et al., "Recruitment of hard-to-reach population subgroups via adaptations of the snowball sampling strategy," Nurs Health Sci. 2010; 12(3):369-374.
Salimi et al., "Assessment of tissue viability in frostbite by 99mTc Pertechnetate Scintigraphy," AJR Am J Roentgenol 142:415-419 (1984).
Sanchez et al., "Immunosuppressive therapy in connective tissue diseases—associated pulmonary arterial hypertension", Chest, 2006, vol. 130, No. 1, pp. 182-189.
Schioppo et al., "Acute and chronic effects of two different intravenous iloprost regimens in systemic sclerosis. A pragmatic non-randomized trial," Rheumatology (Oxford, England) 57, 1408-1416 (2018).
Schror et al., "The antiplatelet and cardiovascular actions of a new carbacyclin derivative (ZK 36 374)—equipotent to PGI2 in vitro," Naunyn Schmiedebergs Arch. Pharmacol. 316, 252-255 (1981).
Scorza et al., "Effects of long-term cyclic iloprost therapy in systemic sclerosis with Raynaud's phenomenon. A randomized, controlled study," Clinical and experimental rheumatology 19, 503-508 (2001).
Sears et al., "Economic analysis of revision amputation and replantation treatment of finger amputation injuries", Plastic and Reconstructive Surgery, 2014, vol. 133, No. 4, pp. 827-840.
Shenaq et al., "Urban Frostbite. Strategies for Limb Salvage," Journal of burn care & research : official publication of the American Burn Association 40:613-619 (2019).
Silva et al. "Endothelial Dysfunction and Nailfold Videocapillaroscopy Pattern as Predictors of Digital Ulcers in Systemic Sclerosis: a Cohort Study and Review of the Literature," Clin Rev Allergy Immunol. Oct. 2015; 49(2):240-52.
Steen et al., "Digital ulcers: overt vascular disease in systemic sclerosis," Rheumatology (Oxford). Jun. 2009; 48 Suppl 3:iii19-24.
Steinberg et al., "Effect of a prostacyclin derivative (iloprost) on regional blood flow, sympathetic nerve activity, and baroreceptor reflex in the conscious rat," J Cardiovasc Pharmacol 11, 84-89 (1988).
Sunderkotter et al, "Pathophysiology and clinical consequences of Raynaud's phenomenon related to systemic sclerosis," Rheumatology (Oxford). 2006; 45 Suppl 3:iii33-35.
Taylor et al., Frostbite injuries during winter maneuvers. A long-term disability. Mll. Med 154:411-412 (1989).
Torley et al., "A double blind, randomised, multicentre comparison of two doses of intravenous iloprost in the treatment of Raynaud's phenomenon secondary to connective tissue diseases," Ann Rheum Dis. 1991; 50 (11):800-804.
Tremoli et al., "Mode of action of PGI2 and of its stable derivative iloprost on platelets and leukocytes," Throm Res Suppl. 1990; 11:33-42.
Trombetta et al., "Effects of Longterm Treatment with Bosentan and Iloprost on Nailfold Absolute Capillary Number, Fingertip Blood Perfusion, and Clinical Status in Systemic Sclerosis," The Journal of rheumatology 43, 2033-2041 (2016).
Tsai et al., "Interaction between platelet receptor and iloprost isomers," Biochim. Biophys. Acta 942, 220-226 (1988).
Tsou et al., "Scleroderma dermal microvascular endothelial cells exhibit defective response to pro-angiogenic chemokines," Rheumatology (Oxford). 2016; 55(4):745-754.
Twomey et al., "An open-label study to evaluate the safety and efficacy of tissue plasminogen activator in treatment of severe frostbite", The Journal of trauma 59, 1350-4; discussion 1354-1355 (2005).
Van Den Hoogen et al., "Classification Criteria for Systemic Sclerosis: An ACR-EULAR Collaborative Initiative," Arthritis Rheum. Nov. 2013; 65(11): 2737-2747. Published online Oct. 3, 2013.
Viswanath et al., "Systemic sclerosis: current concepts in pathogenesis and therapeutic aspects of dermatological manifestations," Indian J Dermatol. 2013; 58(4):255-268.
Walker et al., "Clinical risk assessment of organ manifestations in systemic sclerosis: a report from the EULAR Scleroderma Trials And Research group database," Ann Rheum Dis. Jun. 2007; 66(6):754-763. Epub Jan. 18, 2007.
Watson et al., "Seasonal variation of Raynaud's phenomenon secondary to systemic sclerosis.," J Rheumatol. 26:1734-1737 (1999).
Wigley, "Clinical practice," Raynaud's phenomenon. N Engl J Med. 2002; 347(13): 1001-1008.
Wigley et al., "Intravenous Iloprost Treatment of Raynaud's Phenomenon and Ischemic Ulcers Secondary to Systemic Sclerosis," J. Rheumatol 19:1407-1414 (1992).
Wigley et al., "Raynaud's Phenomenon," N Engl J Med 375, 556-665 (2016).
Wigley F.M., et al., "Intravenous Iloprost Infusion in Patients with Raynaud Phenomenon Secondary to Systemic Sclerosis", Annals of Internal Medicine, Feb. 1994, vol. 120, No. 3, pp. 199-206.
Wigley, "Raynaud's phenomenon and other features of scleroderma, including pulmonary hypertension," Curr Opin Rheumatol. 1996; 8(6):561-568.
Wong et al., "Dynamic bone imaging with 99mTc-labeled diphosphonates and 18F-NaF. Mechanisms and applications," Journal of nuclear medicine: official publication, Society of Nuclear Medicine 54: 590-599 (2013).
Woo et al., "Proposed treatment protocol for frostbite. A retrospective analysis of 17 cases based on a 3-year single-institution experience", Arch. Plast. Surg. 40, 510-516 (2013).
Yardumian et al., "Platelet hyperaggregability occurring during prolonged continuous intravenous infusions of prostacyclin analogue ZK 36374", British Journal of Haematology, vol. 60, No. 1, pp. 109-116 (1985).
Yardumian et al., "Successful treatment of Raynaud's syndrome with Iloprost, a chemically stable prostacyclin analogue," Br J Rheumatol 27: 220-226 (1988).
Young et al., "Hand Impairment in Systemic Sclerosis: Various Manifestations and Currently Available Treatment," Current Treatment Options in Rheumatology vol. 2, pp. 252-269 (2016).
Zachariae et al., "Treatment of ischaemic digital ulcers and prevention of gangrene with intravenous iloprost in systemic sclerosis," Acta Derm Venereol. 1996; 76(3):236-238 (1996).
Zhao et al., "Deep frostbite. Clinical characteristics and outcomes in northeastern China," Journal of tissue viability 29:110-115 (2020).
Zhu et al., "A prostacyclin analogue, iloprost, protects from bleomycin-induced pulmonary fibrosis in mice," Respir Res. 11:34, 12 pages (2010).
Afssaps, Medicines containing buflomedil: Suspension of marketing authorisation—Press release, Medicaments contenant du buflomedil: Suspension de l'autorisation de mise sur le marche—Communiqué [en ligne]. Disponible sur: http://www.afssaps.fr/Infos-de-securite/Communiques-Points-presse/Medicaments-contenant-du-buflomedil-Suspension-de-I-autorisation-de-mise-sur-le-marche-Communique. Feb. 2, 2011, 4 pages with English translation.
Al Yafi, "Using Intra-arterial tPA for Severe Frostbite Cases. An Observational Comparative Retrospective Study," J Burn Care Res. 2019; 40(6):907-912.
CDER (2004). Clinical Pharmacology and Biopharmaceutics Review(s), Part 2: In Drug Approval Package for Ventavis (iloprost) inhalation solution, for oral inhalation use (NDA 021779), 108 pages. https://www.accessdata.fda.gov/drugsatfda_docs/nda/2004/21-779_Ventavis_biopharmr_P2.pdf. Nov. 8, 2021.
CDER (2004b). Pharmacology Review(s): In Drug Approval Package for Ventavis (iloprost), 202 pages. https://www.accessdata.fda.gov/drugsatfda_docs/nda/2004/21- 779_Ventavis_pharmr.pdf, Nov. 8, 2021.
Downs, "The feasibility of creating a checklist for the assessment of the methodological quality both of randomised and non-randomised studies of health care interventions," J Epidemiol Community Health. 1998; 52(6):377-384.
Edmonson et al., "Abstract No. 52: Intra-Arterial Thrombolytic Therapy for Limb Salvage in Severe Frostbite," Scientific Session 6 I Arterial Lysis, Arterial Imaging, vol. 19, Issue 2, Supplement, S21-S22 Feb. 2008.
Lorentzen et al., "Interventions for frostbite injuries," Cochrane Database Syst Rev. 12:CD012980, 44 pages (2020).

(56) References Cited

OTHER PUBLICATIONS

Marsigny, "Mountain frostbite," The Newsletter of the International Society for Mountain Medicine 1998;8(3):8-10.

Morton et al., Quantitative Synthesis—An Update. Methods Guide for Comparative Effectiveness Reviews. 70 pages. (Prepared by the Scientific Resource Center under Contract No. 290-2012-0004-C). Rockville, MD: Agency for Healthcare Research and Quality; Feb. 2018.

Nygaard et al., "Time Matters in Severe Frostbite. Assessment of Limb/Digit Salvage on the Individual Patient Level," Journal of burn care & research: official publication of the American Burn Association 38:53-59 (2017).

Ozyazgan, Irfan M, Melli M, et al. Eicosanoids and inflammatory cells in frostbitten tissue: prostacyclin, thromboxane, polymorphonuclear leukocytes, and mast cells. Plast Reconstr Surg 1998; 101(7):1881-6.

Page, M.J., et al., "The PRISMA 2020 statement: an updated guideline for reporting systematic reviews," pp. 1-9 (2020).

Saemi et al., "Treatment of bilateral hand frostbite using transcatheter arterial thrombolysis after papaverine infusion," Cardiovasc Intervent Radiol. 32(6):1280-3.(Nov. 2009). Epub May 16, 2009.

Salimi et al., "Treatment of frostbite with i.v. streptokinase: an experimental study in rabbits," AJR Am J Roentgenol. 1987; 149:773-776.

Thompson, "Why sources of heterogeneity in meta-analysis should be investigated," BMJ. 1994; 309 (6965):1351-1355.

Maundrell et al., "Epidemiology of Raynaud's Phenomenon", Wigley et al. eds., Raynaud's Phenomenon: A Guide to Pathogenesis and Treatment, 2015, pp. 21-35.

Abraham et al., "Optimal management of digital ulcers in systemic sclerosis," Ther Clin Risk Manag. Jun. 15, 2015; 11:939-47. eCollection 2015.

Actelion Pharmaceuticals US, I. (2013). Ventavis (iloprost) Inhalation Solution Prescribing Information (San Francisco, CA), issued Nov. 2013, 24 pages.

Actelion Pharmaceuticals US, I. (2019). Ventavis (iloprost) Inhalation Solution Prescribing Information (San Francisco, CA), Dec. 2019, 22 pages.

Actelion Pharmaceuticals US, Inc. 2017, Ventavis (iloprost). [inhalation solution prescribing information]. San Francisco, CA. 23 pages, Oct. 2017.

Actelion Pharmaceuticals US, Inc. (2022). Ventavis (iloprost) inhalation solution, for oral inhalation use Prescribing Information (NDA 021779) (San Francisco, CA), 22 pages. https://www.accessdata.fda.gov/drugsatfda_docs/label/2022/021779s021lbl.pdf. Mar. 25, 2022.

Archer et al., ZK 36-374, a stable analog of prostacyclin, prevents acute hypoxic pulmonary hypertension in the dog. J Am Coll. Cardiol. 8:1189-1194 (1986).

Armstrong et al., Functional and ligand binding studies suggest heterogeneity of platelet prostacyclin receptors. Br J Pharmacol 97, 657-668 (1989).

Bagis et al., Effect of iloprost on contractile impairment and mitochondrial degeneration in ischemia-reperfusion of skeletal muscle. Physiology international 105:61-75 (2018).

Bali et al., "Discontinuing long-term Iloprost treatment for Raynaud's Phenomenon and systemic sclerosis. A single-center, randomized, placebo-controlled, double-blind study. Acta dermatovenerologica Alpina," Acta Dermatovenerol Alp Pannonica Adriat. 2011; 20(1):13-21.

Barnes et al., "Epidemiology of systemic sclerosis: incidence, prevalence, survival, risk factors, malignancy, and environmental triggers," Curr Opin Rheumatol. Mar. 2012; 24(2): 165-70.

Baron et al., "Consensus opinion of a North American Working Group regarding the classification of digital ulcers in systemic sclerosis," Clin Rheumatol. 2014; 33(2):207-214. Epub Dec. 20, 2013.

Battenfeld, "Studies on reproductive toxicity of iloprost in rats, rabbits and monkeys," Toxicol Lett 78, 223-234 (1995).

Bayer New Zealand Limited (2019). Ilomedin (iloprost) solution for infusion New Zealand Data Sheet (North Shore, Auckland, New Zealand). http://www.medsafe.govt.nz/profs/datasheet/i/Ilomedininf.pdf, dated Dec. 5, 2019, 13 pages.

Bellando-Randone et al., The safety of iloprost in systemic sclerosis in a real-life experience. Clin Rheumatol 37: 1249-1255 (2018).

Bertele et al., "Defective fibrinolytic response in atherosclerotic patients—effect of iloprost and its possible mechanism of action," Thromb. Haemost. 60:141-144 (1988).

Bettoni et al., Systemic sclerosis therapy with iloprost. A prospective observational study of 30 patients treated for a median of 3 years, Clin Rheumatol 21:244-250 (2002).

Biasi et al., Iloprost as cyclic five-day infusions in the treatment of scleroderma. An open pilot study in 20 patients treated for one year. Rev. Rhum. Engl. Ed 65:745-750 (1998).

Blake et al., Quantitative studies of bone in postmenopausal women using (18)F-fluoride and (99m)Tc-methylene diphosphonate. J. Nucl. Med. 43:338-345 (2002).

Boulas, "Amputations of the fingers and hand. Indications for replantation," The Journal of the American Academy of Orthopaedic Surgeons 6, 100-105 (1998).

Bouskela et al., "Affects of buflomedil on spontaneous vasomotion and mean arteriolar internal diameter in the hamster cheek pouch," Journal of vascular research 31, 287-294 (1994).

Boxer et al., Inhibition of polymorphonuclear leukocyte adherence by prostacyclin. J Lab Clin. Med 95, 672-678 (1980).

Bruen, "Reduction of the incidence of amputation in frostbite injury with thrombolytic therapy," Arch. Surg 142, 546-51; discussion 551-3 (2007).

Campbell et al., "Pathogenesis of systemic sclerosis: a vascular hypothesis," Semin Arthritis Rheum. 1975; 4 (4):351-368.

Cappelli et al., "Management of Raynaud phenomenon and digital ulcers in scleroderma," Rheum Dis Clin North Am. 2015; 41(3):419-438.

Caramaschi et al., "Evaluation of finger skin temperature in scleroderma patients cyclically treated with iloprost.," Joint Bone Spine. 2006; 73(1):57-61. Epub Sep. 16, 2005.

Carceller et al., "Amputation Risk Factors in Severely Frostbitten Patients," International journal of environmental research and public health Apr. 15, 2019; 16(8):1351, 8 pages.

Carmichael, "Remote Delivery of Thrombolytics Prior to Transfer to a Regional Burn Center for Tissue Salvage in Frostbite. A Single-center Experience of 199 Patients," Journal of burn care & research: official publication of the American Burn Association 43:54-60 (2022).

Carpentier, "Norepinephrine, phentolamine and buflomedil influence n arteriolar vasomotion in the hamster skinfold preparation," Blood vessels 28 Suppl 1, 33-37 (1991).

Cauchy et al., "A Controlled Trial of a Prostacyclin and rt-PA in the Treatment of Severe Frostbite," N EENGL J Med 364:189-190 (Jan. 13, 2011).

Cauchy et al., "A New Proposal for Management of Severe Frostbite in the Austere Environment," Wilderness & environmental medicine 27:92-99 (2016).

Cauchy et al., "Retrospective study of 70 cases of severe frostbite lesions," A proposed new classification scheme. Wilderness & environmental medicine 1:248-255 (2001).

Cauchy et al., Supplement; A controlled trial of a prostacyclin and rt-PA in the treatment of severe frostbite. N Engl J Med 2011; 364:189-90, 2 pages.

Cauchy et al., "The role of bone scanning in severe frostbite of the extremities. A retrospective study of 88 cases," European journal of nuclear medicine 27:497-502 (2000a).

Cauchy, "The value of technetium 99 scintigraphy in the prognosis of amputation in severe frostbite injuries of the extremities. A retrospective study of 92 severe frostbite injuries," The Journal of hand surgery 25:969-978 (2000).

Ceru et al., "Effects of five-day versus one-day infusion of iloprost on the peripheral microcirculation in patients with systemic sclerosis," Clinical and Experimental Rheumatology 15:381-385 (1997).

Cestelli et al., "Effect of treatment with iloprost with or without bosentan on nallfold video capillaroscopic alterations in patients with systemic sclerosis," Modern rheumatology 27, 110-114 (2017).

(56) References Cited

OTHER PUBLICATIONS

Cheguillaume, Benoit, "Controlled trial of iloprost and rt-PA in the treatment of severe frostbite," Human Medicine and Pathology, 71 pages (Jun. 21, 2011).
Chung and Fiorentino, "Digital ulcers in patients with systemic sclerosis," Autoimmun Rev. Feb. 2006; 5 (2):125-128. Epub Sep. 13, 2005.
Chung et al., "Combined administration of nitric oxide gas and iloprost during cardiopulmonary bypass reduces platelet dysfunction," A pilot clinical study. J Thorac. Cardiovasc. Surg. 129:782-790 (2005).
Colaci et al., "Long-term treatment of scleroderma-related digital ulcers with iloprost. A cohort study," Clinical and experimental rheumatology 35 Suppl 106:179-183 (2017).
CoTherix, Inc. (2004) Drug Approval Package for Ventavis (iloprost) inhalation solution, for oral inhalation use (NDA 021779). Clinical Pharmacology and Biopharmaceutics Review(s), Part 2. https://www.accessdata.fda.gov/drugsatfda_docs/nda/2004/21-779_Ventavis_biopharm_P2.pdf. Nov. 8, 2021, 108 pages.
CoTherix, Inc. (2004). Drug Approval Package for Ventavis (iloprost) inhalation solution, for oral inhalation use (NDA 021779). Pharmacology Review(s). In https://www.accessdata.fda.gov/drugsatfda_docs/nda/2004/21-779_Ventavis_pharmr.pdf. Nov. 8, 2021, 202 pages.
Cowley et al., "Effects of Prostacyclin and of the Stable Prostacyclin Analogue ZK 36374 on Forearm Blood Flow and Blood Platelet Behaviour in Man," Thrombosis and Haemostasis 1985, pp. 90-94.
Crooks et al., "Effectiveness of intravenous prostaglandin to reduce digital amputations from frostbite: an observational study," Canadian Journal of Emergency Med. Epub Jul. 23, 2022, 8 pages.
Crooks et al., Supplement 1 to "Effectiveness of intravenous prostaglandin to reduce digital amputations from frostbite: an observational study," Canadian Journal of Emergency Med. Epub Jul. 23, 2022, 1 page (2022).
Crooks et al., Supplement 2 to "Effectiveness of intravenous prostaglandin to reduce digital amputations from frostbite: an observational study," Canadian Journal of Emergency Med. 24:622-629) Epub Jul. 23, 2022, 8 pages (2022).
Cutolo et al., "Longterm treatment with endothelin receptor antagonist bosentan and iloprost improves fingertip blood perfusion in systemic sclerosis," The Journal of rheumatology 41:881-886 (2014).
Czeslick et al., "Inhibition of intracellular tumour necrosis factor (TNF)-alpha and interleukin (IL)-6 production in human monocytes by iloprost," Eur J Clin Inves. 2003; 33(11):1013-1017.
D'Amelio et al., "Iloprost modulates the immune response in systemic sclerosis," BMC Immunol. 2010; 11:62, 8 pages.
De Putter et al., "Economic impact of hand and wrist injuries. Health-care costs and productivity costs in a population-based study," The Journal of bone and joint surgery. American vol. 94, e56 (2012).
Della Bella et al., "Cytokine production in scleroderma patients. Effects of therapy with either iloprost or nifedipine." Clinical and experimental rheumatology 15, 135-141 (1997).
Denton et al., "Systemic sclerosis," Lancet. 2017; 390(10103):1685-1699.
Dowd et al., "Effect of prostaglandins 12 and E1 on red cell deformability in patients with Raynaud's phenomenon and systemic sclerosis," Br Med J (Clin Res. Ed) 283, 350 (1981).
Edlich et al., "Cold injuries," Compr Ther 15, 13-21 (1989).
Endorf et al., "Biopsychosocial factors associated with complications in patients with frostbite," Medicine 2022; 101:34(e30211), pp. 1-5.
Endorf et al., "Socioeconomic and comorbid factors associated with frostbite injury in the United States," J Burn Care Res. May 17, 2022; 43(3):646-651.
Ercan et al., The relaxing activity of iloprost and prostaglandin E2 in the Isolated various smooth muscle strips of the rabbit. Pharmacology. 1985; 31(2):61-66.
Ervasti et al., "Sequelae of moderate finger frostbite as assessed by subjective sensations, clinical signs, and thermophysiological responses," Int. J Circumpolar. Health 59, 137-145 (2000).
Fabian et al., "A retrospective cohort study examining treatments and operative interventions for frostbite in a tertiary care hospital," CJEM 19, 88-95 (2017).
Ferri et al., "Systemic sclerosis: demographic, clinical, and serologic features and survival in 1,012 Italian patients," Medicine (Baltimore). Mar. 2002; 81(2):139-53.
Fisher et al., "Comparison of equimolar concentrations of iloprost, prostacyclin, and prostaglandin E1 on human platelet function," J Lab Clin Med 109, 184-190 (1987).
Foti et al., "Long-term clinical stabilization of scleroderma patients treated with a chronic and intensive IV iloprost regimen," Rhematol Int 2017; 37(2):245-249.
Freedman et al., "Nitric Oxide and Superoxide Detection in Human Platelets," Methods in Enzymology, vol. 301, 10 pages (1999).
Fudge, "Preventing and Managing Hypothermia and Frostbite Injury," Sports health 8:133-139 (2016).
Galanakos et al., "Psychological and social consequences after reconstruction of upper extremity trauma," Methods of detection and management. Journal of reconstructive microsurgery 30, 193-206 (2014).
Garcia de la Pena Lefebvre et al, "Efficacy of Raynaud's Phenomenon and digital ulcer pharmacological treatment in systemic sclerosis patients: a systematic literature review," Rheumatol Int 2015; 35(9):1447-1459.
Garner et al., "Prevalence, risk factors and associations of primary Raynaud's phenomenon: systematic review and meta-analysis of observational studies," BMJ Open. 2015; 5(3):e006389, pp. 1-9.
Gomez-Arronyo et al., "Iloprost reverses established fibrosis in experimental right ventricular failure," Eur Respir J 2015; 45(2):449-462.
Grant et al., "Iloprost. A review of its pharmacodynamic and pharmacokinetic properties, and therapeutic potential in peripheral vascular disease, myocardial ischaemia and extracorporeal circulation procedures," Drugs. 1992; 43 (6):889-924.
Greenwald et al., "An algorithm for early aggressive treatment of frostbite with limb salvage directed by triple-phase scanning," Plast. Reconstr. Surg. 102, 1069-1074 (1998).
Groechenig, Treatment of frostbite with iloprost. Lancet 344, 1152-1153 (1994).
Haberey et al., "Hemodynamic profile of iloprost in rats, rabbits, and cats. In Prostacyclin and its stable analogue iloprost," R.J. Gryglewski and G. Stock, eds. (Berlin (Germany): Springer-Verlag), pp. 151-158 (1987).
Hachulla et al., "Natural history of ischemic digital ulcers in systemic sclerosis: single-center retrospective longitudinal study," J Rheumatol Dec. 2007; 34(12):2423-30. Epub Nov. 1, 2007.
Handford et al., "Frostbite. A practical approach to hospital management," Extreme physiology & medicine 3:7, 10 pages (2014).
Hannah, "Psychosocial issues after a traumatic hand injury. Facilitating adjustment. Journal of hand therapy," Official journal of the American Society of Hand Therapists 24, 95-102; quiz 103 (2011).
Haye-Legrand et al., "Relaxation of isolated human pulmonary muscle preparations with prostacyclin (PGI2) and its analogs," Prostaglandins 33, 845-854 (1987).
Herman et al., "Critical evaluation of the in vivo selectivity between hypotensive and platelet antiaggregating actions of iloprost and prostacyclin in beagle dogs," Arch. Int. Pharmacodyn. Ther. 300, 281-291 (1989).
Herrick, "Raynaud's phenomenon (secondary)," BMJ Clin Evid. 2008; 09:1125, 34 pages. Published online Sep. 26, 2008.
Hickey et al., "Guidelines for Thrombolytic Therapy for Frostbite", Journal of burn care & research, Official publication of the American Burn Association vol. 41, No. 1, pp. 176-183 (2020).
Hildebrand et al., "Pharmacokinetics of iloprost in patients with chronic renal failure and on maintenance haemodialysis," Int J Clin Pharmacol Res. 1990; 10(5):285-292.
Hildebrand et al., "Pharmacokinetics of iloprost in patients with hepatic dysfunction," Int J Clin Pharmacol Ther Toxicol. 1990; 28(10):430-434.
Hildebrand et al., "Pharmacokinetics of iloprost in patients with severe peripheral arterial occlusive disease," Eicosanoids. 1990; 3(3):145-148.

(56) References Cited

OTHER PUBLICATIONS

Hildebrand, "Pharmacokinetics of iloprost and cicaprost in mice," Prostaglandins 44:431-442 (1992).

Hinchcliff et al., "Systemic sclerosis/scleroderma: a treatable multisystem disease," Am Fam Physician. 2008; 78 (8):961-968.

Hughes et al., "Digital ulcers in systemic sclerosis," Rheumatology (Oxford). 2017; 56(1):14-25.

Hummers et al., "Management of Raynaud's phenomenon and digital ischemic lesions in scleroderma," Rheum Dis Clin North Am. May 2003; 29(2):293-313.

Hutchinson, "Frostbite of the hand," The Journal of hand surgery 39:1863-1868 (2014).

Ilomedin Data Sheet by Bayer, dated Mar. 19, 2012, 13 pages.

Imray et al., "Cold damage to the extremities. Frostbite and nonfreezing cold injuries," Postgraduate medical journal 85:481-488 (2009).

International Preliminary Report on Patentability for International Application No. PCT/US2021/045013 dated Feb. 16, 2023, 13 pages.

International Preliminary Report on Patentability for International Application No. PCT/US2021/045963 dated Feb. 23, 2023, 8 pages.

International Search Report and Written Opinion for International Application No. PCT/US2021/045013 dated Dec. 21, 2021, 18 pages.

Ioannou et al., "Platelet antiaggregatory substances inhibit arachidonic acid induced coronary constriction," Can J Physiol Pharmacol 64(4):398-405 (1986).

Kahaleh, "Endothelin, an endothelial-dependent vasoconstrictor in scleroderma. Enhanced production and profibrotio action," Arthritis Rheum. Aug. 1991; 34(8):978-83. doi: 10.1002/art.1780340807.

Kawald et al., "Low versus high-dose iloprost therapy over 21 days in patients with secondary Raynaud's phenomenon and systemic sclerosis: a randomized, open, single-center study," J Rheumatol. 2008; 35(9):1830-1837.

Keller et al., "Behandlung des Raynaud-Phanomens bei Sklerodermie-Patienten mit einem neuen stabilen Prostacyclin-Derivat," [Treatment of Raynaud's phenomenon in scleroderma with a new stable prostacyclin derivative] Dtsch Med Wochenschr 1984; 109(38):1433-1438, 1 page English Abstract only.

Khanna et al., Effect of Macitentan on the Development of New Ischemic Digital Ulcers in Patients With Systemic Sclerosis DUAL-1 and DUAL-2 Randomized Clinical Trials. JAMA. 2016; 315(18):1975-1988.

Koljonen et al., "Frostbite injuries treated in the Helsinki area from 1995 to 2002," The Journal of trauma 57:1315-1320 (2004).

Kowal-Bielecka et al., "Update of EULAR recommendations for the treatment of systemic sclerosis," Ann Rheum Dis. 2017; 76(8):1327-1339.

Viechtbauer, "Conducting Meta-Analyses in R with the metafor Package," Journal of Statistical Software 36(3):1-48 (2010).

Wexler et al., "The Use of Thrombolytic Therapy in the Treatment of Frostbite Injury," J Burn Care Res. 2017; 38 (5):e877-e881.

Yigit, "Review of our 10 years experience in cold burns at the burn center in the Southeast Anatolia region of Turkey," Ulus Travma Acil Cerrahi Derg. 2022; 28(3):369-374.

Zhang et al., "Management and Outcome of Feet Deep Frostbite Injury (II and IV Degrees): A Series Report of 36 Cases," Int J Low Extrem Wounds. 2022; 21(3):325-331.

Gauthier et al., "Iloprost for the treatment of frostbite: a scoping review", International Journal of Circumpolar Health, vol. 82, 2189552, pp. 1-15 (Mar. 26, 2023).

International Search Report and Written Opinion for PCT Application No. PCT/US2024/038455 mailed Sep. 10, 2024 10 pages.

Jin et al., "Expert consensus on the prevention, diagnosis and treatment of cold injury in China, 2020", Military Medical Research, vol. 8, No. 6, pp. 1-13 (Jan. 21, 2021).

International Search Report and Written Opinion for International Patent Application PCT/US2021/045963, mailed on Nov. 22, 2021, 14 pages.

Metcalfe, "Microbiological Quality of Drug Products after Penetration of the Container System for Dose Preparation Prior to Patient Administration", American Pharmaceutical Review, 2009, 7 pages.

Gomez-Broughton, "Aseptic Processing of Biological Products: Current Regulatory Issues", Aug. 2018, CDER Microbiology Issues: A Deeper Dive, 33 pages.

The World Health Organization guidance on the subject: WHO Technical Report Series, No. 863, Thirty-fourth Report, 1996, Annex 5—Guidelines for stability testing of pharmaceutical products containing well established drug substances in conventional dosage forms, pp. 65-79.

Gibaldi et al., "Pharmacokinetics", 2nd ed. New York: Marcel Dekker, Inc., 1982, Chapter 11, pp. 409-417.

\* cited by examiner

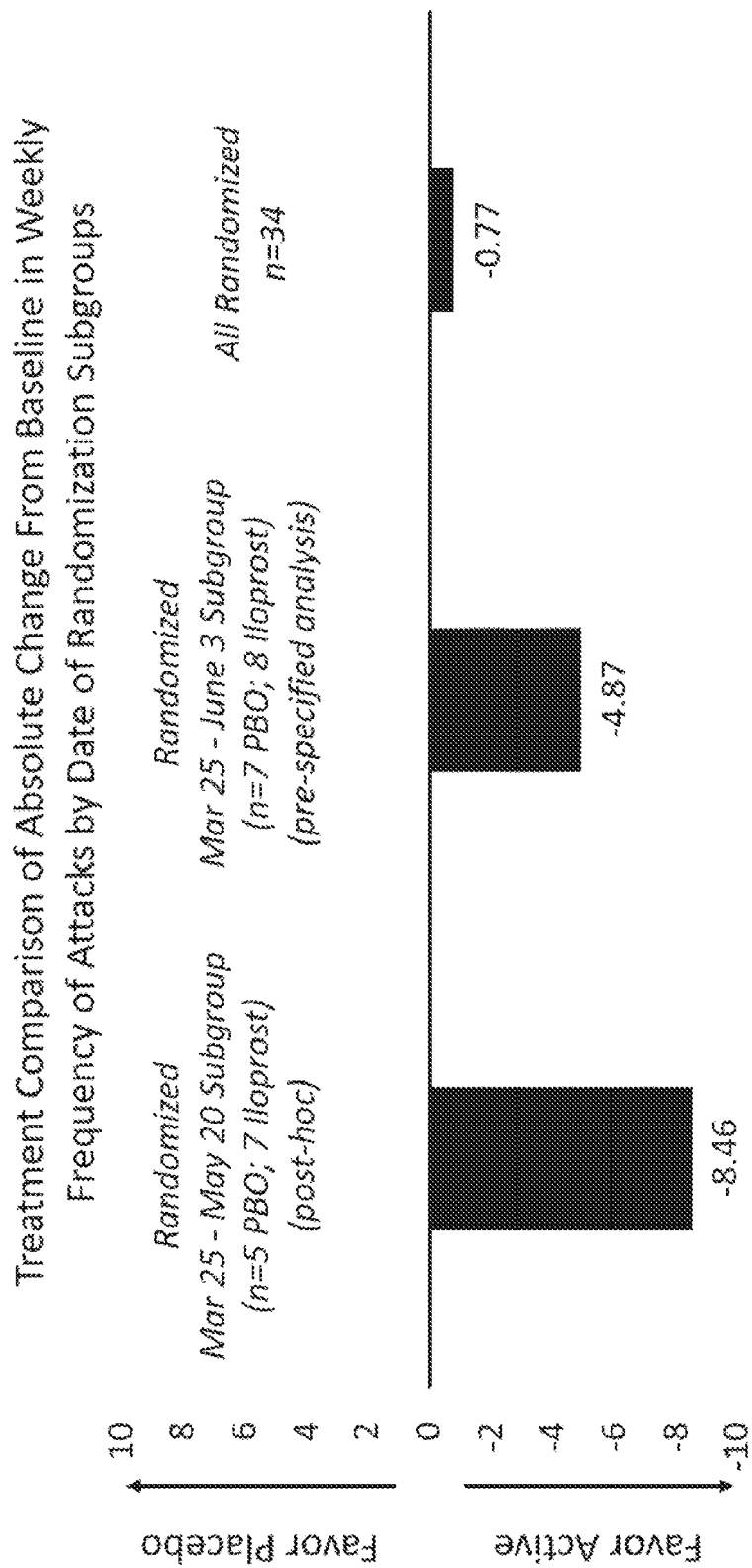

ILOPROST COMPOSITIONS AND FORMULATIONS THEREOF

CROSS-REFERENCE TO RELATED APPLICATIONS

This application is a continuation of U.S. application Ser. No. 18/260,778, filed on Jul. 7, 2023, which is a U.S. National Phase of International Application No. PCT/US2021/045013 filed on Aug. 6, 2021, which claims priority to U.S. Provisional Application No. 63/062,812, filed on Aug. 7, 2020. The entire contents of these applications are incorporated by reference herein in their entirety.

FIELD OF THE INVENTION

The present disclosure generally relates to treatment of systemic sclerosis with symptomatic Raynaud's Phenomenon by intravenous or subcutaneous administration of iloprost or a pharmaceutically acceptable salt thereof.

BACKGROUND OF THE INVENTION

Systemic Sclerosis (SSc), also known as scleroderma, is a rare, autoimmune disease with pathogenesis characterized by small vessel vasculopathy primarily affecting small arteries and arterioles, production of autoantibodies, and fibroblast dysfunction leading to increased deposition of extracellular matrix in the skin and internal organs (van de Hoogen et al., 2013; Denton et al., 2017). The clinical manifestations and prognosis of SSc are heterogeneous; most patients have skin thickening and variable involvement of cardiovascular, gastrointestinal (GI), musculoskeletal, and pulmonary systems (Hinchcliff, et al., 2008). Subsets of SSc can be discerned; these include limited cutaneous SSc, diffuse cutaneous SSc, and SSc without skin involvement (sine SSc) (van den Hoogen et al., 2013). The diffuse cutaneous form is characterized by dermal thickening and fibrosis proximal to the elbows and ankles and a higher risk of internal organ involvement compared to other forms. In limited cutaneous SSc, skin involvement is confined to the face, hands, feet, and/or forearms. In sine SSc, there is no skin involvement, but the condition is associated with characteristic scleroderma-associated autoantibodies and internal organ involvement (LeRoy et al., 1988; Wigley et al., 1994). Systemic sclerosis is a rare disease. Incidence rates and prevalence estimates are similar for Europe, the United States, Australia, and Argentina, suggesting a prevalence of 150-300 cases per million, with a lower prevalence noted in Scandinavia, Japan, the United Kingdom, Taiwan, and India (Barnes, et al., 2012). SSc is associated with substantial morbidity, reduced survival, and poor quality of life (QoL) (Medsger, et al., 1994; Wigley et al., 1994; Mayes, et al., 2003; Barnes, et al., 2012; Denton, et al., 2017).

Digital ischemic episodes (Raynaud's Phenomenon) are the most common manifestation of vascular abnormalities in SSc and a universal feature of SSc disease, affecting more than 95% of patients. Digital ischemic episodes were first described by Maurice Raynaud in 1862 when he recognized that some people who were exposed to cold temperature or emotional stress, had transient digital ischemia. The term "Raynaud's Phenomenon" (RP) is used to describe these digital ischemic episodes. RP affects 3-5% of people in the United States (US), mostly women, and is categorized in primary and/or secondary forms (Maundrell et al. *Raynaud's Phenomenon: A Guide to Pathogenesis and Treatment.* New York, NY Springer; 2015:21-35; Pope et al. BMJ Clin Evid. 2013; 2013:1119). Primary RP is characterized by the absence of an underlying condition or disorder, is responsible for most cases of RP (80-90%) (Maundrell 2015; Pope 2013) and typically develops at an early age, usually before the age of 30 (Levien et al. Vasc Health Risk Manag. 2010; 6:167-177; Gamer et al. BMJ Open. 2015; 5 (3): e006389). Primary RP typically presents as symmetric attacks and is not associated with severe sequelae. Secondary RP develops in association with an underlying disease or condition— usually a connective tissue disease, such as SSc—and typically begins after the age of 30 (Levien 2010). RP secondary to SSc is associated with significant disability, pain, and psychological impact (Merkel et al. Arthritis & Rheumatism. 2002; 46 (9): 2410-20). In addition to pain, annoyance, and functional disability caused by RP attacks, many patients with SSc report that they change their daily routine to accommodate their RP and may have significant anxiety associated with their disease, often expressing fears concerning digital ulcers and potential autoamputation (Merkel 2002).

RP represents vasoconstriction of the digital arteries, precapillary arterioles and cutaneous arteriovenous shunts in response to cold or stress. In SSc, RP is associated with obliterative vasculopathy and structural changes and progress from biphasic to triphasic color changes of the fingers, toes, and other peripheral tissue without or with symptoms to digital ischemic ulcers and critical digital ischemia and to gangrene over time (Young et al., 2016). RP is also associated with recurrent painful attacks significant disability and psychological impact in patients with SSc (Merkel et al., 2002; Hummers et al., 2003).

RP in systemic sclerosis results from both functional and structural vascular abnormalities (Abraham and Steen, 2015). The structural component is twofold; the first marker is intimal proliferation and fibrosis, causing significant compromise of the vessel lumen. The resultant endothelial damage leads to the upregulation of vasoconstrictive mediators, such as endothelin-1 (Kahalch, 1991), while simultaneously lowering the levels of vasodilatory molecules, such as nitric oxide (NO) (Freedman et al., 1999) and prostacyclin (Abraham, et al., 2015). The functional component results from frequent vasospasm, contributed by increased sympathetic activation, which over time may lead to progressive tissue ischemia and the formation of oxygen-free radicals, perpetuating this cycle (Abraham, et al., 2015). Small blood vessels in affected tissues from patients with SSc show perivascular cellular infiltration by activated T-lymphocytes, similar to that seen in affected skin and internal organs (Kahaleh, 1991). The endothelial damage underlying the vasculopathy in SSc is also associated with platelet activation (Matucci-Cerinic et al., 2013). Digital ischemic ulcers (DIUs) are a frequent external manifestation of vasculopathy in SSc (Nihtyanova et al., 2008). DIUs are denuded areas of tissue that occur either at distal aspects of digits or over bony prominences with well-demarcated borders, involving loss of both the dermis and epidermis (Baron et al., 2014). Repeated bouts of RP lead to prolonged digital ischemia that may progress to DIU or extreme critical digital ischemia with gangrene (Silva et al., 2015). DIUs occur in up to 58% of patients with limited or diffuse SSc and often occur early in the disease course (Ferri et al., 2002; Walker et al., 2007; Matucci-Cerinic et al., 2016). A 30% annual incidence of SSc DIU has been reported in the literature. Of those patients who experience a DIU, more than half have persistent or recurrent DIUs for at least 6 months (Steen et al., 2009; Matucci-Cerinic et al., 2016). Several studies have shown that the lesions are painful, heal slowly, lead to substantial functional disability, and are associated with complications such as scarring, loss of distal tissue, infection, gangrene, amputation leading to reduced QoL, an increased frequency of hospitalization, and decreased survival (Chung and Fiorentino, 2006; Hachulla et al., 2007; Mouthon et al., 2010; Matucci-Cerinic et al., 2016). Several factors are implicated in the pathogenesis of DIUs in SSc. These include (1) impaired afferent vasomotion (highlighted by the intimal hyperplasia of arterioles), (ii) disrupted capillary and lymphatic microvasculature, (iii) leucocyte and platelet activation and adherence to injured endothelium, and (iv) haemorheological alterations typical of SSc. The disease is also characterized by insufficient angiogenesis and defective vasculogenesis, contributing further to tissue ischemia (Tsou et al., 2016).

SUMMARY OF THE INVENTION

The present disclosure provides methods of reducing a weekly average frequency of symptomatic Raynaud's Phenomenon (RP) attacks from baseline in a subject with systemic sclerosis experiencing symptomatic RP attacks, comprising intravenously or subcutaneously administering iloprost or a pharmaceutically acceptable salt thereof at about 0.5 ng/kg/min to about 2.0 ng/kg/min for about 6 hours a day for 5 consecutive days;
    wherein one episode of a symptomatic RP attack comprises at least one color change of the subject's fingers and at least one symptom of the fingers selected from pain, numbness, tingling, or discomfort; and
    wherein the baseline frequency is a weekly average of the number of symptomatic RP attack episodes in the subject measured daily for 10 to 25 days prior to the administration of iloprost or a pharmaceutically acceptable salt thereof.

In embodiments of the methods disclosed herein, a treatment effect of iloprost or a pharmaceutically acceptable salt thereof on the weekly average frequency of symptomatic RP attacks is in the range of about −2.0 to about −15.0. In embodiments, the treatment effect of iloprost or a pharmaceutically acceptable salt thereof on the weekly average frequency of symptomatic RP attacks is in the range of about −3.0 to about −8.0.

In embodiments of the methods disclosed herein, the weekly average frequency of symptomatic RP attacks is reduced by about 10% to about 90% from the baseline weekly average frequency. In embodiments, the weekly average frequency of symptomatic RP attacks is reduced by about 15% to about 60% from the baseline weekly average frequency. In embodiments, the weekly average frequency of symptomatic RP attacks is reduced by about 25% to about 55% from the baseline weekly average frequency. In embodiments, the weekly average frequency of symptomatic RP attacks is reduced by at least about 30% from the baseline weekly average frequency.

In embodiments of the methods disclosed herein, the weekly average frequency of symptomatic RP attacks is reduced from the baseline weekly average frequency for a duration in the range of about 1 weeks to about 15 weeks after the end of administration of iloprost or a pharmaceutically acceptable salt thereof. In embodiments, the weekly average frequency of symptomatic RP attacks is reduced from the baseline weekly average frequency for a duration in the range of about 2 weeks to about 12 weeks after the end of administration of iloprost or a pharmaceutically acceptable salt thereof. In embodiments, the weekly average frequency of symptomatic RP attacks is reduced from the baseline weekly average frequency for at least about 2 weeks after the end of administration of iloprost or a pharmaceutically acceptable salt thereof. In embodiments, the weekly average frequency of symptomatic RP attacks is reduced from the baseline weekly average frequency for at least about 8 weeks after the end of administration of iloprost or a pharmaceutically acceptable salt thereof.

In embodiments of the methods disclosed herein, the baseline weekly average frequency and the weekly average frequency after the administration of iloprost or a pharmaceutically acceptable salt thereof are determined based on the number of symptomatic RP attack episodes recorded by the subject daily.

The present disclosure provides methods of reducing a weekly average duration of symptomatic Raynaud's Phenomenon (RP) attacks from baseline in a subject with systemic sclerosis experiencing symptomatic RP attacks, comprising intravenously or subcutaneously administering iloprost or a pharmaceutically acceptable salt thereof at about 0.5 ng/kg/min to about 2.0 ng/kg/min for about 6 hours a day for 5 consecutive days;
    wherein one episode of a symptomatic RP attack comprises at least one color change of the subject's fingers and at least one symptom of the fingers selected from pain, numbness, tingling, or discomfort; and
    wherein the baseline duration is a weekly average of the total duration of all symptomatic RP attack episodes in the subject measured daily for 10 to 25 days prior to the administration of iloprost or a pharmaceutically acceptable salt thereof.

In embodiments of the methods disclosed herein, a treatment effect of iloprost or a pharmaceutically acceptable salt thereof on the weekly average duration of symptomatic RP attacks is about −45 minutes to about −300 minutes. In embodiments, the treatment effect of iloprost or a pharmaceutically acceptable salt thereof on the weekly average duration of symptomatic RP attacks is about −60 minutes to about −150 minutes.

In embodiments of the methods disclosed herein, the weekly average duration of symptomatic RP attacks is reduced by about 10% to about 90% from the baseline weekly average duration. In embodiments, the weekly average duration of symptomatic RP attacks is reduced by about 15% to about 60% from the baseline weekly average duration. In embodiments, the weekly average duration of symptomatic RP attacks is reduced by about 25% to about 55% from the baseline weekly average duration. In embodiments, the weekly average duration of symptomatic RP attacks is reduced by at least about 30% from the baseline weekly average duration.

In embodiments of the methods disclosed herein, the weekly average duration of symptomatic RP attacks is reduced from the baseline weekly average duration for a time period in the range of about 2 weeks to about 15 weeks after the end of administration of iloprost or a pharmaceutically acceptable salt thereof. In embodiments, the weekly average duration of symptomatic RP attacks is reduced from the baseline weekly average duration for a time period in the range of about 2 weeks to about 12 weeks after the end of administration of iloprost or a pharmaceutically acceptable salt thereof. In embodiments, the weekly average duration of symptomatic RP attacks is reduced from the baseline weekly average duration for at least about 2 weeks after the end of administration of iloprost or a pharmaceutically acceptable salt thereof. In embodiments, the weekly average duration of symptomatic RP attacks is reduced from the baseline weekly average duration for at least about 8 weeks after the end of administration of iloprost or a pharmaceutically acceptable salt thereof.

In embodiments of the methods disclosed herein, the baseline weekly average duration and the weekly average duration after the administration of iloprost or a pharmaceutically acceptable salt thereof are determined based on duration of each symptomatic RP attack episode recorded by the subject daily.

The present disclosure provides methods of reducing a weekly average severity of symptomatic Raynaud's Phenomenon (RP) attacks from baseline in a subject with systemic sclerosis experiencing symptomatic RP attacks, comprising intravenously or subcutaneously administering iloprost or a pharmaceutically acceptable salt thereof at about 0.5 ng/kg/min to about 2.0 ng/kg/min for about 6 hours a day for 5 consecutive days;
- wherein the severity of RP attacks is measured by a symptom of the fingers with a worst baseline weekly average score selected from pain, numbness, discomfort, or tingling, based on a numeric rating scale;
- wherein the baseline weekly average severity score is determined from the subject's daily numeric rating of the symptom for 10 to 25 days prior to the administration of iloprost or a pharmaceutically acceptable salt thereof.

In embodiments of the methods disclosed herein, a treatment effect of iloprost or a pharmaceutically acceptable salt thereof on the weekly average severity score of symptomatic RP attacks is about −0.3 to about −2.0, wherein the numeric rating scale is from 0 to 10. In embodiments, the treatment effect of iloprost or a pharmaceutically acceptable salt thereof on the weekly average severity score of symptomatic RP attacks is about −0.6 to about −1.5, wherein the numeric rating scale is from 0 to 10.

In embodiments of the methods disclosed herein, the weekly average severity of symptomatic RP attacks is reduced by about 10% to about 90% from the baseline weekly average severity score. In embodiments, the weekly average severity of symptomatic RP attacks is reduced by about 15% to about 60% from the baseline weekly average severity score. In embodiments, the weekly average severity of symptomatic RP attacks is reduced by about 20% to about 50% from the baseline weekly average severity score. In embodiments, the weekly average severity of symptomatic RP attacks is reduced by at least about 20% from the baseline weekly average severity score.

In embodiments of the methods disclosed herein, the weekly average severity of symptomatic RP attacks is reduced by a number in the range of about 0.2 to about 5.0 from the baseline weekly average severity score, wherein the numeric rating scale is from 0 to 10. In embodiments, the weekly average severity of symptomatic RP attacks is reduced by a number in the range of about 0.5 to about 3.0 from the baseline weekly average severity score, wherein the numeric rating scale is from 0 to 10.

In embodiments of the methods disclosed herein, the weekly average severity of symptomatic RP attacks is reduced from the baseline weekly average severity score for a time period in the range of about 2 weeks to about 15 weeks after the end of administration of iloprost or a pharmaceutically acceptable salt thereof. In embodiments, the weekly average severity of symptomatic RP attacks is reduced from the baseline weekly average severity score for a time period in the range of about 2 weeks to about 12 weeks after the end of administration of iloprost or a pharmaceutically acceptable salt thereof. In embodiments, the weekly average severity of symptomatic RP attacks is reduced from the baseline weekly average severity score for at least about 2 weeks after the end of administration of iloprost or a pharmaceutically acceptable salt thereof. In embodiments, the weekly average severity of symptomatic RP attacks is reduced from the baseline weekly average severity score for at least about 8 weeks after the end of administration of iloprost or a pharmaceutically acceptable salt thereof.

In embodiments of the methods disclosed herein, the baseline weekly average severity score and the weekly average severity after the administration of iloprost or a pharmaceutically acceptable salt thereof are determined based on a daily numeric rating of symptoms of the fingers recorded by the subject for pain, numbness, discomfort, and tingling, wherein the daily numeric rating reflects the value of the worst symptom in a given day. In embodiments, if the baseline weekly average score is the same value for two symptoms of the fingers, the baseline weekly average will be based on the following order of rank: pain>numbness>tingling>discomfort.

The present disclosure provides methods of determining the effect of iloprost or a pharmaceutically acceptable salt thereof in a subject with systemic sclerosis experiencing symptomatic RP attacks, comprising:
- a) obtaining daily number of the symptomatic RP attack episodes in the subject for 10 to 25 days prior to administering iloprost or a pharmaceutically acceptable change of the subject's fingers and at least one symptom of the fingers selected from pain, numbness, tingling, or discomfort;
- b) calculating a baseline average weekly frequency of the symptomatic RP attacks in the subject;
- c) administering iloprost or a pharmaceutically acceptable salt thereof by intravenous or subcutaneous injection at about 0.5 ng/kg/min to about 2.0 ng/kg/min for about 6 hours a day for 5 consecutive days;
- d) obtaining daily number of the symptomatic RP attack episodes in the subject for about 2 weeks to about 10 weeks after the administration of iloprost or a pharmaceutically acceptable salt thereof;
- e) calculating an average weekly frequency of the symptomatic RP attacks in the subject after the administration of iloprost or a pharmaceutically acceptable salt thereof; and
- f) comparing the baseline average frequency and the average weekly frequency of the symptomatic RP attacks.

The present disclosure provides methods of determining the effect of iloprost or a pharmaceutically acceptable salt thereof in a subject with systemic sclerosis experiencing symptomatic RP attacks, comprising:
- a) obtaining a total daily duration as a daily sum of duration of each symptomatic RP attack episodes in the subject for 10 to 25 days prior to administering iloprost or a pharmaceutically acceptable salt thereof, wherein one symptomatic RP attack episode comprises at least one color change of the subject's fingers and at least one symptom of the fingers selected from pain, numbness, tingling, or discomfort;
- b) calculating a baseline average weekly duration of the symptomatic RP attacks in the subject;
- c) administering iloprost or a pharmaceutically acceptable salt thereof by intravenous or subcutaneous injection at about 0.5 ng/kg/min to about 2.0 ng/kg/min for about 6 hours a day for 5 consecutive days;

d) obtaining a total daily duration as a daily sum of duration of each symptomatic RP attack episodes in the subject for about 2 weeks to about 10 weeks after the administration of iloprost or a pharmaceutically acceptable salt thereof;

e) calculating an average weekly duration of the symptomatic RP attacks in the subject after the administration of iloprost or a pharmaceutically acceptable salt thereof; and f) comparing the baseline average duration and the average weekly duration of the symptomatic RP attacks.

The present disclosure provides methods of determining the effect of iloprost or a pharmaceutically acceptable salt thereof in a subject with systemic sclerosis experiencing symptomatic RP attacks, comprising:

a) obtaining daily numeric severity rating score of each of the following symptoms of the fingers: pain, numbness, discomfort, and tingling, in the subject for 10 to 25 days prior to administering iloprost or a pharmaceutically acceptable salt thereof;

b) calculating a baseline weekly average severity score of each symptom for the subject;

c) selecting the symptom with the worst baseline weekly average severity score;

d) administering iloprost or a pharmaceutically acceptable salt thereof by intravenous or subcutaneous injection at about 0.5 ng/kg/min to about 2.0 ng/kg/min for about 6 hours a day for 5 consecutive days;

e) obtaining daily numeric severity rating score of the following symptoms of the fingers: pain, numbness, discomfort, and tingling, in the subject for about 2 weeks to about 10 weeks after the administration of iloprost or a pharmaceutically acceptable salt thereof;

f) calculating an average weekly severity score of each symptom in the subject; and g) comparing the baseline weekly average severity score and the weekly average severity score of the symptom determined in step c).

In embodiments of the methods of determining the effect of iloprost or a pharmaceutically acceptable salt thereof, in step a) and step e), the daily numeric severity rating score reflects the value of the worst symptom in a given day.

BRIEF DESCRIPTION OF THE DRAWINGS

FIG. 1 shows the treatment comparison of absolute change from baseline (treatment effect) in weekly frequency of attacks by date of randomization subgroups.

DETAILED DESCRIPTION

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "an IP receptor agonist" refers to one or more IP receptor agonists or at least one IP receptor agonist. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation The term "pharmaceutically acceptable salts" includes both acid and base addition salts. Pharmaceutically acceptable salts include those obtained by reacting the active compound functioning as an acid, with an inorganic or organic base to form a salt. Organic base includes, but are not limited to, monoethanolamine, diethanolamine, triethanolamine, trometamol and meglumine. Those skilled in the art will further recognize that base addition salts may be prepared by reaction of the compounds with the appropriate inorganic or organic base via any of a number of known methods.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The compound of the invention, or their pharmaceutically acceptable salts contain asymmetric centers and can thus give rise to enantiomers, diastereomers, and other stereoisomeric forms that can be defined, in terms of absolute stereochemistry, as (R) or(S). The present disclosure is meant to include all such possible isomers, as well as their racemic and optically pure forms whether or not they are specifically depicted herein. Stereoisomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). The compound described herein also contains an olefinic double bond, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes diastereomers.

Pharmaceutically Active Ingredient

The present disclosure relates to use of iloprost or a pharmaceutically acceptable salt thereof or a stereoisomer thereof for treating systemic sclerosis (SSc) with symptomatic Raynaud's Phenomenon (RP). Iloprost has the following structure and can also be identified as (5E)-5-[(3aS,4R,5R,6aS)-5-hydroxy-4-[(E,3S)-3-hydroxy-4-methyloct-1-en-6-ynyl]-3,3a,4,5,6,6a-hexahydro-1H-pentalen-2-ylidene]pentanoic acid.

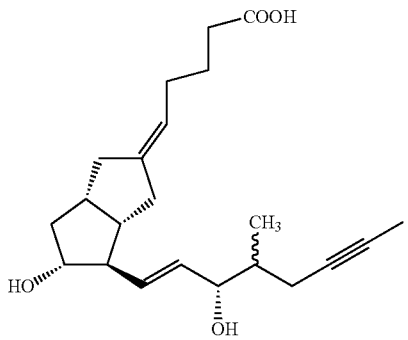 [SMILES: CC#CCC(C)[C@H](O)/C=C/[C@@H]1[C@H]2C/C(=C/CCCC(=O)O)C[C@H]2C[C@H]1O]

The present disclosure also relates to pharmaceutical composition comprising iloprost or a pharmaceutically acceptable salt thereof or a stereoisomer thereof.

Formulation for Injection

The present disclosure relates to administering iloprost or a pharmaceutically acceptable salt thereof or a stereoisomer thereof to a SSc patient with symptomatic RP. In embodiments, the iloprost or a pharmaceutically acceptable salt thereof or a stereoisomer thereof is administered by injection. In embodiments, administration is by intravenous or subcutaneous injection. In embodiments, administration is by continuous infusion. In embodiments, administration is by continuous infusion is intravenous infusion or subcutaneous infusion. In embodiments, administration is through peripheral catheter system, a peripheral inserted central catheter (PICC), or subcutaneous catheter in the abdomen. In embodiments, administration is through NovaCath Integrated IV Catheter System or a Poly Per-Q-Cath Catheter. In embodiments, the same peripheral catheter system or a peripheral inserted central catheter (PICC) is used for 1, 2, 3, 4, and/or 5 days of treatment. In embodiments, the same peripheral catheter system or a peripheral inserted central catheter (PICC) is used during all 5 days of treatment.

In embodiments of administering iloprost or a pharmaceutically acceptable salt thereof or a stereoisomer thereof to a SSc patient with symptomatic RP, the administration is done at a medical facility by a medically trained professional. In embodiments, the administration is done at a decentralized setting. In embodiments, the administration is done at the subject's home or ambulatory infusion suite. In embodiments of the administration at a decentralized setting, the administration of iloprost or a pharmaceutically acceptable salt thereof or a stereoisomer thereof is performed by a medically trained professional. In embodiments of the administration at a decentralized setting, a physician is accessible by telehealth during the treatment to assess adverse events and vital signs.

In embodiments of administering iloprost or a pharmaceutically acceptable salt thereof or a stereoisomer thereof to a SSc patient with symptomatic RP, the administration is temporarily interrupted if the patient experiences symptomatic hypotension, systolic blood pressure <80 mm HG, intolerable adverse events (e.g., vomiting), or a systolic blood pressure drop more than 10 mm Hg from the patient's pre-infusion measurement. In embodiments, when the patient's systolic blood pressure drops more than 10 mm Hg from the patient's pre-infusion measurement, a physician must determine if the infusion should be reinitiated. In embodiments, symptomatic hypotension is any reduction of blood pressure associated with symptoms (e.g., dizziness, lightheadedness, syncope). In embodiments where the treatment is temporarily interrupted, a physician determines whether to re-initiate treatment.

In embodiments, iloprost, or a pharmaceutically acceptable salt or a stereoisomer thereof, is formulated as a sterile solution. In embodiments, formulation comprising iloprost, or a pharmaceutically acceptable salt or a stereoisomer thereof, further comprises pharmaceutically acceptable excipients.

Pharmaceutically acceptable excipients include, but are not limited to, solubilizing agents, pH adjusting agents, tonicity agents, buffering agents, and/or solvents.

In embodiments, solubilizing agents is selected from pharmaceutically acceptable alcohols, glycols, esters, ethers, or silicones. In embodiments, the solubilizing agent is ethanol.

In embodiments, pH adjusting agents is a pharmaceutically acceptable acid or base. In embodiments, the pH adjusting agent is hydrochloric acid.

In embodiments, tonicity agents include, but are not limited to, glycerin, lactose, mannitol, dextrose, sodium chloride, sodium sulfate, and sorbitol. In embodiments, the tonicity agent is sodium chloride.

In embodiments, buffering agents include, but not limited to, citrate buffer, phosphate buffer, phosphate citrate buffer, bicarbonate buffer, tartrate buffer, acetate buffer, and trometamol buffer. In embodiments, the buffering agent is trometamol.

In embodiments, solvents are sterile solvents. In embodiments, solvents include, but are not limited to, water, glucose solution, dextrose solution, saline solution, Ringer's solution, and lactated Ringer's solution. In embodiments, the solvent is water.

In embodiments, formulation comprising iloprost, or a pharmaceutically acceptable salt or a stereoisomer thereof, further comprises trometamol, ethanol, sodium chloride, hydrochloric acid, and water.

In embodiments, formulation comprising iloprost, or a pharmaceutically acceptable salt or a stereoisomer thereof, contains no preservatives.

In embodiments, formulation comprising iloprost, or a pharmaceutically acceptable salt or a stereoisomer thereof, is provided as a single use vial. In embodiments, each vial comprises 100 mg iloprost per 1 mL. In embodiments, each single-use formulation comprises about 0.1 mg iloprost or a pharmaceutically acceptable salt or a stereoisomer thereof. In embodiments, each single-use formulation comprises about 0.1 mg iloprost or a pharmaceutically acceptable salt or a stereoisomer thereof, about 0.84 mg ethanol, about 0.242 mg tromethamine, about 9.0 mg sodium chloride, and about 0.51 mg of hydrochloric acid in water for injection to make 1 mL.

In embodiments, the single use vial containing iloprost is stored at room temperature (20° C. to 25° C.). In embodiments, the single use vial containing iloprost is stored at a temperature between about 20° C. to about 25° C. In embodiments, the single use vial containing iloprost is protected from light when stored. In embodiments, the single use vial contains 100 µg iloprost per 1 mL.

In embodiments, formulation comprising iloprost, or a pharmaceutically acceptable salt or a stereoisomer thereof, has a pH of about 8.0 to about 9.0.

In embodiments, formulation comprising iloprost, or a pharmaceutically acceptable salt or a stereoisomer thereof, is further diluted with a sterile solvent for injection or infusion. In embodiments, the formulation is further diluted with saline solution for injection or infusion. In embodiments, the formulation is further diluted with sodium chloride 0.9% injection, USP, for injection or infusion.

In embodiments, formulation comprising iloprost, or a pharmaceutically acceptable salt or a stereoisomer thereof, for injection or infusion is at a concentration of about 1,000 ng iloprost per 1 mL. In embodiments, 1 mL of 100 mg iloprost/mL formulation is diluted with 99 mL of 0.9% sodium chloride. In embodiments, 1 mL of 100 µg iloprost/mL is diluted with 99 mL of 0.9% sodium chloride injection (USP) to provide iloprost concentration of 1,000 ng/ml (1 µg/mL). In embodiments, diluted formulation is ready to use and can be used immediately, or stored at refrigerated temperatures (2° C. to 8° C.) for a maximum of 8 days prior to use, or stored at room temperature (20° C. to 25° C.) for 4 hours prior to administration as a 6-hour continuous infusion. In embodiments, continuous infusion is continuous intravenous infusion.

In embodiments, formulation comprising iloprost, or a pharmaceutically acceptable salt or a stereoisomer thereof, for injection or infusion is at a concentration of about 25 µg Iloprost per 1 mL. In embodiments, 25 µg Iloprost per 1 mL formulation is ready to use and can be used immediately, or stored at refrigerated temperatures (2° C. to 8° C.) for a maximum of 8 days prior to use, or stored at room temperature (20° C. to 25° C.) for 4 hours prior to administration as a 6-hour continuous infusion. In embodiments, continuous infusion is continuous subcutaneous infusion.

In embodiments, ready to use formulation comprising iloprost or a pharmaceutically acceptable salt or a stereoisomer thereof, as disclosed herein is safe, efficacious, and stable for up to 8 days at 2° C. to 8° C. The 8-day stability for the ready to use formulation is critical so that patients receive an accurate dose of iloprost or a pharmaceutically acceptable salt or a stereoisomer thereof and to minimize the risk of infection (sepsis or line-infection). In embodiments, the 8-day stability for the ready to use formulation is important in enabling decentralized infusions in the patient's home setting or at an off-site ambulatory infusion sites, which reduces the patients risk to nosocomial infections (contracting infection at a hospital or infusion center) and will improve patient convenience which reduces the risk of non-compliance.

In embodiments, a subcutaneous continuous infusion would use a more concentrated fully diluted ready to use iloprost product (e.g. 25 µg/mL instead of 1 µg/mL for intravenous infusion) but the dose delivered (ng/kg/min) and time of delivery (6 hours) would be equivalent.

Therapeutic Use

The present disclosure relates to methods for treating symptomatic digital ischemic episodes (symptomatic RP) in a systemic sclerosis (SSc) patient. Currently, there are no FDA-approved therapies available to improve symptoms in patients with SSc. Also, there are no formal guidelines available for evaluation and treatment of symptomatic digital ischemic episodes in a SSc patient. Available standard of care for SSc patients with symptomatic RP has several limitations and is mainly focused on nonpharmacological therapy, such as avoidance of cold temperatures, keeping whole body warm, and avoid smoking. Emotional stress alone can trigger worsening symptoms of RP. In addition, patients are instructed to avoid pharmacotherapy agents that can cause vasoconstriction (e.g. sympathomimetic drugs, clonidine, serotonin-receptor agonists). Oral vasodilator therapies are used; however, the evidence of efficacy and safety is lacking. Proximal sympathectomy can improve symptoms in some patients but the effects last less than one year and the procedure is costly and invasive. Thus, there is a need for an effective treatment of symptomatic RP in SSc patients.

The present disclosure relates to method for treatment of systemic sclerosis (SSc) to reduce the frequency of symptomatic digital ischemic episodes (symptomatic RP), comprising administering iloprost or a pharmaceutically acceptable salt thereof to a subject in need thereof.

The present disclosure also relates to method for treatment of SSc to reduce the severity of digital ischemic episodes (RP), comprising administering iloprost or a pharmaceutically acceptable salt thereof to a subject in need thereof.

The present disclosure also relates to method for treatment of SSe to reduce the frequency and severity of symptomatic digital ischemic episodes (symptomatic RP), comprising administering iloprost or a pharmaceutically acceptable salt thereof to a subject in need thereof.

The present disclosure also relates to administering iloprost or a pharmaceutically acceptable salt thereof or a stereoisomer thereof to a SSc patient with symptomatic RP by intravenous injection, subcutaneous injection, intravenous infusion, or subcutaneous infusion. In embodiments, administration is by continuous parenteral infusion.

In embodiments, an advantage of continuous parental infusion of iloprost or a pharmaceutically acceptable salt thereof or a stereoisomer thereof, is its greater bioavailability when compared to other routes of administration. For example, iloprost (a synthetic analog of prostacyclin, PGI2) has poor oral bioavailability and tolerability making oral administration route not viable.

In embodiments, another advantage of continuous parental infusion of iloprost or a pharmaceutically acceptable salt thereof or a stereoisomer thereof, is that the iloprost formulation disclosed herein for infusion is stable which allows for home infusion and decentralized infusions.

In embodiments, another advantage of continuous parental infusion of iloprost or a pharmaceutically acceptable salt thereof or a stereoisomer thereof, is the ability for iloprost to act as a potent prostacy clin (IP-) receptor agonist. In embodiments, iloprost or a pharmaceutically acceptable salt thereof or a stereoisomer thereof, increases cyclic AMP concentrations in pertinent cells thereby having an effect as vasodilator or as an anti-vasoconstrictor, anti-fibrotic, anti-platelet, and/or anti-inflammatory. In embodiments, once iloprost or a pharmaceutically acceptable salt thereof or a stereoisomer thereof, reaches the site of action (digit cutaneous circulation), the infusion therapy would reduce the frequency, symptoms and duration of symptomatic RP attacks in SSc patients by attenuating digital vasoconstrictive episodes, fibrosis, inflammation, and platelet activation.

In embodiments, iloprost or a pharmaceutically acceptable salt or stereoisomer thereof, is administered once a day for 3 to 7 days. In embodiments, iloprost or a pharmaceutically acceptable salt or stereoisomer thereof, is administered once a day for 5 days. In embodiments, iloprost or a pharmaceutically acceptable salt or stereoisomer thereof, is administered once a day for 5 consecutive days.

In embodiments, iloprost or a pharmaceutically acceptable salt or stereoisomer thereof, is administered once a day via intravenous injection or infusion over about 4 hours to about 8 hours. In embodiments, iloprost or a pharmaceutically acceptable salt or stereoisomer thereof, is administered once a day via intravenous injection or infusion over about 4 hours, about 5 hours, about 6 hours, about 7 hours, or about 8 hours. In embodiments, iloprost or a pharmaceutically acceptable salt or stereoisomer thereof, is administered once a day via intravenous injection or infusion over about 6 hours.

In embodiments, iloprost or a pharmaceutically acceptable salt or stereoisomer thereof, is administered at a rate or a dose in the range of about 0.3 to about 2.5 ng iloprost/kg body weight/min. In embodiments, iloprost or a pharmaceutically acceptable salt or stereoisomer thereof, is administered at a rate or a dose in the range of about 0.5 to about 2.0 ng/kg/min. In embodiments, the rate or the dose of injection or infusion can be adjusted by the administering medical professional at any time during the treatment.

In embodiments, the starting dose of iloprost or a pharmaceutically acceptable salt or stereoisomer thereof, is reduced in subjects with impaired liver function. In embodiments, the starting dose of iloprost or a pharmaceutically acceptable salt or stereoisomer thereof, is reduced in subjects with Child-Pugh Class B or Class C hepatic impairment. In embodiments, the starting dose of iloprost or a pharmaceutically acceptable salt or stereoisomer thereof, is reduced in subjects with impaired liver function to about 0.25 ng iloprost/kg body weight/min. In embodiments, the dose of iloprost or a pharmaceutically acceptable salt or stereoisomer thereof, is reduced in subjects with impaired liver function to a range of about 0.25 ng iloprost/kg body weight/min to about 1.0 ng/kg/min. In embodiments, the dose titration rate of iloprost or a pharmaceutically acceptable salt or stereoisomer thereof, is reduced in subjects with impaired liver function to about 0.25 ng/kg/min increments.

In embodiments, if the administration of iloprost or a pharmaceutically acceptable salt thereof or a stereoisomer thereof is stopped due to a dose-limiting adverse event, administration can be reinitiated at a previously tolerated rate or dose once the adverse event is resolved.

In embodiments, the administration of iloprost or a pharmaceutically acceptable salt thereof or a stereoisomer thereof follows the dose titration as disclosed in Table 1.

TABLE 1

Dose Titration

| Titration and Maintenance | Time Point | Dose | Instructions |
|---|---|---|---|
| Starting dose | 0 min; Day 1 | 0.5 ng/kg/min | If 0.5 ng/kg/min starting dose is not tolerated, discontinue and attempt to reinitiate the drug infusion when dose-limiting events subside. |
| Up-titration | 30 min; Day 1 | 1.0 ng/kg/min | Reduce the dose to 0.5 ng/kg/min (starting dose) if the 1.0 ng/kg/min dose is not tolerated. |
| | 60 min; Day 1 | 1.5 ng/kg/min | Reduce the dose to 1.0 ng/kg/min if the 1.5 ng/kg/min dose is not tolerated. |
| | 90 min; Day 1 | 2.0 ng/kg/min | Reduce the dose to 1.5 ng/kg/min if the 2.0 ng/kg/min dose is not tolerated. |
| | 120 min; Day 1 (Hours 2 to 6) | 2.0 ng/kg/min, or highest tolerated dose | Reduce dose in a stepwise manner if there are dose-limiting adverse events. |
| Maintenance | Days 2 to 5 | 2.0 ng/kg/min, or tolerated dose previous day | Administer the tolerated dose from the previous for the remaining days without up- or down-titration, unless the dose is not tolerated or adverse events occur that necessitate a reduction in dose (in 0.5 ng/kg/min increments). | or infusion is adjusted according to the subject's tolerability within the range of 0.5 to about 2.0 ng/kg/min.

In embodiments, the administration rate or dose is adjusted on the first day of treatment. In embodiments, on the first day of treatment, administration of iloprost or a pharmaceutically acceptable salt or stereoisomer thereof, is initiated at a rate or a dose of 0.5 ng/kg/min. In embodiments, the rate or the dose of administration is increased about every 30 minutes in increments of 0.5 ng/kg/min up to 2.0 ng/kg/min to determine the subject's tolerated dose. In embodiments, the second day of treatment and thereafter is initiated at the highest rate or dose tolerated by the subject on treatment day 1. In embodiments, the rate or the dose of In embodiments, iloprost or a pharmaceutically acceptable salt thereof or a stereoisomer thereof is administered at a concentration in the range of about 0.1 μg iloprost/mL. to about 100.0 μg iloprost/mL (100 ng/mL to 100,000 ng/ml). In embodiments, iloprost or a pharmaceutically acceptable salt thereof or a stereoisomer thereof is administered at a concentration in the range of about 500 ng iloprost/mL to about 2,500 ng iloprost/mL, including all values and subranges therebetween. In embodiments, iloprost or a pharmaceutically acceptable salt thereof or a stereoisomer thereof is administered at a concentration in the range of about 750 ng iloprost/mL to about 1,500 ng iloprost/mL, including all values and subranges therebetween. In embodiments, iloprost or a pharmaceutically acceptable salt thereof or a stereoisomer thereof is administered at a concentration in the range of about 900 ng iloprost/mL to about 1,250 ng iloprost/mL, including all values and subranges therebetween. In embodiments, iloprost or a pharmaceutically acceptable salt thereof or a stereoisomer thereof is administered at a concentration of about 1,000 ng iloprost/mL.

In embodiments, iloprost or a pharmaceutically acceptable salt thereof or a stereoisomer thereof is administered to a SSc subject with symptomatic RP who experiences symptomatic RP attacks, on average, at least 3 days/week. In embodiments, one episode of symptomatic RP attack comprises (i) at least one color change of the subject's fingers (blue, purple, white, or red) and (ii) at least one symptom of the fingers selected from pain, numbness, tingling, or discomfort. In one embodiment, an episode of symptomatic RP attack is over when the color of the subject's fingers returns to the color pre-RP attack and the symptoms return to the subject's pre-RP attack level.

In embodiments, iloprost or a pharmaceutically acceptable salt thereof or a stereoisomer thereof is administered to a SSe subject through a peripheral line or peripherally inserted central catheter using an infusion pump. In embodiments of infusion administration, in-line 0.22 micron filter is used. In embodiments of infusion administration, infusion pump should be able to deliver rates between 0.1 to 99.99 mL per hour. In embodiments of infusion administration, infusion pump should be able to adjust infusion rates with increments of 0.1 mL per hour. In embodiments of infusion administration, infusion pump should be accurate to 5.0% of programmed rate. In embodiments of infusion administration, infusion pump should be positive pressure-driven (continuous or pulsatile). In embodiments, the reservoir or the infusion line set comprise polytetrafluoroethylene, fluorinated ethylenepropylene, polyvinylidene fluoride, polyether urethanes, polycarbonate urethanes, urethanes, polyurethanes, polyolefins, polyethylene, polypropylene, ethylene polymers, ethylene vinyl acetate, ethylene coacrylic acid, ethylene covinyl alcohol, polyimide, polyetheretherketone, polyaryletherketone, polysulfone, parylene, parylast, polyethlyene terephthalate, polyethylene oxide, silicones, polyesters; polyolefins, polyamides, polycaprolactams, polyvinyl chloride, polyacrylates, polymethacrylates; polyureas, polyvinylbalides, polyvinylidenehalides, polyvinylethers, poly vinylaromatics, poly vinylesters, alkyd resins, polysiloxanes, epoxy resins, polyvinyl methyl ether, polyvinyl alcohol, acrylic polymers and copolymers, polyacrylonitriles, polystyrene copolymers of vinyl monomers with olefins, styrene acrylonitrile copolymers, ethylene methyl methacrylate copolymers, ethylene vinyl acetate, polyethers, rayons, cellulosics, cellulose acetate; cellulose nitrate, cellulose propionate, or any derivatives, analogs, homologues, salts, copolymers or combinations thereof. In embodiments, the reservoir or the infusion line set can be made of polyvinyl chloride, polypropylene, silicone, ethyl vinyl acetate, copolyester ether, polyolefins, or the like, or combinations thereof. In embodiments, the reservoir and infusion line set can be made of polyvinyl chloride.

In embodiments of infusion administration of 1,000 ng/mL iloprost or a pharmaceutically acceptable salt thereof or a stereoisomer thereof, the infusion rate of Table 2 can be used according to the subject's body weight.

TABLE 2

Infusion rates for iloprost at a concentration of 1,000 ng iloprost per 1 mL

| Patient Weight | Study Drug Intravenous Infusion Pump Rate (mL/hr) | | | |
|---|---|---|---|---|
| | 0.5 ng/kg/min (Starting Dose) | 1.0 ng/kg/min | 1.5 ng/kg/min | 2.0 ng/kg/min |
| 30 to 39.9 kg | 0.9 | 1.8 | 2.7 | 3.6 |
| 40 to 49.9 kg | 1.2 | 2.4 | 3.6 | 4.8 |
| 50 to 59.9 kg | 1.5 | 3.0 | 4.5 | 6.0 |
| 60 to 69.9 kg | 1.8 | 3.6 | 5.4 | 7.2 |
| 70 to 79.9 kg | 2.1 | 4.2 | 6.3 | 8.4 |
| 80 to 89.9 kg | 2.4 | 4.8 | 7.2 | 9.6 |
| 90 to 99.9 kg | 2.7 | 5.4 | 8.1 | 10.8 |
| 100 to 109.9 kg | 3.0 | 6.0 | 9.0 | 12.0 |
| 110 to 119.9 kg | 3.3 | 6.6 | 9.9 | 13.2 |
| 120 to 129.9 kg | 3.6 | 7.2 | 10.8 | 14.4 |

In embodiments, the subject keeps a RP diary to record the frequency, duration, intensity or severity of each symptom, and/or the symptomatic RP attack's impact on the quality of subject's life. In one embodiment, the subject keeps a RP diary before and after the iloprost treatment. In embodiments, the RP diary (a patient-reported outcome; PRO) kept by the patient is useful in assessing the effectiveness of iloprost treatment. In embodiments, the RP diary is maintained electronically (ePRO).

In embodiments, the subject records the number (frequency) of symptomatic RP attacks in a day in the RP diary.

In embodiments, the subject records the duration of each symptomatic RP attack in a day in the RP diary.

In embodiments, the subject records the intensity (severity) of the pain in the fingers associated with symptomatic RP attacks in a given day as a numeric score in the RP diary. In embodiments, the score associated with pain recorded in the RP diary is the score of the worst pain the subject experienced in a given day. In embodiments, the numeric rating score is on a scale of 0 to 10, where 0 is no pain and 10 is severe pain.

In embodiments, the subject records the intensity (severity) of the numbness in the fingers associated with symptomatic RP attacks in a given day as a numeric score in the RP diary. In embodiments, the score associated with numbness recorded in the RP diary is the score of the worst numbness the subject experienced in a given day. In embodiments, the numeric rating score is on a scale of 0 to 10, where 0 is no numbness and 10 is severe numbness.

In embodiments, the subject records the intensity (severity) of the tingling in the fingers associated with symptomatic RP attacks in a given day as a numeric score in the RP diary. In embodiments, the score associated with tingling recorded in the RP diary is the score of the worst tingling the subject experienced in a given day. In embodiments, the numeric rating score is on a scale of 0 to 10, where 0 is no tingling and 10 is severe tingling.

In embodiments, the subject records the intensity (severity) of the discomfort in the fingers associated with symptomatic RP attacks in a given day as a numeric score in the RP diary. In embodiments, the score associated with discomfort recorded in the RP diary is the score of the worst discomfort the subject experienced in a given day. In embodiments, the numeric rating score is on a scale of 0 to 10, where 0 is no discomfort and 10 is severe discomfort.

The present disclosure also relates to reducing the weekly average frequency of symptomatic RP attacks from baseline in a SSc subject experiencing symptomatic attacks, comprising administering iloprost or a pharmaceutically acceptable salt thereof or a stereoisomer thereof. In embodiments, iloprost or a pharmaceutically acceptable salt thereof or a stereoisomer thereof is administered in any method as disclosed herein. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

In embodiments, the weekly average frequency of symptomatic RP attacks is determined according to the subject's RP diary. The baseline weekly average frequency of symptomatic RP attacks is the weekly average of the number of symptomatic RP attack episodes in the subject before iloprost treatment. In embodiments, the baseline weekly average frequency is based on the subject's RP diary reporting daily symptomatic RP attack frequency for 5 to 30 days prior to the iloprost treatment. In embodiments, the baseline weekly average frequency is based on the subject's symptomatic RP diary reporting daily symptomatic RP attack frequency for 10 to 25 days prior to the iloprost treatment.

In embodiments, the weekly average frequency of symptomatic RP attacks after iloprost treatment is the weekly average of the number of symptomatic RP attack episodes in the subject after iloprost treatment. In embodiments, the weekly average frequency after iloprost treatment is based on the subject's RP diary reporting daily symptomatic RP attack frequency for at least 5 days after to the iloprost treatment. The subject can report the frequency of the daily symptomatic RP attacks at different times after the iloprost treatment, such as recording for at least 5 days directly following the treatment (week 1 after treatment) and/or recording for at least 5 days, 5 weeks after treatment. In embodiments, the subject reports the frequency of the daily symptomatic RP attacks from about 1 week to about 15 weeks after treatment, including all values therebetween. In embodiments, the subject reports the frequency of the daily symptomatic RP attacks from about 3 weeks to about 12 weeks after treatment, including all values therebetween. In embodiments, the subject reports the frequency of the daily symptomatic RP attacks up to about 9 weeks or up to about 12 weeks after treatment.

In embodiments, the weekly average frequency of symptomatic RP attacks is reduced by about 10% to about 90% from the baseline weekly average frequency, including all values therebetween. In embodiments, the weekly average frequency of symptomatic RP attacks is reduced by about 15% to about 60% from the baseline weekly average frequency, including all values therebetween. In embodiments, the weekly average frequency of symptomatic RP attacks is reduced by about 25% to about 55% from the baseline weekly average frequency, including all values therebetween. In embodiments, the weekly average frequency of symptomatic RP attacks is reduced by about 30% to about 50% from the baseline weekly average frequency, including all values therebetween. In embodiments, the weekly average frequency of symptomatic RP attacks is reduced by about 5%, about 10%, about 15%, about 20%, about 25%, about 30%, about 35%, about 40%, about 45%, about 50%, about 55%, about 60%, about 65%, or about 70% from the baseline weekly average frequency, including any values therebetween. In embodiments, the weekly average frequency of symptomatic RP attacks is reduced by at least about 5%, about 10%, about 15%, about 20%, about 25%, about 30%, about 35%, about 40%, about 45%, or about 50% from the baseline weekly average frequency, including any values therebetween. In embodiments, the weekly average frequency of symptomatic RP attacks is reduced by at least about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% from the baseline weekly average frequency, including any values therebetween. In one embodiment, the weekly average frequency reduction is provided as a mean reduction value for a SSc population treated with iloprost or a pharmaceutically acceptable salt thereof.

In embodiments, a treatment effect of iloprost or a pharmaceutically acceptable salt thereof on the weekly average frequency of symptomatic RP attacks is about −2.0 to about −30.0, including all values and subranges therebetween. In embodiments, a treatment effect of iloprost or a pharmaceutically acceptable salt thereof on the weekly average frequency of symptomatic RP attacks is about −2.0 to about −15.0, including all values and subranges therebetween. In embodiments, a treatment effect of iloprost or a pharmaceutically acceptable salt thereof on the weekly average frequency of symptomatic RP attacks is about −3.0 to about −10.0, including all values and subranges therebetween. In embodiments, a treatment effect of iloprost or a pharmaceutically acceptable salt thereof on the weekly average frequency of symptomatic RP attacks is about −3.0 to about −8.0, including all values and subranges therebetween. In embodiments, a treatment effect of iloprost or a pharmaceutically acceptable salt thereof on the weekly average frequency of symptomatic RP attacks is at least about −3.0, about −3.5, about −4.0, about −4.5, about −5.0, about −5.5, about −6.0, about −6.5, about −7.0, about −7.5, about −8.0, about −8.5, about −9.0, about −9.5, or about −10.0, including all values therebetween. A treatment effect is the change in the weekly average frequency of symptomatic RP attacks from baseline to end of efficacy follow-up. The primary analysis on this endpoint is performed based on an analysis of covariance (ANCOVA) model, including randomized treatment group and randomized stratification (i.e., use of phosphodiesterase inhibitors at screening) as factors and baseline weekly RP attacks as a covariate. The treatment comparisons (iloprost vs placebo) will be estimated together with the 95% confidence interval and p-value. For example, if the subject who received iloprost treatment and the subject who received placebo both had a baseline weekly average frequency of 30.0 attacks per week and the weekly average frequency of the subject who received iloprost reduced to 19.5 attacks and the subject who received placebo reduced to 25.0 attacks, then the treatment effect is −5.5 (in real life situations, the baseline values of iloprost and placebo groups would be expected to be different but the above example uses the same value for ease of explanation). The treatment effects are placebo corrected.

In embodiments, the weekly average frequency of symptomatic RP attacks is reduced for a period of about 1 week to about 6 months after one iloprost treatment (e.g., 5 days of infusion), including any values therebetween. In embodiments, the weekly average frequency of symptomatic RP attacks is reduced for a period of about 2 weeks to about 3 months after one iloprost treatment, including any values therebetween. In embodiments, the weekly average frequency of symptomatic RP attacks is reduced for a period of about 2 weeks to about 15 weeks after one iloprost treatment, including any values therebetween. In embodiments, the weekly average frequency of symptomatic RP attacks is reduced for a period of about 3 weeks to about 8 weeks after one iloprost treatment, including any values therebetween. In embodiments, the weekly average frequency of symptomatic RP attacks is reduced for a period of at least 2 week, 3 weeks, 4 weeks, 5 weeks, 6 weeks, 7 weeks, 8 weeks, 9 weeks, 10 weeks, 11 weeks, or 12 weeks after one iloprost treatment, including any values therebetween. In embodiments, the weekly average frequency of symptomatic RP attacks is reduced for a period of about 7 weeks, about 8 weeks, about 9 weeks, or about 10 weeks after one iloprost treatment, including any values therebetween.

The present disclosure also relates to methods of determining the effect of iloprost or a pharmaceutically acceptable salt thereof in a subject with systemic sclerosis experiencing symptomatic RP attacks, comprising the steps of:
a) obtaining daily number of the symptomatic RP attack episodes in the subject for 10 to 25 days prior to administering iloprost or a pharmaceutically acceptable change of the subject's fingers and at least one symptom of the fingers selected from pain, numbness, tingling, or discomfort;
b) calculating a baseline average weekly frequency of the symptomatic RP attacks in the subject;
c) administering iloprost or a pharmaceutically acceptable salt thereof by intravenous or subcutaneous injection at a dose of about 0.5 ng/kg/min to about 2.0 ng/kg/min for about 6 hours a day for 5 consecutive days;
d) obtaining daily number of the symptomatic RP attack episodes in the subject for about 2 weeks to about 10 weeks after the administration of iloprost or a pharmaceutically acceptable salt thereof;
e) calculating an average weekly frequency of the symptomatic RP attacks in the subject after the administration of iloprost or a pharmaceutically acceptable salt thereof; and
f) comparing the baseline average frequency and the average weekly frequency of the symptomatic RP attacks.

In embodiments of the methods of determining the effect of iloprost as discussed herein, the color change of the subject's fingers in step a) is color change to blue, purple, white, or red.

In embodiments of the methods of determining the effect of iloprost as discussed herein, the daily number of symptomatic RP attack episodes are reported by the subject in step a). In embodiments of the methods of determining the effect of iloprost as discussed herein, the daily number of symptomatic RP attack episodes are reported by the subject in step d).

In embodiments of the methods of determining the effect of iloprost as discussed herein, the amount of time in step d) for obtaining daily number of the symptomatic RP attack episodes in the subject after the administration of iloprost or a pharmaceutically acceptable salt thereof can range from 1 day to about 12 weeks after the treatment. In embodiments, the effect of iloprost can be determined from obtaining daily number of the symptomatic RP attack episodes in the subject after the administration of iloprost or a pharmaceutically acceptable salt thereof from about 1 day to about 1 week, from about 1 day to about 2 weeks, from about 1 day to about 3 weeks, or from about 1 day to about 4 weeks after the treatment.

In embodiments of the methods of determining the effect of iloprost as discussed herein, the iloprost treatment is effective when the average weekly frequency of the symptomatic RP attacks after the administration of iloprost or a pharmaceutically acceptable salt thereof in step e) is lower than the baseline average weekly frequency of the symptomatic RP attacks in step b) of the subject.

In embodiments of the methods of determining the effect of iloprost as discussed herein, step c) of administering iloprost or a pharmaceutically acceptable salt thereof can be replaced by any of the methods disclosed herein. In embodiments, step c) is by infusion.

The present disclosure also relates to reducing the weekly average duration of symptomatic RP attacks from baseline in a SSc subject experiencing symptomatic attacks, comprising administering iloprost or a pharmaceutically acceptable salt thereof or a stereoisomer thereof. In embodiments, iloprost or a pharmaceutically acceptable salt thereof or a stereoisomer thereof is administered in any method as disclosed herein. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

In embodiments, the weekly average duration of symptomatic RP attacks is determined according to the subject's RP diary. The baseline weekly average duration of symptomatic RP attacks is the weekly average of the total duration of all symptomatic RP attack episodes in the subject before iloprost treatment. In embodiments, the baseline weekly average duration is based on the subject's RP diary reporting daily symptomatic RP attack duration for each symptomatic RP attack episode for 5 to 30 days prior to the iloprost treatment. In embodiments, the baseline weekly average duration is based on the subject's RP diary reporting daily symptomatic RP attack duration for each symptomatic RP attack episode for 10 to 25 days prior to the iloprost treatment.

In embodiments, the weekly average duration of symptomatic RP attacks after iloprost treatment is the weekly average of the total duration of all symptomatic RP attack episodes in the subject after iloprost treatment. In embodiments, the weekly average duration after iloprost treatment is based on the subject's RP diary reporting daily symptomatic RP attack duration for each symptomatic RP attack episode for at least 5 days after to the iloprost treatment. The subject can report daily symptomatic RP attack duration for each symptomatic RP attack episode at different times after the iloprost treatment, such as recording for at least 5 days directly following the treatment (week 1 after treatment) and/or recording for at least 5 days, 6 weeks after treatment. In embodiments, the subject reports the duration of each symptomatic RP attack episode from about 1 week to about 15 weeks after treatment, including all values therebetween.

In embodiments, the subject reports the duration of each symptomatic RP attack episode from about 3 weeks to about 12 weeks after treatment, including all values therebetween. In embodiments, the subject reports the duration of each symptomatic RP attack episode up to about 9 weeks or up to about 12 weeks after treatment.

In embodiments, the weekly average duration of symptomatic RP attacks is reduced by about 10% to about 90% from the baseline weekly average duration, including all values therebetween. In embodiments, the weekly average duration of symptomatic RP attacks is reduced by about 15% to about 60% from the baseline weekly average duration, including all values therebetween. In embodiments, the weekly average duration of symptomatic RP attacks is reduced by about 15% to about 55% from the baseline weekly average duration, including all values therebetween. In embodiments, the weekly average duration of symptomatic RP attacks is reduced by about 5%, about 10%, about 15%, about 20%, about 25%, about 30%, about 35%, about 40%, about 45%, about 50%, about 55%, about 60%, about 65%, or about 70% from the baseline weekly average duration, including any values therebetween. In embodiments, the weekly average duration of symptomatic RP attacks is reduced by at least about 5%, about 10%, about 15%, about 20%, about 25%, about 30%, about 35%, about 40%, about 45%, or about 50% from the baseline weekly average duration, including any values therebetween. In embodiments, the weekly average duration of symptomatic RP attacks is reduced by at least about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% from the baseline weekly average duration, including any values therebetween. In one embodiment, the weekly average duration reduction is provided as a mean % reduction value for a SSc population treated with iloprost or a pharmaceutically acceptable salt thereof.

In embodiments, the weekly average duration of symptomatic RP attacks is reduced by about 30 minutes to about 2000 minutes, including all values and subranges therebetween. In embodiments, the weekly average duration of symptomatic RP attacks is reduced by about 30 minutes to about 1000 minutes, including all values and subranges therebetween. In embodiments, the weekly average duration of symptomatic RP attacks is reduced by about 30 minutes to about 500 minutes, including all values and subranges therebetween. In embodiments, the weekly average duration of symptomatic RP attacks is reduced by about 45 minutes to about 400 minutes, including all values and subranges therebetween. In embodiments, the weekly average duration of symptomatic RP attacks is reduced by about 45 minutes to about 300 minutes, including all values and subranges therebetween. In embodiments, the weekly average duration of symptomatic RP attacks is reduced by about 60 minutes to about 250 minutes, including all values and subranges therebetween. In embodiments, the weekly average duration of symptomatic RP attacks is reduced by at least about 30 minutes, about 45 minutes, about 60 minutes, about 75 minutes, about 90 minutes, about 105 minutes, about 120 minutes, about 135 minutes, about 150 minutes, about 165 minutes, about 180 minutes, about 195 minutes, about 210 minutes, about 225 minutes, about 240 minutes, about 250 minutes, about 265 minutes, about 285 minutes, or about 300 minutes, including all values therebetween. In one embodiment, the weekly average duration reduction is provided as a mean value in minutes for a SSc population treated with iloprost or a pharmaceutically acceptable salt thereof.

In embodiments, the mean reduction of weekly average duration of symptomatic RP attacks in a SSc population is by about 30 minutes to about 500 minutes, including all values and subranges therebetween.

In embodiments, a treatment effect of iloprost or a pharmaceutically acceptable salt thereof on the weekly average duration of symptomatic RP attacks is about −30 minutes to about −2000 minutes, including all values and subranges therebetween. In embodiments, a treatment effect of iloprost or a pharmaceutically acceptable salt thereof on the weekly average duration of symptomatic RP attacks is about −30 minutes to about −1000 minutes, including all values and subranges therebetween. In embodiments, a treatment effect of iloprost or a pharmaceutically acceptable salt thereof on the weekly average duration of symptomatic RP attacks is about −30 minutes to about −500 minutes, including all values and subranges therebetween. In embodiments, a treatment effect of iloprost or a pharmaceutically acceptable salt thereof on the weekly average duration of symptomatic RP attacks is about −45 minutes to about −400 minutes, including all values and subranges therebetween. In embodiments, a treatment effect of iloprost or a pharmaceutically acceptable salt thereof on the weekly average duration of symptomatic RP attacks is about −45 minutes to about −300 minutes, including all values and subranges therebetween. In embodiments, a treatment effect of iloprost or a pharmaceutically acceptable salt thereof on the weekly average duration of symptomatic RP attacks is about −60 minutes to about −150 minutes, including all values and subranges therebetween. In embodiments, a treatment effect of iloprost or a pharmaceutically acceptable salt thereof on the weekly average duration of symptomatic RP attacks is at least about −30 minutes, about −45 minutes, about −60 minutes, about −75 minutes, about −90 minutes, about −105 minutes, about −120 minutes, about −135 minutes, about −150 minutes, about −165 minutes, about −180 minutes, about −195 minutes, about −210 minutes, about −225 minutes, about −240 minutes, about −250 minutes, about −265 minutes, about −285 minutes, or about −300 minutes, including all values therebetween. A treatment effect is the change in the weekly average duration of symptomatic RP attacks from baseline to end of efficacy follow-up. The primary analysis on this endpoint is performed based on an analysis of covariance (ANCOVA) model, including randomized treatment group and randomized stratification (i.e., use of phosphodiesterase inhibitors at screening) as factors and baseline weekly RP attacks as a covariate. The treatment comparisons (iloprost vs placebo) will be estimated together with the 95% confidence interval and p-value. For example, if the subject who received iloprost treatment and the subject who received placebo both had a baseline weekly average duration of 350 minutes per week and the subject who received placebo reduced to 450 minutes per week, then the treatment effect is −100 minutes.

In embodiments, a mean treatment effect of iloprost or a pharmaceutically acceptable salt thereof on the weekly average duration of symptomatic RP attacks in a SSc population is about −30 minutes to about −500 minutes, including all values and subranges therebetween.

In embodiments, the weekly average duration of symptomatic RP attacks is reduced for a period of about 1 week to about 6 months after one iloprost treatment (e.g., 5 days of infusion), including any values therebetween. In embodiments, the weekly average duration of symptomatic RP attacks is reduced for a period of about 2 weeks to about 3 months after one iloprost treatment, including any values therebetween. In embodiments, the weekly average duration of symptomatic RP attacks is reduced for a period of about 3 weeks to about 15 weeks after one iloprost treatment, including any values therebetween. In embodiments, the weekly average duration of symptomatic RP attacks is reduced for a period of about 2 weeks to about 8 weeks after one iloprost treatment, including any values therebetween. In embodiments, the weekly average duration of symptomatic RP attacks is reduced for a period of at least 2 week, 3 weeks, 4 weeks, 5 weeks, 6 weeks, 7 weeks, 8 weeks, 9 weeks, 10 weeks, 11 weeks, or 12 weeks after one iloprost treatment, including any values therebetween. In embodiments, the weekly average duration of symptomatic RP attacks is reduced for a period of about 7 weeks, about 8 weeks, about 9 weeks, or about 10 weeks after one iloprost treatment, including any values therebetween.

The present disclosure also relates to methods of determining the effect of iloprost or a pharmaceutically acceptable salt thereof in a subject with systemic sclerosis experiencing symptomatic RP attacks, comprising the steps of:
a) obtaining a total daily duration as a daily sum of the duration of each symptomatic RP attack episodes in the subject for 10 to 25 days prior to administering iloprost or a pharmaceutically acceptable salt thereof, wherein one symptomatic RP attack episode comprises at least one color change of the subject's fingers and at least one symptom of the fingers selected from pain, numbness, tingling, or discomfort;
b) calculating a baseline average weekly duration of the symptomatic RP attacks in the subject;
c) administering iloprost or a pharmaceutically acceptable salt thereof by intravenous or subcutaneous injection at about 0.5 ng/kg/min to about 2.0 ng/kg/min for about 6 hours a day for 5 consecutive days;
d) obtaining a total daily duration as a daily sum of the duration of each symptomatic RP attack episodes in the subject for about 2 weeks to about 10 weeks after the administration of iloprost or a pharmaceutically acceptable salt thereof;
e) calculating an average weekly duration of the symptomatic RP attacks in the subject after the administration of iloprost or a pharmaceutically acceptable sat thereof; and
f) comparing the baseline average duration and the average weekly duration of the symptomatic RP attacks.

In embodiments of the methods of determining the effect of iloprost as discussed herein, the color change of the subject's fingers in step a) is color change to blue, purple, white, or red.

In embodiments of the methods of determining the effect of iloprost as discussed herein, the daily sum of the duration of each symptomatic RP attack episodes are reported by the subject in step a). In embodiments of the methods of determining the effect of iloprost as discussed herein, the daily sum of the duration of each symptomatic RP attack episodes are reported by the subject in step d).

In embodiments of the methods of determining the effect of iloprost as discussed herein, the amount of time in step d) for obtaining daily number of the symptomatic RP attack episodes in the subject after the administration of iloprost or a pharmaceutically acceptable salt thereof can range from 1 day to about 12 weeks after the treatment. In embodiments, the effect of iloprost can be determined from obtaining daily number of the symptomatic RP attack episodes in the subject after the administration of iloprost or a pharmaceutically acceptable salt thereof from about 1 day to about 1 week, from about 1 day to about 2 weeks, from about 1 day to about 3 weeks, or from about 1 day to about 4 weeks after the treatment.

In embodiments of the methods of determining the effect of iloprost as discussed herein, the iloprost treatment is effective when the average weekly duration of the symptomatic RP attacks after the administration of iloprost or a pharmaceutically acceptable salt thereof in step e) is lower than the baseline average weekly duration of the symptomatic RP attacks in step b) of the subject.

In embodiments of the methods of determining the effect of iloprost as discussed herein, step c) of administering iloprost or a pharmaceutically acceptable salt thereof can be replaced by any of the methods disclosed herein. In embodiments, step c) is by infusion.

The present disclosure also relates to reducing the weekly average severity of symptomatic RP attacks from baseline in a SSc subject experiencing symptomatic attacks, comprising administering iloprost or a pharmaceutically acceptable salt thereof or a stereoisomer thereof. In embodiments, iloprost or a pharmaceutically acceptable salt thereof or a stereoisomer thereof is administered in any method as disclosed herein. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

In embodiments, the severity of symptomatic RP attacks is measured by a symptom of the fingers with a worst baseline weekly average score selected from pain, numbness, discomfort, or tingling, based on a numeric rating scale (severity score). In embodiments, the symptomatic RP attacks is measured by pain, numbness, tingling and discomfort in the fingers. In embodiments, the severity is measured by different symptom based on what the subject reports as the worst symptom before iloprost treatment. In embodiments, if the baseline weekly average severity score is the same value for two symptoms of the fingers, the baseline weekly average will be based on the following order of rank: pain>numbness>tingling>discomfort.

In embodiments, the measuring the severity of symptomatic RP attacks by the subject's worst symptoms of pain, numbness, discomfort, or tingling, allows for some individualized measurement because every subject experiences symptomatic RP attacks differently. By focusing on the subject's worst symptoms, in embodiments, a subject's progress or status in his or her symptomatic RP attacks can be monitored better than asking the subject to give one severity score considering all the symptoms he or she experienced in a particular day.

In embodiments, the weekly average severity of symptomatic RP attacks is determined according to the subject's RP diary. The baseline weekly average severity of symptomatic RP attacks is the weekly average of the severity score of a symptom of symptomatic RP attack episodes in the subject before iloprost treatment. In embodiments, the baseline weekly average severity is based on the subject's RP diary reporting daily severity score for each symptom of the fingers during symptomatic RP attacks (pain, numbness, tingling, and discomfort) for 5 to 30 days prior to the iloprost treatment. In embodiments, the baseline weekly average severity is based on the subject's RP diary reporting daily severity score for each symptom of the fingers during symptomatic RP attacks for 10 to 25 days prior to the iloprost treatment.

In embodiments, the weekly average severity of symptomatic RP attacks after iloprost treatment is the weekly average of the severity score of a symptom of symptomatic RP attack episodes in the subject after iloprost treatment. In embodiments, the weekly average severity after iloprost treatment is based on the subject's RP diary reporting daily severity score for each symptoms of the fingers for at least 5 days after to the iloprost treatment. The subject can report daily symptomatic RP attack severity score for each symptom of the fingers at different times after the iloprost treatment, such as recording for at least 5 days directly following the treatment (week 1 after treatment) and/or recording for at least 5 days, 7 weeks after treatment. In embodiments, the subject reports the symptomatic RP attack severity score for each symptom of the fingers from about 1 week to about 15 weeks after treatment, including all values therebetween. In embodiments, the subject reports the symptomatic RP attack severity score for each symptom of the fingers from about 3 weeks to about 12 weeks after treatment, including all values therebetween. In embodiments, the subject reports the symptomatic RP attack severity score for each symptom of the fingers up to about 9 weeks or up to about 12 weeks after treatment.

In embodiments, when assessing whether the iloprost treatment resulted in reduction of the weekly average severity of the symptomatic RP attacks, the weekly average of the symptom determined to be the worst in the subject is compared to the weekly average severity score for the same symptom after iloprost treatment. That is, if a subject reported pain as the worst symptom prior to iloprost treatment (i.e., pain had the highest severity score baseline weekly average compared to numbness, tingling, or discomfort), then the subject's weekly average of pain severity scores after iloprost treatment will be compared to the baseline weekly average severity score for pain. This method allows individualization of outcome measurements as different subject experience the symptomatic RP attack symptoms in different degrees.

In embodiments, the weekly average severity score of symptomatic RP attacks is reduced by about 10% to about 90% from the baseline weekly average severity score, including all values therebetween. In embodiments, the weekly average severity score of symptomatic RP attacks is reduced by about 15% to about 60% from the baseline weekly average severity score, including all values therebetween. In embodiments, the weekly average severity score of symptomatic RP attacks is reduced by about 20% to about 50% from the baseline weekly average severity score, including all values therebetween. In embodiments, the weekly average severity score of symptomatic RP attacks is reduced by about 5%, about 10%, about 15%, about 20%, about 25%, about 30%, about 35%, about 40%, about 45%, about 50%, about 55%, about 60%, about 65%, or about 70%, from the baseline weekly average severity score, including all values therebetween. In embodiments, the weekly average severity score of symptomatic RP attacks is reduced by at least about 5%, about 10%, about 15%, about 20%, about 25%, about 30%, about 35%, about 40%, about 45%, or about 50% from the baseline weekly average severity score, including all values therebetween. In embodiments, the weekly average duration of symptomatic RP attacks is reduced by at least about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% from the baseline weekly average severity score, including any values therebetween. In one embodiment, the weekly average severity score reduction is provided as a mean % reduction value for a SSc population treated with iloprost or a pharmaceutically acceptable salt thereof.

In embodiments, the weekly average severity score of symptomatic RP attacks is reduced by a number in the range of about 0.2 to about 5.0 from the baseline weekly average severity score, wherein the severity score is based on 0 to 10 numeric rating scale. In embodiments, the weekly average severity score of symptomatic RP attacks is reduced by a number in the range of about 0.3 to about 4.0 from the baseline weekly average severity score, wherein the severity score is based on 0 to 10 numeric rating scale. In embodiments, the weekly average severity score of symptomatic RP attacks is reduced by a number in the range of about 0.5 to about 3.0 from the baseline weekly average severity score, wherein the severity score is based on 0 to 10 numeric rating scale. In embodiments, the weekly average severity score of symptomatic RP attacks is reduced by a number in the range of about 0.5 to about 3.0 from the baseline weekly average severity score, wherein the severity score is based on 0 to 10 numeric rating scale. In embodiments, the weekly average severity score of symptomatic RP attacks is reduced by a number in the range of about 0.5 to about 2.0 from the baseline weekly average severity score, wherein the severity score is based on 0 to 10 numeric rating scale. In embodiments, the weekly average severity score of symptomatic RP attacks is reduced by a number in the range of about 0.5 to about 1.5 from the baseline weekly average severity score, wherein the severity score is based on 0 to 10 numeric rating scale. In embodiments, the weekly average severity score of symptomatic RP attacks is reduced by a number in the range of about 0.6 to about 1.3 from the baseline weekly average severity score, wherein the severity score is based on 0 to 10 numeric rating scale. In embodiments, the weekly average severity score of symptomatic RP attacks is reduced by at least about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 from the baseline weekly average severity score, wherein the severity score is based on 0 to 10 numeric rating scale. In one embodiment, the weekly average severity score reduction is provided as a mean value (score) for a SSc population treated with iloprost or a pharmaceutically acceptable salt thereof.

In embodiments, a treatment effect of iloprost or a pharmaceutically acceptable salt thereof on the weekly average severity score of symptomatic RP attacks is about −0.2 to about −5.0, including all values and subranges therebetween. In embodiments, a treatment effect of iloprost or a pharmaceutically acceptable salt thereof on the weekly average severity score of symptomatic RP attacks is about −0.3 to about −3.0, including all values and subranges therebetween. In embodiments, a treatment effect of iloprost or a pharmaceutically acceptable salt thereof on the weekly average severity score of symptomatic RP attacks is about −0.5 to about −2.5, including all values and subranges therebetween. In embodiments, a treatment effect of iloprost or a pharmaceutically acceptable salt thereof on the weekly average severity score of symptomatic RP attacks is about −0.3 to about −2.0, including all values and subranges therebetween. In embodiments, a treatment effect of iloprost or a pharmaceutically acceptable salt thereof on the weekly average severity score of symptomatic RP attacks is about −0.5 to about −1.5, including all values and subranges therebetween. In embodiments, a treatment effect of iloprost or a pharmaceutically acceptable salt thereof on the weekly average severity score of symptomatic RP attacks is about −0.6 to about −1.5, including all values and subranges therebetween. In embodiments, a treatment effect of iloprost or a pharmaceutically acceptable salt thereof on the weekly average severity score of symptomatic RP attacks is at least about −0.2, about −0.3, about −0.4, about −0.5, about −0.6, about −0.7, about −0.8, about −0.9, about −1.0, about −1.1, about −1.2, about −1.3, about −1.4, about −1.5, about −1.6, about −1.7, about −1.8, about −1.9, or about −2.0, including all values therebetween. A treatment effect is the change in the weekly average severity score of symptomatic RP attacks from baseline to end of efficacy follow-up. The primary analysis on this endpoint is performed based on an analysis of covariance (ANCOVA) model, including randomized treatment group and randomized stratification (i.e., use of phosphodiesterase inhibitors at screening) as factors and baseline weekly RP attacks as a covariate. The treatment comparisons (iloprost vs placebo) will be estimated together with the 95% confidence interval and p-value. For example, if the subject who received iloprost treatment and the subject who received placebo both had a baseline weekly average severity score of 5.5 and the weekly average severity score of the subject who received iloprost reduced to 4.0 and the subject who received placebo reduced to 5.0, then the treatment effect is −1.0.

In embodiments, the weekly average severity of symptomatic RP attacks is reduced for a period of about 1 week to about 6 months after one iloprost treatment (e.g., 5 days of infusion), including any values therebetween. In embodiments, the weekly average severity of symptomatic RP attacks is reduced for a period of about 2 weeks to about 3 months after one iloprost treatment, including any values therebetween. In embodiments, the weekly average severity of symptomatic RP attacks is reduced for a period of about 3 weeks to about 20 weeks after one iloprost treatment, including any values therebetween. In embodiments, the weekly average severity of symptomatic RP attacks is reduced for a period of at least 2 week, 3 weeks, 4 weeks, 5 weeks, 6 weeks, 7 weeks, 8 weeks, 9 weeks, 10 weeks, 11 weeks, or 12 weeks after one iloprost treatment, including any values therebetween. In embodiments, the weekly average severity of symptomatic RP attacks is reduced for a period of about 7 weeks, about 8 weeks, about 9 weeks, or about 10 weeks after one iloprost treatment, including any values therebetween.

The present disclosure also relates to methods of determining the effect of iloprost or a pharmaceutically acceptable salt thereof in a subject with systemic sclerosis experiencing symptomatic RP attacks, comprising:
a) obtaining daily numeric severity rating score of each of the following symptoms of the fingers: pain, numbness, discomfort, and tingling, in the subject for 10 to 25 days prior to administering iloprost or a pharmaceutically acceptable salt thereof;
b) calculating a baseline weekly average severity score of each symptom for the subject;
c) selecting the symptom with the worst baseline weekly average severity score;
d) administering iloprost or a pharmaceutically acceptable salt thereof by intravenous or subcutaneous injection at about 0.5 ng/kg/min to about 2.0 ng/kg/min for about 6 hours a day for 5 consecutive days;
e) obtaining daily numeric severity rating score of the following symptoms of the fingers: pain, numbness, discomfort, and tingling, in the subject for about 2 weeks to about 10 weeks after the administration of iloprost or a pharmaceutically acceptable salt thereof;
f) calculating an average weekly severity score of each symptom in the subject; and
g) comparing the baseline weekly average severity score and the weekly average severity score of the symptom determined in step c).

In embodiments of the methods of determining the effect of iloprost as discussed herein, step a) and step e), the daily numeric severity rating score reflects the value of the worst symptom in a given day.

In embodiments of the methods of determining the effect of iloprost as discussed herein, the daily numeric severity rating score of symptomatic RP attack episodes are reported by the subject in step a). In embodiments of the methods of determining the effect of iloprost as discussed herein, the daily severity rating score of symptomatic RP attack episodes are reported by the subject in step d).

In embodiments of the methods of determining the effect of iloprost as discussed herein, step d) of administering iloprost or a pharmaceutically acceptable salt thereof can be replaced by any of the methods disclosed herein. In embodiments, step d) is by infusion.

In embodiments of the methods of determining the effect of iloprost as discussed herein, the amount of time in step e) for obtaining daily numeric severity rating score of the symptomatic RP attack episodes in the subject after the administration of iloprost or a pharmaceutically acceptable salt thereof can range from 1 day to about 12 weeks after the treatment. In embodiments, the effect of iloprost can be determined from obtaining daily numeric severity rating score of the symptomatic RP attack episodes in the subject after the administration of iloprost or a pharmaceutically acceptable salt thereof from about 1 day to about 1 week, from about 1 day to about 2 weeks, from about 1 day to about 3 weeks, or from about 1 day to about 4 weeks after the treatment, In embodiments of the methods of determining the effect of iloprost as discussed herein, the iloprost treatment is effective when the weekly average severity score of the symptomatic RP attacks after the administration of iloprost or a pharmaceutically acceptable salt thereof in step f) is lower than the baseline weekly average severity score of the symptomatic RP attacks in step c) of the subject for the same symptom selected in step c).

The present disclosure also relates to reducing the weekly average frequency and weekly average severity of symptomatic RP attacks from baseline in a SSc subject experiencing symptomatic attacks, comprising administering iloprost or a pharmaceutically acceptable salt thereof or a stereoisomer thereof. In embodiments, iloprost or a pharmaceutically acceptable salt thereof or a stereoisomer thereof is administered in any method as disclosed herein. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to reducing the weekly average duration and weekly average severity of symptomatic RP attacks from baseline in a SSc subject experiencing symptomatic attacks, comprising administering iloprost or a pharmaceutically acceptable salt thereof or a stereoisomer thereof. In embodiments, iloprost or a pharmaceutically acceptable salt thereof or a stereoisomer thereof is administered in any method as disclosed herein. In embodiments the weekly average duration is reduced by at least 30% and the weekly average severity is reduced by at least 30%. In embodiments the weekly average duration is reduced by at least 40% and the weekly average severity is reduced by at least 40%. In embodiments the weekly average duration is reduced by at least 50% and the weekly average severity is reduced by at least 50%. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to reducing the weekly average frequency and weekly average duration of symptomatic RP attacks from baseline in a SSc subject experiencing symptomatic attacks, comprising administering iloprost or a pharmaceutically acceptable salt thereof or a stereoisomer thereof. In embodiments, iloprost or a pharmaceutically acceptable salt thereof or a stereoisomer thereof is administered in any method as disclosed herein. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to reducing the weekly average frequency, weekly average duration, and weekly average severity of symptomatic RP attacks from baseline in a SSc subject experiencing symptomatic attacks, comprising administering iloprost or a pharmaceutically acceptable salt thereof or a stereoisomer thereof. In embodiments, iloprost or a pharmaceutically acceptable salt thereof or a stereoisomer thereof is administered in any method as disclosed herein. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to increasing the number of days without symptomatic RP attacks in a SSc subject from baseline, comprising administering iloprost or a pharmaceutically acceptable salt thereof or a stereoisomer thereof. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to reducing the worst pain associated with symptomatic RP attacks from baseline in a SSc subject, comprising administering iloprost or a pharmaceutically acceptable salt thereof or a stereoisomer thereof. In embodiments, the worst pain is provided as a score given to the worst pain in a given day. In embodiments, the worst pain score is the weekly average worst pain score. In embodiments, the weekly average worst pain score is reduced by a number in the range of about 0.2 to about 5.0 from the baseline weekly average worst pain score, wherein the worst pain score is based on 0 to 10 numeric rating scale. In embodiments, the weekly average worst pain score of symptomatic RP attacks is reduced by a number in the range of about 0.3 to about 4.0 from the baseline weekly average worst pain score, wherein the worst pain score is based on 0 to 10 numeric rating scale. In embodiments, the weekly average worst pain score of symptomatic RP attacks is reduced by a number in the range of about 0.5 to about 3.0 from the baseline weekly average worst pain score, wherein the pain score is based on 0 to 10 numeric rating scale. In embodiments, the weekly average worst pain score of symptomatic RP attacks is reduced by a number in the range of about 0.5 to about 2.0 from the baseline weekly average worst pain score, wherein the pain score is based on 0 to 10 numeric rating scale. In embodiments, the weekly average worst pain score of symptomatic RP attacks is reduced by a number in the range of about 0.5 to about 1.5 from the baseline weekly average worst pain score, wherein the pain score is based on 0 to 10 numeric rating scale. In embodiments, the weekly average worst pain score of symptomatic RP attacks is reduced by a number in the range of about 0.6 to about 1.3 from the baseline weekly average worst pain score, wherein the pain score is based on 0 to 10 numeric rating scale. In embodiments, the weekly average worst pain score of symptomatic RP attacks is reduced by at least about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 from the baseline weekly average worst pain score, wherein the worst pain score is based on 0 to 10 numeric rating scale. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to reducing the worst numbness associated with symptomatic RP attacks from baseline in a SSe subject, comprising administering iloprost or a pharmaceutically acceptable salt thereof or a stereoisomer thereof. In embodiments, the worst numbness is provided as a score given to the worst numbness in a given day. In embodiments, the worst numbness score is the weekly average worst numbness score. In embodiments, the weekly average worst numbness score is reduced by a number in the range of about 0.2 to about 5.0 from the baseline weekly average worst numbness score, wherein the worst numbness score is based on 0 to 10 numeric rating scale. In embodiments, the weekly average worst numbness score of symptomatic RP attacks is reduced by a number in the range of about 0.3 to about 4.0 from the baseline weekly average worst numbness score, wherein the worst numbness score is based on 0 to 10 numeric rating scale. In embodiments, the weekly average worst numbness score of symptomatic RP attacks is reduced by a number in the range of about 0.5 to about 2.0 from the baseline weekly average worst numbness score, wherein the numbness score is based on 0 to 10 numeric rating scale. In embodiments, the weekly average worst numbness score of symptomatic RP attacks is reduced by a number in the range of about 0.7 to about 1.2 from the baseline weekly average worst numbness score, wherein the numbness score is based on 0 to 10 numeric rating scale. In embodiments, the weekly average worst numbness score of symptomatic RP attacks is reduced by a number in the range of about 0.5 to about 3.0 from the baseline weekly average worst numbness score, wherein the numbness score is based on 0 to 10 numeric rating scale. In embodiments, the weekly average worst numbness score of symptomatic RP attacks is reduced by at least about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 from the baseline weekly average worst numbness score, wherein the worst numbness score is based on 0 to 10 numeric rating scale. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to reducing the worst tingling associated with symptomatic RP attacks from baseline in a SSc subject, comprising administering iloprost or a pharmaceutically acceptable salt thereof or a stereoisomer thereof. In embodiments, the worst tingling is provided as a score given to the worst tingling in a given day. In embodiments, the worst tingling score is the weekly average worst tingling score. In embodiments, the weekly average worst tingling score is reduced by a number in the range of about 0.2 to about 5.0 from the baseline weekly average worst tingling score, wherein the worst tingling score is based on 0 to 10 numeric rating scale. In embodiments, the weekly average worst tingling score of symptomatic RP attacks is reduced by a number in the range of about 0.3 to about 40 from the baseline weekly average worst tingling score, wherein the worst tingling score is based on 0 to 10 numeric rating scale. In embodiments, the weekly average worst tingling score of symptomatic RP attacks is reduced by a number in the range of about 0.5 to about 3.0 from the baseline weekly average worst tingling, wherein the tingling score is based on 0 to 10 numeric rating scale. In embodiments, the weekly average worst tingling score of symptomatic RP attacks is reduced by a number in the range of about 0.5 to about 2.0 from the baseline weekly average worst tingling, wherein the tingling score is based on 0 to 10 numeric rating scale. In embodiments, the weekly average worst tingling score of symptomatic RP attacks is reduced by a number in the range of about 0.7 to about 1.2 from the baseline weekly average worst tingling, wherein the tingling score is based on 0 to 10 numeric rating scale. In embodiments, the weekly average worst tingling score of symptomatic RP attacks is reduced by at least about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 from the baseline weekly average worst tingling score, wherein the worst tingling score is based on 0 to 10 numeric rating scale. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to reducing the worst discomfort associated with symptomatic RP attacks rom baseline in a SSc subject, comprising administering iloprost or a pharmaceutically acceptable salt thereof or a stereoisomer thereof. In embodiments, the worst discomfort is provided as a score given to the worst discomfort in a given day. In embodiments, the worst discomfort score is the weekly average worst discomfort score. In embodiments, the weekly average worst discomfort score is reduced by a number in the range of about 0.2 to about 5.0 from the baseline weekly average worst discomfort score, wherein the worst discomfort score is based on 0 to 10 numeric rating scale. In embodiments, the weekly average worst discomfort score of symptomatic RP attacks is reduced by a number in the range of about 0.3 to about 4.0 from the baseline weekly average worst discomfort score, wherein the worst discomfort score is based on 0 to 10 numeric rating scale. In embodiments, the weekly average worst discomfort score of symptomatic RP attacks is reduced by a number in the range of about 0.5 to about 3.0 from the baseline weekly average worst discomfort, wherein the discomfort score is based on 0 to 10 numeric rating scale. In embodiments, the weekly average worst discomfort score of symptomatic RP attacks is reduced by a number in the range of about 0.5 to about 2.0 from the baseline weekly average worst discomfort, wherein the discomfort score is based on 0 to 10 numeric rating scale. In embodiments, the weekly average worst discomfort score of symptomatic RP attacks is reduced by a number in the range of about 0.7 to about 1.2 from the baseline weekly average worst discomfort, wherein the discomfort score is based on 0 to 10 numeric rating scale. In embodiments, the weekly average worst discomfort score of symptomatic RP attacks is reduced by at least about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 from the baseline weekly average worst discomfort score, wherein the worst discomfort score is based on 0 to 10 numeric rating scale. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to reducing the average duration of a symptomatic RP attack episode from baseline in a SSc subject, comprising administering iloprost or a pharmaceutically acceptable salt thereof or a stereoisomer thereof. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to changing a SSc subject's assessment of overall change in symptomatic RP attacks from baseline, comprising administering iloprost or a pharmaceutically acceptable salt thereof or a stereoisomer thereof. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to changing a SSc subject's assessment of overall severity in symptomatic RP attacks from baseline, comprising administering iloprost or a pharmaceutically acceptable salt thereof or a stereoisomer thereof. In embodiments, iloprost or a pharmaceutically acceptable salt thereof or a stereoisomer thereof is administered at a dose in the range of about 0.5 ng/kg/min to about 2.0 ng/kg/min for about 6 hours a day for 5 consecutive days.

The present disclosure also relates to restoring function lost due to SSc, comprising administration of iloprost or a pharmaceutically acceptable salt thereof or a stereoisomer thereof. In embodiments, iloprost or a pharmaceutically acceptable salt thereof or a stereoisomer thereof can enhance cutaneous blood flow. In embodiments, iloprost or a pharmaceutically acceptable salt thereof or a stereoisomer thereof can reduce microvascular inflammation. In embodiments, iloprost or a pharmaceutically acceptable salt thereof or a stereoisomer thereof can attenuate fibrosis. In embodiments, iloprost or a pharmaceutically acceptable salt thereof or a stereoisomer thereof can decrease platelet aggregation and adhesion.

The present disclosure also relates to reducing the severity of vasoconstrictive episodes response in a SSc subject, comprising administering iloprost or a pharmaceutically acceptable salt thereof or a stereoisomer thereof.

The present disclosure also relates to methods of treating digital ischemia exacerbation in a SSc subject, comprising administering iloprost or a pharmaceutically acceptable salt thereof or a stereoisomer thereof. The present disclosure also relates to reducing the frequency of having digital ischemia exacerbation episodes in a SSc subject, comprising administering iloprost or a pharmaceutically acceptable salt thereof or a stereoisomer thereof.

The present disclosure also relates to preventing the development of digital ischemia in a SSc subject, comprising administering iloprost or a pharmaceutically acceptable salt thereof or a stereoisomer thereof. The present disclosure also relates to reducing the frequency of developing digital ischemia in a SSc subject, comprising administering iloprost or a pharmaceutically acceptable salt thereof or a stereoisomer thereof.

The present disclosure also relates to preventing the development of critical digital ischemia in a SSc subject, comprising administering iloprost or a pharmaceutically acceptable salt thereof or a stereoisomer thereof. The present disclosure also relates to reducing the frequency of developing critical digital ischemia in a SSc subject, comprising administering iloprost or a pharmaceutically acceptable salt thereof or a stereoisomer thereof.

The present disclosure also relates to preventing the development of digital ischemic episodes in a SSc subject, comprising administering iloprost or a pharmaceutically acceptable salt thereof or a stereoisomer thereof. The present disclosure also relates to reducing the frequency of developing digital ischemic episodes in a SSc subject, comprising administering iloprost or a pharmaceutically acceptable salt thereof or a stereoisomer thereof.

The present disclosure also relates to preventing the development of digital ischemic ulcers in a SSc subject, comprising administering iloprost or a pharmaceutically acceptable salt thereof or a stereoisomer thereof. The present disclosure also relates to reducing the frequency of developing digital ischemic ulcers in a SSc subject, comprising administering iloprost or a pharmaceutically acceptable salt thereof or a stereoisomer thereof.

The present disclosure also relates to preventing the development of digital ischemic lesions in a SSc subject, comprising administering iloprost or a pharmaceutically acceptable salt thereof or a stereoisomer thereof. The present disclosure also relates to reducing the frequency of developing digital ischemic lesions in a SSc subject, comprising administering iloprost or a pharmaceutically acceptable salt thereof or a stereoisomer thereof.

The present disclosure also relates to preventing the development of symptomatic ischemic lesions in a SSc subject, comprising administering iloprost or a pharmaceutically acceptable salt thereof or a stereoisomer thereof. The present disclosure also relates to reducing the frequency of developing symptomatic ischemic lesions in a SSc subject, comprising administering iloprost or a pharmaceutically acceptable salt thereof or a stereoisomer thereof.

The present disclosure also relates to preventing the development of gangrene in a SSc subject, comprising administering iloprost or a pharmaceutically acceptable salt thereof or a stereoisomer thereof. The present disclosure also relates to preventing the frequency of developing gangrene in a SSc subject, comprising administering iloprost or a pharmaceutically acceptable salt thereof or a stereoisomer thereof.

The present disclosure also relates to preventing the development of digital infection in a SSc subject, comprising administering iloprost or a pharmaceutically acceptable salt thereof or a stereoisomer thereof. The present disclosure also relates to preventing the frequency of developing digital infection in a SSc subject, comprising administering iloprost or a pharmaceutically acceptable salt thereof or a stereoisomer thereof.

In embodiments, any of the aforementioned benefits or effects of iloprost or a pharmaceutically acceptable salt thereof can last about 3 weeks to about 12 weeks after a single treatment, including all ranges and values therebetween. In embodiments, any of the aforementioned benefits or effects of iloprost or a pharmaceutically acceptable salt thereof can, on average in a SSc population, last about 3 weeks to about 12 weeks after a single treatment, including all ranges and values therebetween. The benefit or effects of iloprost or a pharmaceutically acceptable salt thereof can be extended or reduced depending on number of factors. The symptomatic RP attack episodes generally worsen in the winter and/or during times of emotional or physical stress.

In embodiments, the subject has a baseline estimated glomerular filtration rate (eGFR) of less than about 90 mL/min/1.73 m$^2$. In embodiments, the subject has a baseline eGFR of less than 90 mL/min/1.73 m$^2$. In embodiments, the subject has a baseline eGFR of greater than or equal to about 90 mL/min/1.73 m$^2$. In embodiments, the subject has a baseline eGFR of greater than or equal to 90 mL/min/1.73 m$^2$.

EXAMPLES

The disclosure now being generally described, it will be more readily understood by reference to the following examples which are included merely for purposes of illustration of certain aspects and embodiments of the present invention, and are not intended to limit the invention.

Example 1. A Multicenter, Double-Blind, Randomized, Placebo-Controlled, Study Evaluating Intravenous Iloprost in Subjects with Symptomatic Raynaud's Phenomenon Secondary to Systemic Sclerosis This was a multicenter, double-blind, randomized, placebo-controlled study to provide an initial evaluation of the effect of iloprost on the symptomatic relief of RP attacks in subjects with SSc. As a pilot study, it was not powered to provide a definitive estimate of the effect of iloprost. Importantly, this study tested the feasibility of collecting the study endpoints and logistics of study operations that included, among other things, an electronic patient-reported outcomes (ePRO) diary for the evaluation of subject response to the treatment, as well as the infusion workflow for this multiday treatment. Subjects were allowed to continue receiving stable standard of care therapies for the management of symptomatic RP (e.g., calcium channel blockers, angiotensin-converting enzyme inhibitors, statins, fluoxetine, and low-dose acetylsalicylic acid) or may have participated without the use of background standard of care therapies.

The primary objective was to evaluate the efficacy of iloprost compared to placebo on the change in the weekly frequency of symptomatic Raynaud's Phenomenon (RP) attacks from baseline in subjects with symptomatic RP secondary to Systemic Sclerosis (SSc). The exploratory objectives were the following:

- To evaluate the efficacy of iloprost compared to placebo on the severity of RP attack symptoms
- To evaluate the efficacy of iloprost compared to placebo on the Raynaud's Condition Score
- To evaluate the efficacy of iloprost compared to placebo on hand function as assessed by the Cochin Hand Function Scale (CHFS)
- To evaluate the safety and tolerability of iloprost
- To evaluate the efficacy of iloprost compared to placebo on symptomatic RP attack duration
- To evaluate the efficacy of iloprost compared to placebo on the worst pain associated with symptomatic RP To evaluate the efficacy of iloprost compared to placebo on the subject assessment of overall improvement in symptomatic RP To evaluate the pharmacokinetics (PK) of iloprost in subjects with symptomatic RP secondary to SSc Methodology The study consisted of an up to 30-day screening period during which subjects completed a daily ePRO diary to record information regarding all symptomatic RP attacks (e.g., severity of symptoms, duration, and hand function). The up to 30-day screening period consisted of a 5-day eligibility period and an up to 25-day baseline ePRO diary completion period:

During the 5-day eligibility period, eligible subjects must have had a minimum of 10 symptomatic RP attacks, documented in the ePRO diary, that occurred over at least 3 separate days of the 5-day eligibility period.

During the baseline ePRO diary completion period, eligible subjects completed the daily ePRO diary for a minimum of 10 days (up to a maximum of 25 days) until the day of randomization. The baseline ePRO diary completion period may have been extended beyond 10 days in order to accommodate the preferred Monday through Friday dosing schedule. The ePRO symptomatic RP attack data from this time period were used for the calculation of the baseline frequency of symptomatic RP attacks.

Eligible subjects were given the option to participate in a PK sub-study. Subjects who participated in the sub-study provided plasma samples for PK analysis. The samples were analyzed for iloprost concentrations using validated liquid chromatography mass spectrometry methods.

Subjects were randomized in a 1:1 ratio to iloprost injection for IV use or placebo. Randomization was stratified based on the use of phosphodiesterase inhibitors at screening. Study drug administration began on Day 1, and subjects received study drug for 5 consecutive days (e.g., Monday through Friday) as an IV infusion over 6 hours each day via a peripheral line (NovaCath™ Integrated IV Catheter System) or a peripherally inserted central catheter using an infusion pump.

Subjects must have had a systolic blood pressure ≥85 mmHg (sitting position) prior to study drug administration each day of administration. On Day 1, study drug was initiated at a starting dose of 0.5 ng/kg/min, and dose increases occurred every 30 minutes (+5 minutes) in increments of 0.5 ng/kg/min up to 2.0 ng/kg/min or the individual tolerated dose. If dose-limiting adverse events (e.g., headache, flushing, jaw pain, myalgia, nausea, or vomiting) occurred that could not be tolerated by the subject, or if the subject experienced symptomatic hypotension, then the dose was reduced in a step-wise manner by 0.5 ng/kg/min every 30 minutes (+5 minutes) until a tolerated dose was determined or the infusion was stopped until the symptoms resolved at which point the study drug was reinitiated at a previously tolerated dose. If symptomatic hypotension or a dose-limiting adverse event occurred during administration of iloprost at the starting dose (i.e., 0.5 ng/kg/min), the infusion was reduced to 0.25 ng/kg/min. If the dose of 0.25 ng/kg/min was not tolerated due to symptomatic hypotension or if a dose-limiting adverse event occurred, the study drug was discontinued, and re-initiation of the infusion could have been attempted after the event had resolved or had been treated. Blood pressure and heart rate were monitored 15 minutes (+5 minutes) prior to and after all dose changes. The maximum tolerated dose was maintained for the remaining 6-hour daily period. At the end of the 6-hour infusion period, the dose was stopped. Subjects were to be monitored for up to 1 hour after completion of study drug infusion (i.e., vital signs were obtained 15 minutes [±5 minutes] and 1 hour [±15 minutes] after completion of the infusion).

On Days 2 to 5, the infusion was started using the highest infusion rate tolerated on the previous day without up- or down-titration, unless the subject did not tolerate the infusion or adverse events occurred that could not be tolerated by the subject and necessitated a reduction in the dose. Vital signs were measured prior to study drug administration and at 15 minutes (±5 minutes) prior to and after all dose changes during the infusion. Additionally, vital signs were monitored at 15 minutes (±5 minutes) and 1 hour (±15 minutes) after completion of the 6-hour infusion.

During the treatment period (Days 1 to 5), while subjects received study drug, the ePRO diary was not completed. No study assessments were performed on the 2 days following the end of treatment (Days 6 and 7 [i.e., Saturday and Sunday]) to allow the subject to rest and return to a schedule of normal daily living activity following the 5 days of infusions.

Subjects were contacted via telephone on Day 8 to ensure they resumed completion of the daily ePRO diary; subjects completed the ePRO diary from Day 8 through Day 21. On Day 22, subjects returned to the clinic for post-treatment evaluations. A follow-up visit occurred 30 days after the last administration of study drug (Day 35).

Subjects who discontinued study drug early remained in the study (unless the subject withdrew consent) and completed the daily ePRO diary from Day 8 to Day 21, including clinical laboratory assessments on the remaining missed infusion days as well as post-treatment study assessments.

The total duration of the study for a subject was up to approximately 9 weeks.

Number of subjects: Randomized—34 subjects; Completed—34 subjects

Diagnosis and Main Criteria for Inclusion: The population for this study included male and female subjects ≥18 years of age who met the following criteria: had a diagnosis of SSc, as defined by the 2013 American College of Rheumatology criteria/European League Against Rheumatism criteria; had a diagnosis or history of RP, self-reported or reported by a physician, with at least a 2-phase color change in figure(s) of pallor, cyanosis, and/or reactive hyperemia in response to cold exposure or emotion; and had a minimum of 10 symptomatic RP attacks, documented in the ePRO diary, that occurred over at least 3 separate days of the 5-day eligibility period.

Investigational Product and Comparator Information: Iloprost injection for IV use and matching placebo were supplied in vials packaged in a blinded study drug kit (10 vials per kit). The iloprost and placebo vials were identical, except 100 mcg of iloprost was added to the active study drug vials. The drug product was diluted with sodium chloride 0.9% in a drug reservoir (IV bag) prior to use.

Criteria for Evaluation

Efficacy

The primary efficacy parameter was the change in the weekly frequency of symptomatic RP attacks from baseline.

The exploratory efficacy parameters included changes from baseline to the end of the efficacy follow-up in the following:

Severity of RP attacks, as determined by the severity of RP attack symptoms (pain, numbness, tingling, and/or discomfort) (using a Numeric Rating Scale [NRS])

Raynaud's Condition Score

Hand function, as assessed by the Cochin Hand Functional Scale (CHFS)

Duration of symptomatic RP attacks

NRS for worst pain associated with symptomatic RP

Subject assessment of overall improvement in symptomatic RP (Patient

Global Impression of Severity [PGI-S] and Patient Global Impression of Change [PGI-C])

Pharmacokinetics

The following PK parameters were calculated whenever possible, based on the plasma concentrations of iloprost:

Steady state plasma concentration just before infusion was stopped

Area under the plasma concentration versus time curve (AUC) from time of dosing to the last time point with measurable concentration ($AUC_{0-last}$)

AUC from time 0 extrapolated to infinity ($AUC_{0-inf}$)

Percentage of AUC obtained by extrapolation ($AUC_{extrape\%}$)

Terminal elimination constant ($\lambda z$)

Plasma terminal elimination half-life (t½)

Plasma clearance (CL), calculated as dose/$AUC_{0-inf}$

Volume of distribution (V), calculated as dose/($\lambda z \times AUC_{0-inf}$)

Safety

Safety parameters included adverse events, physical examination findings, vital sign measurements (heart rate and blood pressure), 12-lead electrocardiogram (ECG) findings, and standard clinical laboratory measurements (chemistry and hematology).

Efficacy and Safety Variables

Symptomatic Raynaud's Phenomenon attacks: A symptomatic Raynaud's Phenomenon (RP) attack for this study was defined as at least 1 color change of the subject's finger(s) (blue, purple, white, or red) associated with at least 1 symptom (pain, numbness, tingling, and/or discomfort of the finger [s]). The attack was considered over when the color changed back to pre-attack color (normal) and the symptoms returned to the subject's pre-attack level.

Electronic patient-reported outcomes diary: Subjects were provided with an ePRO diary at Visit 1 and trained on its use. Subjects were asked to complete the ePRO diary at the time points discussed above. Questionnaires allowed for documentation of frequency, severity, and duration of symptomatic RP attacks, as well as assessment of hand function. Specific questionnaires included the severity of RP attack symptoms (using a Numeric Rating Scale [NRS]), Raynaud's Condition Score, CHFS, and overall subject improvement (Patient Global Impression of Severity [PGI-S] and Patient Global Impression of Change [PGI-C]).

Severity of Raynaud's Phenomenon attack symptoms (using a Numeric Rating Scale): Raynaud's Phenomenon attacks are associated with significant discomfort (pain, numbness, tingling, and/or discomfort). Subjects were asked to rate the severity of RP attack symptoms (pain, numbness, tingling, and/or discomfort) using an 11-point NRS. Intensity was assessed as follows: 0 (no pain/numbness/tingling/discomfort), 1 to 3 (mild pain/numbness/tingling/discomfort), 4 to 6 (moderate pain/numbness/tingling/discomfort), and 7 to 10 (severe pain/numbness/tingling/discomfort).

Raynaud's Condition Score: The Raynaud's Condition Score asked subjects to rate their difficulty with RP condition on a given day from 0 (no difficulty) to 10 (extreme difficulty). Subjects were asked to consider the number of attacks they had on that day and how long each attack lasted. Subjects were asked to consider how much pain, numbness, or other symptoms the RP caused in their fingers (including painful sores) and how much the RP alone affected the use of their hands that day.

Cochin Hand Function Scale: Raynaud's Phenomenon attacks have a significant impact on hand function. The CHFS is an 18-item self-administered instrument that assesses hand function as it relates to daily activities. The CHFS has been validated for use in subjects with SSc.

Duration of symptomatic Raynaud's Phenomenon attacks: Subjects were asked to document the duration of each symptomatic RP attack within their ePRO diaries. For each attack, the subject recorded the duration in minutes.

Worst pain associated with symptomatic Raynaud's Phenomenon: Subjects were asked to rate the severity of the worst pain using an 11-point NRS within their ePRO diaries. Worst numbness, worst tingling, and worst discomfort were also assessed in the same way.

Overall subject improvement: On Day-1, subjects were asked to rate the overall severity of their symptomatic RP in the last week using a PGI-S score (0 to 10).

On Day 21, subjects were asked to rate the overall severity of their symptomatic RP in the last week using a PGI-S score (0 to 10) and the overall change in their symptomatic RP compared to the start of the study using a PGI-C score (much worse, a little worse, no change, a little better, or much better).

During the study, the Day-1 questionnaires were collected on the first day of the baseline ePRO diary completion period, and the end-of-study questionnaires were collected at Day 21 or 22.

Summary of Results

Efficacy

Overall, the number of subjects who completed at least 7 days of the ePRO diary for selected efficacy questions at baseline and the double-blind endpoint was high. During the 10- to 25-day baseline ePRO diary completion period, all 17 (100.0%) subjects in both the placebo group and the iloprost group completed at least 7 days of ePRO diary for all efficacy questions except for the question of "how many RP attacks in the past 24 hours" in the placebo group, where 16 (94.1%) subjects completed at least 7 days of ePRO diary. At the double-blind endpoint, 16 (94.1%) subjects in the placebo group and 17 (100.0%) subjects in the iloprost group completed at least 7 days of ePRO diary for all of the questions.

For the primary efficacy parameter, decreases in the weekly frequency of symptomatic RP attacks were observed from baseline to the double-blind endpoint for both the placebo group and the iloprost group, as analyzed by ANCOVA (least squares [LS] mean [standard error {SE}] change of −14.32 [2.858] in the placebo group and −15.09 [2.961] in the iloprost group; p<0.0001) and nonparametric analysis (median [first quartile, third quartile] change of −11.67 [−18.86, −2.69] for the placebo group and −9.40 [−21.03, −7.50] for the iloprost group; statistical significance not assessed) (Table 3). The percent change in the weekly frequency of symptomatic RP attacks was also analyzed and showed directionally similar results to those seen with the weekly change parameter. However, the differences in the change in the weekly frequency of symptomatic RP attacks from baseline to the double-blind endpoint in the iloprost group compared to placebo were not statistically significant in any of the analytical measures listed above.

TABLE 3

Change in Weekly Frequency of Symptomatic RP Attacks from Baseline

| Category<br>Statistic | Placebo<br>(N = 17) | Iloprost<br>(N = 17) |
|---|---|---|
| Number of subjects | | |
| n [1] | 17 | 17 |
| Baseline [2] | | |
| Mean (SD) | 42.32 (29.635) | 37.05 (18.643) |
| Double-blind endpoint [3] | | |
| Mean (SD) | 27.56 (25.416) | 23.57 (14.578) |
| Change from baseline | | |
| LS mean (SE) | −14.32 (2.858) | −15.09 (2.961) |
| 95% CI | (−20.15, −8.48) | (−21.14, −9.04) |
| p-value | <0.0001 | <0.0001 |
| Treatment comparison of change vs placebo | | |
| LS mean difference in change (SE) | | −0.77 (4.047) |
| 95% CI | | (−9.04, 7.49) |
| p-value | | 0.8498 |
| Shapiro-Wilk normality test of residuals | | |
| p-value | | 0.0108 |

Note:
When a subject had no RP attacks in the past 24 hours, the frequency was considered as zero for that day. The LS means, SEs, CIs, and p-values came from an ANCOVA model with randomized treatment group and use of phosphodiesterase inhibitors at screening (yes, no) as factors and baseline as a covariate. For subjects in the Modified Intent-to-Treat Population with a missing primary efficacy endpoint, multiple imputation was used.
[1] n equaled the number of subjects with a result at both baseline and the double-blind endpoint.
[2] The baseline weekly frequency of symptomatic RP attacks was defined as the average number of weekly symptomatic RP attacks that occurred during the 10- to 25-day baseline ePRO diary completion period.
[3] The double-blind endpoint weekly frequency of symptomatic RP attacks was defined as the average number of weekly symptomatic RP attacks that occurred during Days 8 to 21, inclusive.
ANCOVA = analysis of covariance; CI = confidence interval; ePRO = electronic patient-reported outcomes; LS = least squares; RP = Raynaud's Phenomenon; SD = standard deviation; SE = standard error; vs = versus.

In a predefined analysis of seasonality, the LS mean (SE) difference in the change in the weekly frequency of symptomatic RP attacks from baseline to the double-blind endpoint in the iloprost group compared to placebo (treatment effect) was −4.87 (6.074) in the subgroup of subjects who were randomized prior to 3 Jun. 2019 and 2.04 (5.453) in the subgroup of subjects who were randomized after 3 Jun. 2019 (Table 4, FIG. 1). Further, when the data is separated for date of randomization between 25 Mar. 2019 to 20 May 2019, the treatment effect was −8.46 (FIG. 1). These results were numerically consistent with an effect of season; however, these comparisons were not statistically significant ($p=0.4292$ and $p=0.7116$ for the comparisons between iloprost and placebo in the subgroups of subjects randomized prior to and after 3 Jun. 2019, respectively). When comparing the treatment difference in subgroups of subjects who were randomized prior to and after 3 Jun. 2019, the LS mean (SE) difference was −6.91 (8.121) for the change in weekly frequency of symptomatic RP attacks from baseline to the double-blind endpoint; however, this observation was not statistically significant ($p=0.4021$). Seasonal variation has been observed in previous reports. Wigley, F. M. et al. *Ann Intern Med.* 1994, 120, 199-206; Wigley, F. M. et al. *J Rheumatol.* 1992, 19, 1407-1414.

TABLE 4

Change in Weekly Frequency of Symptomatic RP Attacks from Baseline

| | Randomization Date Prior to 3 Jun. 2019 | | Randomization Date After 3 Jun. 2019 | |
|---|---|---|---|---|
| Category<br>Statistic | Placebo<br>(N = 7) | Iloprost<br>(N) | Placebo<br>(N = 10) | Iloprost<br>(N = 9) |
| Number of subjects | | | | |
| n [1] | 7 | 8 | 10 | 9 |
| Baseline [2] | | | | |
| Mean (SD)<br>Double-blind endpoint [3] | 41.22 (26.777) | 36.85 (19.235) | 43.10 (32.889) | 37.23 (19.269) |
| Mean (SD)<br>Change from baseline | 31.10 (32.602) | 23.39 (11.923) | 25.09 (20.573) | 23.73 (17.337) |
| LS mean (SE) | −9.95 (4.438) | −14.83 (4.180) | −17.41 (3.739) | −15.38 (4.082) |

TABLE 4-continued

Change in Weekly Frequency of Symptomatic RP Attacks from Baseline

| Category<br>Statistic | Randomization Date Prior to 3 Jun. 2019 | | Randomization Date After 3 Jun. 2019 | |
|---|---|---|---|---|
| | Placebo<br>(N = 7) | Iloprost<br>(N) | Placebo<br>(N = 10) | Iloprost<br>(N = 9) |
| Treatment comparison of change vs placebo | | | | |
| LS mean difference in change (SE) | | −4.87 (6.074) | | 2.04 (5.453) |
| 95% CI | | (−17.32, 7.57) | | (−9.13, 13.21) |
| p-value | | 0.4292 | | 0.7116 |
| Subgroup comparison of prior vs after | | | | |
| LS mean difference in change (SE) | | | | −6.91 (8.121) |
| 95% CI | | | | (−23.54, 9.73) |
| p-value | | | | 0.4021 |

[1]-[3] - see Table 3.

Statistically significant decreases (or improvements in the case of PGI-C) from baseline to the double-blind endpoint were observed within treatment group for both the placebo group and the iloprost group in most of the exploratory endpoints analyzed in this study (listed below). However, the differences in the iloprost group compared to placebo were not statistically significant:

The change in average overall severity of RP attack symptoms (Table 5)

The change in average Raynaud's Condition Score

The change in average weekly duration of symptomatic RP attacks (minutes) (Table 6)

The change in average worst symptoms (pain, numbness, tingling, and discomfort) associated with symptomatic RP Subject assessment of overall improvement using PGI-S and PGI-C

TABLE 5

Change in Average Overall Severity of Symptomatic RP Attacks from

| Category<br>Statistic | Placebo<br>(N = 17) | Iloprost<br>(N = 17) |
|---|---|---|
| Number of subjects | | |
| n [1] | 17 | 17 |
| Baseline [2] | | |
| Mean (SD) | 6.12 (2.245) | 5.30 (1.818) |
| Double-blind endpoint [3] | | |
| Mean (SD) | 4.44 (2.473) | 3.39 (2.169) |
| Change from baseline | | |
| LS mean (SE) | −1.65 (0.424) | −2.12 (0.439) |
| 95% CI | (−2.51, −0.78) | (−3.01, −1.22) |
| p-value | 0.0005 | <0.0001 |
| Treatment comparison of change vs placebo | | |
| LS mean difference in change (SE) | | −0.47 (0.604) |
| 95% CI | | (−1.71, 0.76) |
| p-value | | 0.4409 |

[1]-[3] - see Table 3.

TABLE 6

Change in Average Weekly Duration of Symptomatic RP Attacks from Baseline (minutes)

| Category<br>Statistic | Placebo<br>(N = 17) | Ilopcost<br>(N = 17) |
|---|---|---|
| Number of subjects | | |
| n [1]<br>Baseline [2] | 17 | 17 |
| Mean (SD)<br>Double-blind endpoint [3] | 822.53 (630.482) | 586.97 (584.577) |
| Mean (SD)<br>Change from baseline | 608.09 (654.620) | 345.82 (402.713) |
| LS mean (SE)<br>95% CI<br>p-value<br>Treatment comparison of change vs placebo | −183.60 (75.519)<br>(−337.83, −29.37)<br>0.0212 | −267.49 (78.273)<br>(−427.35, −107.64)<br>0.0018 |
| LS mean difference in change (SE)<br>95% CI<br>p-value | | −83.89 (107.728)<br>(−303.90, 136.12)<br>0.4422 |

[1]-[3]—see Table 3.

Pharmacokinetics

Table 7 shows the summary of PK parameters for the PK population. In general, the geometric mean of steady state plasma concentration (Css), AUC0-last, and $AUC_{0\text{-}inf}$ of iloprost increased as dose increased across the 4 maximum tolerated dose levels (from 0.50 to 2.00 ng/kg/min), with the exception of Css and $AUC_{0\text{-}last}$ at the 1.50 ng/kg/min dose level.

The mean t½ of iloprost ranged from 0.381 to 0.471 hours across the 4 dose levels.

TABLE 7

Summary of Pharmacokinetic Parameters

| Parameter<br>Statistic | Maximum Tolerated Dose Level<br>0.50 ng/kg/min | Maximum Tolerated Dose Level<br>1.00 ng/kg/min | Maximum Tolerated Dose Level<br>1.50 ng/kg/min | Maximum Tolerated Dose Level<br>2.00 ng/kg/min |
|---|---|---|---|---|
| $C_{ss}$ (pg/mL) | | | | |
| n<br>Geometric mean<br>(geometric CV %) | 1<br>19.60 (NA) | 2<br>51.31 (20.7) | 2<br>32.90 (284.8) | 4<br>76.82 (56.9) |
| $t_{1/2}$ (h) | | | | |
| n<br>Mean (SD) | | 1<br>0.41 (NA) | 1<br>0.450 (NA) | 1<br>0.381 (NA) |
| $AUC_{0\text{-}inf}$ (h*pg/mL) | | | | |
| n<br>Geometric mean<br>(geometric CV %) | | 1<br>378.9 (NA) | 1<br>602.7 (NA) | 1<br>700.6 (NA) |
| $AUC_{0\text{-}last}$ (h*pg/mL) | | | | |
| n<br>Geometric mean<br>(geometric CV %) | 1<br>116.0 (NA) | 2<br>314.7 (23.9) | 2<br>202.7 (303.2) | 4<br>478.0 (55.6) |
| $CL_{ss}$ (L/h) | | | | |
| N<br>Mean (SD) | | 1<br>91.22 (NA) | 1<br>6.01 (NA) | 1<br>64.53 (NA) |
| $V_{ss}$ (L) | | | | |
| n<br>Mean (SD) | | 1<br>62.01 (NA) | 1<br>49.34 (NA) | 1<br>35.49 (NA) |

Note:
Geometric CV % = 100 × $(exp(SD^2)-1)^{0.5}$, where SD was the SD of the logarithmic-transformed data. One subject was excluded from analysis because the 6-hour postdose PK sample was collected 2 minutes after the infusion stopped.
$AUC_{0\text{-}inf}$ = area under the plasma concentration versus time curve from time 0 extrapolated to infinity;
AUC0-last = area under the plasma concentration versus time curve from time of dosing to the last time point with measurable concentration;
CLss = plasma clearance at steady state;
Css = steady state plasma concentration;
CV % = percent coefficient of variation;
max = maximum;
min = minimum;
NA = not applicable;
PK = pharmacokinetic(s);
SD = standard deviation;
t½ = plasma terminal elimination half-life;
Vss = volume of distribution at steady state.

Safety

No subjects experienced a serious adverse event (SAE), adverse event of special interest (AESI), treatment-emergent adverse event (TEAE) leading to discontinuation of study drug, or TEAE leading to death in this study.

Overall, 31 (91.2%) subjects experienced a TEAE: 14 (82.4%) subjects in the placebo group and 17 (100.0%) subjects in the iloprost group. The majority of TEAEs were considered mild to moderate in severity. Two (11.8%) subjects in the iloprost group experienced TEAEs that were considered severe by the Investigator.

The most commonly reported TEAEs (based on the total number of subjects who experienced this TEAE) were headache (21 [61.8%] subjects total: 5 [29.4%] subjects in the placebo group and 16 [94.1%] subjects in the iloprost group), nausea (14 [41.2%] subjects total: 3 [17.6%] subjects in the placebo group and 11 [64.7%] subjects in the iloprost group), abdominal pain (5 [14.7%] subjects total: 1 [5.9%] subject in the placebo group and 4 [23.5%] subjects in the iloprost group), and flushing (5 [14.7%] subjects total: 0 [0.0%] subjects in the placebo group and 5 [29.4%] subjects in the iloprost group).

There were no clinically significant changes in chemistry or hematology laboratory values during the study.

There were no TEAEs related to vital signs, physical examination findings, or ECGs in this study.

There were no hypertensive or hypotensive events reported in this study. There was no bradycardia or tachycardia reported in this study.

Conclusions

This pilot, multicenter, double-blind, randomized, placebo-controlled study confirmed the ability to evaluate the effect of iloprost on the symptomatic relief of symptomatic RP attacks using an ePRO diary in subjects with SSc. The results also confirmed that the iloprost dosing titration algorithm could be safely used in subjects with SSc. All adverse events related to the study drug as assessed by the Investigator were expected and consistent with the known safety profile of iloprost. There were no deaths, SAEs, AESIs, or TEAEs leading to study drug discontinuation during this study.

The study was not adequately powered to test the efficacy of iloprost for reducing the frequency of RP attacks compared to placebo. The seasonality finding is consistent with previous iloprost studies conducted in the spring and summer months, and the study was underpowered.

Example 2. A Multicenter, Double-Blind, Randomized, Placebo-Controlled Study Evaluating the Safety and Efficacy of Intravenous Iloprost in Subjects With Systemic Sclerosis Experiencing Symptomatic Digital Ischemic Episodes This is a multicenter, double-blind, randomized, placebo-controlled study to evaluate the safety and efficacy of iloprost on the frequency of and relief from symptomatic digital ischemic episodes in subjects with SSc. Subjects are allowed to continue receiving stable standard of care therapies for the management of symptomatic RP (e.g., calcium channel blockers, angiotensin-converting enzyme inhibitors, statins, fluoxetine, and low dose acetylsalicylic acid) or may participate without the use of background standard of care therapies.

The study will target randomizing approximately 180 subjects.

The study consists of an up to 30-day screening period during which subjects will complete a daily ePRO diary to record information regarding all symptomatic RP attacks (e.g., severity of symptoms and duration) and analgesic medication use (prescription and over-the-counter). The up to 30-day screening period consists of a 5-day eligibility period and an up to 25-day baseline ePRO diary completion period (Visit 1):

During the 5-day eligibility period, eligible subjects will have a minimum of 10 symptomatic RP attacks, documented in the ePRO diary, occurring over at least 3 separate days of the 5-day eligibility period.

The baseline ePRO diary completion period is a minimum of 10 days and a maximum of 25 days prior to the day of randomization. While 10 days is the preferred baseline ePRO completion period, it may be necessary to extend the baseline ePRO diary completion period beyond 10 days in order to accommodate the preferred Monday to Friday dosing schedule. All eligible subjects must complete a minimum of 80% of the daily ePRO diary entry during the baseline period. The ePRO symptomatic RP attack data from this time period will be used for the calculation of the baseline frequency of symptomatic RP attacks.

Eligible subjects will be randomized in a 1:1 ratio to iloprost injection for IV use or placebo. Randomization will be stratified based on the use of phosphodiesterase inhibitors at screening. Study drug administration will begin on Day 1 (Visit 2), and subjects will receive study drug for 5 consecutive days (e.g., Monday through Friday) as a continuous IV infusion over 6 hours each day via a peripheral line utilizing the NovaCath™ Integrated IV Catheter System or a peripherally inserted central catheter (PICC) using an infusion pump.

Subjects must have a systolic blood pressure ≥85 mmHg (sitting position) 15 minutes (±15 minutes) prior to study drug administration each day of administration. The weight of the subject at screening may be used to determine the starting flow rate for each subject (see Table 2). If the weight of the subject at screening is used, the weight should be confirmed on Day 1 (Visit 2).

On Day 1 (Visit 2), study drug will be initiated at a starting dose of 0.5 ng/kg/min, and dose increases will occur every 30 minutes (±5 minutes) in increments of 0.5 ng/kg/min up to 2.0 ng/kg/min or the individual tolerated dose. If dose-limiting adverse events (e.g., headache, flushing, jaw pain, myalgia, nausea, or vomiting) occur that cannot be tolerated by the subject, then the dose will be reduced in a stepwise manner by 0.5 ng/kg/min every 30 minutes (±5 minutes), until a tolerated dose is determined. If symptomatic hypotension or a dose-limiting adverse event occurs during administration of study drug at the starting dose (i.e., 0.5 ng/kg/min), the study drug infusion will be discontinued and re-initiation of the study drug infusion can be attempted after the event has resolved or been treated. Blood pressure and heart rate will be obtained 15 minutes (±15 minutes) prior to study drug administration and monitored 15 minutes (=5 minutes) after all up-titrations. If the subject experiences symptomatic hypotension or any other adverse event that cannot be tolerated, as determined by the Investigator, during administration of study drug, the dose will be reduced or the study drug infusion will be stopped until the symptoms resolve, at which point the study drug can be reinitiated at a previously tolerated dose. The maximum tolerated dose will be maintained for the remaining 6-hour daily period. At the end of the 6-hour study drug infusion period, the dose will be stopped. Vital signs will be obtained 15 minutes (±5 minutes) after completion of the study drug infusion.

On Days 2 to 5 (Visit 3 to 6), the study drug infusion will be started using the highest study drug infusion rate tolerated on the previous day without up- or down-titration, unless the subject does not tolerate the study drug infusion or adverse events occur that cannot be tolerated by the subject and necessitate a reduction in the dose (in 0.5 ng/kg/min increments) and subsequent up-titration is allowed to the Day 1 highest tolerated dose. A lower starting dose may be initiated on Days 3 to 5 (Visit 4 to 6) if the subject does not tolerate the previous days' highest tolerated dose as a starting dose. Vital signs will be obtained 15 minutes (=15 minutes) prior to study drug administration and at 15 minutes (±5 minutes) after all up-titrations during the study drug infusion. Additionally, vital signs will be obtained at 15 minutes (±5 minutes) after completion of the 6-hour study drug infusion.

Subjects with hepatic dysfunction (Child-Pugh Class B and Class C liver disease) will require a reduced starting dose (0.25 ng/kg/min) and modified dose titration (0.25 ng/kg/min up to 1.0 ng/kg/min; titrate in a stepwise manner by 0.25 ng/kg/min increments as described above for tolerability).

Study drug will be administered at the site (including decentralized sites) by a trained healthcare professional. Decentralized sites (subject's home or off-site ambulatory infusion sites) is provided by one-on-one home care nurse and overseen by the Investigator. Dosing compliance will be recorded by the Investigator or designee at the investigational site.

Subjects will be contacted via telephone on Day 8 (+2 days) (Visit 7) to remind subjects to continue to complete the daily ePRO diary; subjects will complete the ePRO diary through Day 21. On Day 22 (+2 days) (Visit 8), subjects will be contacted via telephone to assess adverse events and reminded to return to the clinic for the Day 35 visit (+7 days) (Visit 9) for post-treatment evaluations. A follow-up visit will occur 30 days after the last administration of study drug on Day 35 (+7 days) (Visit 9).

Subjects who discontinue study drug early will remain in the study (unless the subject withdraws consent) and complete the daily ePRO diary through Day 21 as well as post-treatment study assessments. A missed or discontinued dose/infusion day (e.g., due to lack of venous access or inability to access the infusion site) does not constitute study drug discontinuation. In this situation, a subject may continue subsequent infusions per protocol. If a subject discontinues (early termination) from the study at any time prior to Day 35 (+7 days) (Visit 9), every attempt should be made to have the subject complete an early termination visit. The reason for subject withdrawal from the study must be documented.

The total duration of the study for a subject will be up to approximately 9 weeks.

Objectives

The primary objective is to evaluate the efficacy of iloprost compared to placebo on the change from baseline in symptomatic digital ischemic episodes, as measured by the weekly frequency of symptomatic Raynaud's Phenomenon (RP) attacks, in subjects with SSc. For the endpoint calculated using data from the ePRO diary, the baseline value will be the (weekly) average of the inputs during the 10- to 25-day baseline ePRO diary completion period, and the post-baseline value will be the (weekly) average of the inputs during Days 8 through 21.

The secondary objectives are the following:
To evaluate the efficacy of iloprost compared to placebo on the overall severity of RP attack symptoms (using a Numeric Rating Scale [NRS]). The symptom (pain, numbness, discomfort, or tingling) with the worst average baseline value for each subject will be used for evaluating the subject's overall severity. If more than 1 symptom has the same value, the symptom used for analysis will be based on the following order of rank: pain>numbness>tingling>discomfort.
To evaluate the efficacy of iloprost compared to placebo on the weekly total duration of symptomatic RP attacks
To evaluate the safety and tolerability of iloprost
The exploratory objectives are the following:
To evaluate the efficacy of iloprost compared to placebo on the worst pain associated with symptomatic RP attacks
To evaluate the efficacy of iloprost compared to placebo on the worst numbness associated with symptomatic RP attacks
To evaluate the efficacy of iloprost compared to placebo on the worst tingling associated with symptomatic RP attacks
To evaluate the efficacy of iloprost compared to placebo on the worst discomfort associated with symptomatic RP attacks
To evaluate the efficacy of iloprost compared to placebo on the Raynaud's Condition Score
To evaluate the efficacy of iloprost compared to placebo on symptomatic RP attack duration
To evaluate the efficacy of iloprost compared to placebo on the patient assessment of overall change in symptomatic Raynaud's attacks (Patient Global Impression of Change [PGIC])
To evaluate the efficacy of iloprost compared to placebo on the patient assessment of overall severity in symptomatic Raynaud's attacks (Patient Global Impression in Severity [PGIS])
To evaluate the patient assessment of overall benefit compared to side effects
To evaluate the effect of iloprost compared to placebo on biomarkers of SSc (optional and at study sites only, not available at decentralized sites)

Dosage Forms and Route of Administration

The study drugs (iloprost injection for IV use and matching placebo) will be supplied in vials packaged in blinded and numbered study drug kits (5 vials per kit). The study drugs (iloprost and placebo) will appear as identical solutions within identical vials, except 100 mcg of iloprost will be added to the active study drug vials. The study drug product must be diluted with sodium chloride 0.9% in a drug reservoir (IV bag) prior to use.

Subjects will receive the study drug IV infusions for 5 consecutive days (e.g., Monday to Friday). Study drug will be administered after dilution as a continuous IV infusion over 6 hours each day via a peripheral line utilizing the NovaCath Integrated IV Catheter System (or a PICC) using an infusion pump.

Study Population

The population for this study is male and female subjects ≥18 years of age with a diagnosis of SSc as defined by the 2013 American College of Rheumatology criteria/European League Against Rheumatism (EULAR) criteria. Eligible subjects with SSc will also be experiencing symptomatic digital ischemic episodes.

Inclusion Criteria
  Male or female subjects must be greater than or equal to 18 years of age.
  Subjects must have a diagnosis of Systemic Sclerosis as defined by the 2013 American College of Rheumatology criteria/EULAR criteria
  Subjects must have a diagnosis or history of Raynaud's Phenomenon, self-reported or reported by a physician, with at least a 2-phase color change in finger(s) of pallor, cyanosis, and/or reactive hyperemia in response to cold exposure or emotion
  Subjects must have a minimum of 10 symptomatic Raynaud's Phenomenon attacks, documented in the electronic patient-reported outcomes (ePRO) diary, occurring over at least 3 separate days of the 3- to 5-day eligibility period
  Subjects must complete a minimum of 80% of the daily ePRO diary entry during the baseline period
  Female subjects of childbearing potential and male subjects must agree to use contraception for the duration of the study.
  Subjects must be willing and able to comply with the study requirements and give informed consent for participation in the study Exclusion Criteria
- Female subjects who are pregnant or breastfeeding
- Subjects with systolic blood pressure <85 mmHg
- Subjects with an estimated glomerular filtration rate <15 mL/min/1.73 m2
- Subjects with an alanine aminotransferase and/or aspartate aminotransferase value >3×the upper limit of normal at screening
- Subjects who have a digital ulcer infection within 30 days of screening
- Subjects with a history of cervical or digital sympathectomy, or botulism toxin injections in their hands [for RP or digital ulcers] within 90 days of screening. Subjects should not have a planned botulism toxin or sympathectomy during their participation in the study.
- Subjects with gangrene or digital amputation within 6 months of screening
- Subjects with current intractable diarrhea or vomiting
- Subjects with a risk of clinically significant bleeding events, including those with coagulation or platelet disorders at screening
- Subjects with a history of major trauma or hemorrhage within 30 days of screening.
- Subjects with clinically significant chronic intermittent bleeding, such as active gastric antral vascular ectasia or active peptic ulcer disease, within 60 days of screening
- Subjects who have had any cerebrovascular events (e.g., transient ischemic attack or stroke) within 6 months of screening
- Subjects with a history of myocardial infarction or unstable angina within 6 months of screening. Subjects should not have a planned coronary procedure during their participation in the study
- Subjects with acute or chronic congestive heart failure (New York Heart Association Class III [moderate] or Class IV [severe]) at screening
- Subjects with a history of more than mild restrictive or congestive cardiomyopathy uncontrolled by medication or implanted device
- Subjects with a history of life-threatening cardiac arrhythmias
- Subjects with a history of hemodynamically significant aortic or mitral valve disease
- Subjects with a history of known pulmonary hypertension, pulmonary arterial hypertension, or pulmonary veno-occlusive disease
- Subjects with a history of significant restrictive lung disease, defined as forced vital capacity <45% predicted and diffusing capacity of the lungs for carbon monoxide <40% predicted (uncorrected for hemoglobin)
- Subjects with scleroderma renal crisis within 6 months of screening
- Subjects with a concomitant life-threatening disease with a life expectancy <12 months
- Subjects who have a clinically significant disorder that, in the opinion of the Investigator, could contraindicate the administration of study drug, affect compliance, interfere with study evaluations, or confound the interpretation of study results
- Subjects who have taken or are currently taking any parenteral, inhaled, or oral prostacyclin or prostacyclin receptor agonists (e.g., epoprostenol, treprostinil, iloprost, and selexipag) within 8 weeks of screening
- Subjects who have initiated or had a dose change of any of the following within 2 weeks of screening: oral, topical, or intravenous (IV) vasodilators (e.g., calcium channel blockers, phosphodiesterase-5 (PDE5) inhibitors [e.g., sildenafil, tadalafil, or vardenafil], nitrates, and fluoxetine)
- Subjects with any history of acetaminophen intolerability (e.g., allergic reaction to acetaminophen)
- Subjects with any malignancy that requires treatment during the study period, that has required treatment within 1 year of screening (including excision of skin cancer) or that is currently not in remission
- Subjects who have used any investigational medication or device for any indication within 30 days or 5 half-lives (whichever is longer)
- Subjects who have participated in study as discussed in Example 1 or Example 2 and were randomized and treated with iloprost Safety Variables Safety parameters will include all adverse events, physical examination findings, vital sign measurements (heart rate and blood pressure), 12-lead electrocardiogram findings, and standard clinical laboratory measurements (chemistry and hematolog Efficacy Assessments Raynaud's Phenomenon Attacks: A symptomatic Raynaud's attack for this study is defined as at least 1 color change of the subject's finger(s) (blue, purple, white, or red) associated with at least 1 symptom (pain, numbness, tingling, and/or discomfort of the finger [s]). The attack is considered over when the color changes back to pre-attack color (normal) and the symptoms return to the subject's pre-attack level.

Electronic Patient-Reported Outcomes Diary: Subjects will be provided with an ePRO diary at Visit 1 and trained on its use. Subjects will be asked to complete the ePRO diary as discussed above. The ePRO diary allows for documentation of frequency, severity, and duration of symptomatic RP attacks and analgesic medication use (prescription and over-the-counter). Specific questionnaires include the severity of RP attack symptoms (using NRS), Raynaud's Condition Score, overall patient improvement, and overall patient severity.

Severity of Raynaud's Phenomenon attack symptoms (using a Numeric Rating Scale): Raynaud's Phenomenon attacks are associated with significant discomfort (pain, numbness, tingling, and/or discomfort). Subjects will be asked to rate the severity of RP attack symptoms (pain, numbness, tingling, and/or discomfort) using an 11-point NRS. Intensity will be assessed as follows: 0=no pain/numbness/tingling/discomfort, 1 to 3=mild pain/numbness/tingling/discomfort, 4 to 6=moderate pain/numbness/tingling/discomfort, and 7 to 10=severe pain/numbness/tingling/discomfort.

Raynaud's Condition Score: The Raynaud's Condition Score asks subjects to rate their difficulty with Raynaud's condition on a given day from "No difficulty (0)" to "Extreme difficulty (10)." Subjects will be asked to consider the number of attacks they have had on that day and how long each attack lasted. Subjects will also be asked to consider how much pain, numbness, or other symptoms the Raynaud's caused in their fingers (including painful sores) and how much the Raynaud's alone affected the use of their hands that day.

Worst pain associated with Raynaud's Phenomenon attacks (using a Numeric Rating Scale): Raynaud's Phenomenon attacks are associated with significant pain. Subjects will be asked to rate the worst pain associated with RP attacks using an 11-point NRS. Intensity will be assessed as follows: 0=no pain, 1 to 3=mild pain, 4 to 6=moderate pain, and 7 to 10=severe pain.

Weekly total duration of symptomatic Raynaud's Phenomenon attacks: Subjects will be asked to document the duration of each symptomatic RP attack within their ePRO diaries. For each attack, the subject will record the duration in minutes. The weekly total duration of symptomatic RP attacks is the cumulative duration of all attacks calculated on weekly basis.

Duration of Raynaud's Phenomenon attacks: Subjects will be asked to document the duration of each symptomatic RP attack within their ePRO diaries. For each attack, the subject will record the duration in minutes. The weekly total duration of symptomatic RP attacks is the cumulative duration of all attacks calculated on weekly basis.

Overall patient improvement: At Day 21 (+2 days), subjects will be asked to rate their overall improvement in symptomatic Raynaud's attacks compared to the start of the study. Overall improvement in symptomatic Raynaud's attacks will be assessed on a 7-point scale from very much better to very much worse.

Overall patient severity: At Day 1 (prior to initiating study drug), subjects will be asked to rate their overall severity in symptomatic Raynaud's attacks in the last week. At Day 21 (+2 days), subjects will be asked to rate their overall severity in symptomatic Raynaud's attacks. Overall severity of symptomatic Raynaud's attacks will be assessed on a 5-point scale from none to very severe.

Patient benefit: At Day 21 (+2 days), subjects will be asked if the study drug provided a meaningful benefit compared to any side effects, which the subject can answer Yes or No.

Sensitivity Analysis: A sensitivity analysis is performed to test the robustness of the endpoint and to assess the impact of using a rank order of symptoms to determine which symptom is used when more than 1 symptom has the same baseline numeric rating system (NRS). When there are multiple symptoms with the same worst average (highest NRS) baseline value for a patient, one of these symptoms is randomly selected to evaluate the patient's overall severity instead of using the order of rank. Numbers 1, 2, 3 and 4 are randomly assigned to the four symptoms for each patient (different patients may have different numbers assigned to the same symptom). When there are multiple symptoms with the same worst average baseline value for a patient, the one with the largest number (among these symptoms) is used to evaluate the overall severity of this patient. Random seed=536512 is used for the random assignment.

Example 3. Solution Stability of Fully Diluted Ready-to-Use Iloprost

Iloprost 100 µg/mL injection product is administered to patients by IV bag infusion over a period of six hours. The fully diluted ready to use iloprost is prepared in pharmacy cleanroom using sterile preparation standards (USP Chapter <797>) by pharmacy trained and licensed staff. The fully diluted ready to use drug product may be prepared several hours ahead of treatment with storage at ambient conditions or several days ahead of treatment with storage at refrigerated (2-8° C.) conditions. The IV bags are prepared using empty sterile IV bags which are filled with 99 mL of 0.9% NaCl and 1.0 mL of iloprost 100 g/mL injection product. The bags are then manually mixed gently to provide a uniform solution.

Administration IV bags were prepared and stored at several conditions with routine sampling for assay testing for stability under i) 25° C./60% RH, ii) 5° C. for 5 days to 25° C./60% RH, iii) 5° C. for 8 days to 25° C./60% RH.

IV Bag Sample Preparation: Two 50 mL syringes with 18-gauge needles were assembled. 1.0 mL syringe with 18-gauge needle was assembled. Using a 50 mL syringe, 50 mL of 0.9% NaCl was transferred into an empty IV bag (sterile, ICU Medical) using the injection port. Using a second 50 mL syringe, 49 mL of 0.9% NaCl was transferred into the same IV bag using the injection port resulting in 99 mL of solution. Using the 1 ml syringe, 1.0 mL of iloprost 100 µg/mL injection product was transferred into the IV bag using the injection port. The needle was removed and the port was securely closed. The IV bag was gently inverted several times to mix. During inversion, it was occasionally paused to squeeze the injection port area to ensure liquid rinsed into area several times.

Sampling Procedure: For sampling, a 3 mL syringe was assembled with an 18-gauge needle. Using a 3 ml syringe, 2 mL of IV bag solution was withdrew through the injection port and 1 mL was transferred to a HPLC vial for neat injection and the other 1 ml was transferred to a back-up HPLC vial. HPLC vials were stored at refrigerated conditions 2-8° C.

Sample Storage and Sampling: For each testing conditions (i-iv discussed above), 12 IV bag samples were prepared (6 IV bags for condition ia)—see below for sampling time). For condition i), all 12 IV bags were then placed into 25° C./60% RH stability chamber ensuring each bag is resting on its largest surface area side. After the first time point, the IV bags were removed from the chamber and each IV bag was mixed by inversion several times. Sampling from each IV bag was taken for HPLC analysis. After sampling, the IV bags were placed back into 25° C./60% RH stability chamber ensuring each bag is resting on its largest surface area side, until next sampling time. At each sampling time, the IV bags were removed from the chamber and each IV bag was mixed by inversion several times before samples were removed.

For conditions ii) and iii), all 12 IV bags for each testing condition was placed into a 2-8° C. stability chamber ensuring each bag is resting on its largest surface area side. After 5 days have passed for condition ii) or after 8 days have passed for condition iii), the IV bags were removed from the chamber and allowed to equilibrate to room temperature. Each IV bag was mixed by inversion several times. Sampling from each IV bag was taken for HPLC analysis. Then the IV bags were placed in the 25° C./60% RH stability chamber and sampled at certain time points as discussed herein.

Sampling time for condition ia): 2 h, 4 h, 6 h, 8 h, and 24 h

Sampling time for ib): 8 h, 12 h, 48 h, and 96 h

Sampling time for condition ii): 5 days (at the end of storage in 2-8° C. stability chamber), 5 days and 8 h, and 5 days and 12 h Sampling time for condition iii): 8 days (at the end of storage in 2-8° C. stability chamber), 8 days and 8 h, and 8 days and 12 h Sample Analysis: Samples were analyzed by HPLC using a validated method (validation protocol not shown).

| | |
|---|---|
| HPLC Column: | Waters Spherisorb ODS-2, 125 mm, × 4.6 mm, 3 μm, P/N PSS832116 |
| Column Temperature: | 20° C. |
| Sample Temperature: | 5° C. |
| Flow Rate: | 1.0 mL/min |
| Injection Volume: | 100 μL |
| UV (DAD or MWD): | 200 nm, bandwidth 4 nm; Identification by UV Spectrum 200-400 nm |
| UV (VWD): | 200 nm |
| Run Time: | 55 Minutes |
| Needle Rinse: | (75:25 Milli-Q ™ Water:ACN) |
| Mobile Phase A: | (8 g/L BCD in 33% ACN, pH 2.0) |
| Mobile Phase B: | (50:50:0.1 Milli-Q ™ Water:ACN:H3PO4) |

| Gradient: | Time (minutes) | % Mobile Phase A | % Mobile Phase B |
|---|---|---|---|
| | 0 | 100 | 0 |
| | 30 | 100 | 0 |
| | 35 | 5 | 95 |
| | 50 | 5 | 95 |
| | 50.1 | 100 | 0 |
| | 55 | 100 | 0 |

The concentration of each sample per the equation below:

$$\text{Sample Concentration} (\mu g/mL) = \frac{Rsam}{Rstd} \times Cstd(mg/mL) \times \frac{Vpip(mL)}{Vstd(mL)} \times 1000 \, \mu g/mg$$

Rstd=Average sum of the areas of the Iloprost peaks from five Standard Solution injections made during system suitability.

Rsam=Sum of the areas of the Iloprost peaks from the sample solution injection

Cstd (mg/mL)=Concentration of Iloprost Stock Standard Solution in mg/mL

Vstd (mL)=Volume of Standard Solution in mL (10 mL)

Vpip (mL)=Volume of Iloprost Stock Standard Solution pipetted into the Standard Solution in mL (0.1 mL)

The % Initial (initial concentration) of each stored sample was determined per the equation below:

$$\% \text{ Initial} = \frac{\text{Stored Sample Concentration} (\mu g/mL)}{\text{Initial} (T=0) \text{ SampleConcentration} (\mu g/mL)} \times 100$$

The results from the IV Bag stability study under condition ia (25° C./60% RH stability; sample time 2 h, 4 h, 6 h, 8 h, and 24 h) are presented in Table 8A. The % initial results for all of the IV bag preparations exhibited a range of 94.2-94.9%. These results were as expected from the nature of the IV bag preparation which was designed to mimic the clinical procedure. The IV bags were adjusted for volume to a target weight and then spiked with drug product using a disposable sterile 1 ml syringe equipped with a disposable sterile 18 gauge needle. A combination of variability in the weight of the IV bags and variability in the volume accuracy of the syringes and needles was expected to affect the accuracy of the spiking procedure. Each sample met the specification criterion of 90.0-110.0% and each stored sample was also within 90.0-110.0% of the initial result for the preparation.

TABLE 8A 24 hour stability at 25° C./60% RH

| Sample No. | Time-point (h) | Iloprost (%) | % Initial |
|---|---|---|---|
| 1 | Initial | 94.9 | |
| | 2 | 95.3 | 100.4 |
| | 4 | 96.7 | 101.9 |
| | 6 | 95.4 | 100.6 |
| | 8 | 94.8 | 99.9 |
| | 24 | 97.0 | 102.2 |
| 2 | Initial | 94.2 | |
| | 2 | 95.0 | 100.8 |
| | 4 | 95.2 | 101.0 |
| | 6 | 95.7 | 101.6 |
| | 8 | 94.3 | 100.0 |
| | 24 | 95.5 | 101.4 |
| 3 | Initial | 94.8 | |
| | 2 | 94.2 | 99.4 |
| | 4 | 94.3 | 99.5 |
| | 6 | 95.0 | 100.2 |
| | 8 | 94.8 | 100.0 |
| | 24 | 96.7 | 102.0 |
| 4 | Initial | 94.6 | |
| | 2 | 94.8 | 100.2 |
| | 4 | 94.3 | 99.6 |
| | 6 | 95.1 | 100.5 |
| | 8 | 94.6 | 100.0 |
| | 24 | 94.7 | 100.1 |
| 5 | Initial | 94.4 | |
| | 2 | 94.2 | 99.7 |
| | 4 | 94.7 | 100.3 |
| | 6 | 93.7 | 99.3 |
| | 8 | 96.2 | 101.9 |
| | 24 | 93.4 | 98.9 |
| 6 | Initial | 94.3 | |
| | 2 | 94.7 | 100.5 |
| | 4 | 95.5 | 101.3 |
| | 6 | 95.9 | 101.7 |
| | 8 | 95.3 | 101.1 |
| | 24 | 94.8 | 100.5 |

The results from the IV Bag stability study under condition ib (25° C./60% RH stability; sample time 8 h, 12 h, 48 h, and 96 h) are presented in Tables 8B and 8C. Each sample met the specification criterion of 90.0-110.0% and each stored sample was also within 90.0-110.0% of the initial result for the preparation.

TABLE 8B 96 hour stability at 25° C./60% RH (Batch 1)

| Time Point | Preparation | Iloprost (ng/mL) | % Initial |
|---|---|---|---|
| Initial (T = 0) | 1 | 977.49068 | — |
| | 2 | 968.66746 | |
| | 3 | 942.80790 | |
| | 4 | 994.14641 | |
| | 5 | 981.91733 | |
| | 6 | 975.78016 | |
| 8 hr | 1 | 973.57406 | 100 |
| | 2 | 1009.87852 | 104 |
| | 3 | 979.46989 | 104 |
| | 4 | 1002.63999 | 101 |
| | 5 | 977.22453 | 100 |
| | 6 | 1007.06584 | 103 |
| 12 hr | 1 | 1004.19286 | 103 |
| | 2 | 1008.58278 | 104 |
| | 3 | 978.15686 | 104 |
| | 4 | 1042.47061 | 105 |
| | 5 | 975.06820 | 99 |
| | 6 | 1005.44196 | 103 |

TABLE 8B-continued 96 hour stability at 25° C./60% RH (Batch 1)

| Time Point | Preparation | Iloprost (ng/mL) | % Initial |
|---|---|---|---|
| 48 hr | 1 | 1003.58363 | 103 |
| | 2 | 995.23565 | 103 |
| | 3 | 968.03688 | 103 |
| | 4 | 1001.02390 | 101 |
| | 5 | 984.61614 | 100 |
| | 6 | 977.30241 | 100 |
| 96 hr | 1 | 1013.28284 | 104 |
| | 2 | 1017.49428 | 105 |
| | 3 | 970.92026 | 103 |
| | 4 | 1014.14964 | 102 |
| | 5 | 994.07339 | 101 |
| | 6 | 971.53175 | 100 |

TABLE 8C 96 hour stability at 25° C./60% RH (Batch 2)

| Time Point | Preparation | Iloprost (ng/mL) | % Initial |
|---|---|---|---|
| Initial (T = 0) | 1 | 980.86863 | — |
| | 2 | 990.69772 | |
| | 3 | 980.65678 | |
| | 4 | 994.36439 | |
| | 5 | 1000.53816 | |
| | 6 | 1020.67367 | |
| 8 hr | 1 | 995.76595 | 102 |
| | 2 | 1002.10267 | 101 |
| | 3 | 994.55360 | 101 |
| | 4 | 1003.76351 | 101 |
| | 5 | 998.77363 | 100 |
| | 6 | 983.28166 | 96 |
| 12 hr | 1 | 993.30159 | 101 |
| | 2 | 984.11952 | 99 |
| | 3 | 984.12486 | 100 |
| | 4 | 989.62285 | 100 |
| | 5 | 994.77764 | 99 |
| | 6 | 1004.99733 | 98 |
| 48 hr | 1 | 993.66797 | 101 |
| | 2 | 984.23731 | 99 |
| | 3 | 994.36502 | 101 |
| | 4 | 1031.78023 | 104 |
| | 5 | 1005.03600 | 100 |
| | 6 | 1014.71909 | 99 |
| 96 hr | 1 | 1002.16769 | 102 |
| | 2 | 979.52872 | 99 |
| | 3 | 988.97656 | 101 |
| | 4 | 1004.97292 | 101 |
| | 5 | 996.34817 | 100 |
| | 6 | 1027.43687 | 101 |

The results from the IV Bag stability study under condition ii (5° C. for 5 days to 25° C./60% RH) are presented in Tables 8D and 8E. Each sample met the specification criterion of 90.0-110.0% and each stored sample was also within 90.0-110.0% of the initial result for the preparation.

TABLE 8D

5° C. for 5 days to 25° C./60% RH (Batch 1)

| Time Point | Preparation | Iloprost (ng/mL) | % Initial |
|---|---|---|---|
| Initial (T = 0) | 1 | 1007.32936 | — |
| | 2 | 953.59154 | |
| | 3 | 1014.73720 | |
| | 4 | 1019.54404 | |
| | 5 | 1036.25326 | |
| | 6 | 996.56811 | |
| 5° C. for 5 days | 1 | 1049.58766 | 104 |
| | 2 | 931.91928 | 98 |
| | 3 | 1023.92132 | 101 |

TABLE 8D-continued

5° C. for 5 days to 25° C./60% RH (Batch 1)

| Time Point | Preparation | Iloprost (ng/mL) | % Initial |
|---|---|---|---|
| | 4 | 1020.05717 | 100 |
| | 5 | 1024.17465 | 99 |
| | 6 | 1000.90608 | 100 |
| 5° C. for 5 days 25° C./60% RH for 8 hr | 1 | 1002.17085 | 99 |
| | 2 | 957.27263 | 100 |
| | 3 | 993.78991 | 98 |
| | 4 | 1040.15942 | 102 |
| | 5 | 1025.38946 | 99 |
| | 6 | 1010.55688 | 101 |
| 5° C. for 5 days 25° C./60% RH for 12 hr | 1 | 976.52119 | 97 |
| | 2 | 943.23563 | 99 |
| | 3 | 1015.06188 | 100 |
| | 4 | 1030.59268 | 101 |
| | 5 | 1010.05028 | 97 |
| | 6 | 982.68256 | 99 |

TABLE 8E

5° C. for 5 days to 25° C./60% RH (Batch 2)

| Time Point | Preparation | Iloprost (ng/mL) | % Initial |
|---|---|---|---|
| Initial (T = 0) | 1 | 1011.00891 | — |
| | 2 | 986.02971 | |
| | 3 | 1021.90645 | |
| | 4 | 1021.61212 | |
| | 5 | 1001.14785 | |
| | 6 | 988.43978 | |
| 5° C. for 5 days | 1 | 1026.46301 | 102 |
| | 2 | 1008.56452 | 102 |
| | 3 | 1024.57969 | 100 |
| | 4 | 1029.90237 | 101 |
| | 5 | 1011.12281 | 101 |
| | 6 | 987.37008 | 100 |
| 5° C. for 5 days 25° C./60% RH for 8 hr | 1 | 1023.49747 | 101 |
| | 2 | 973.07617 | 99 |
| | 3 | 1013.01926 | 99 |
| | 4 | 1011.71269 | 99 |
| | 5 | 996.65926 | 100 |
| | 6 | 970.82806 | 98 |
| 5° C. for 5 days 25° C./60% for 12 hr | 1 | 1022.38730 | 101 |
| | 2 | 963.28102 | 98 |
| | 3 | 1001.36417 | 98 |
| | 4 | 1003.23343 | 98 |
| | 5 | 1016.70001 | 102 |
| | 6 | 985.93577 | 100 |

The results from the IV Bag stability study under condition iii (5° C. for 8 days to 25° C./60% RH) are presented in Tables 8F and 8G. Each sample met the specification criterion of 90.0-110.0% and each stored sample was also within 90.0-110.0% of the initial result for the preparation.

TABLE 8F

5° C. for 8 days to 25° C./60% RH (Batch 1)

| Time Point | Preparation | Iloprost (ng/mL) | % Initial |
|---|---|---|---|
| Initial (T = 0) | 1 | 970.11915 | — |
| | 2 | 966.13069 | |
| | 3 | 989.59242 | |
| | 4 | 959.55241 | |
| | 5 | 964.81219 | |
| | 6 | 957.61598 | |
| 5° C. for 5 days | 1 | 994.43539 | 103 |
| | 2 | 953.18657 | 99 |
| | 3 | 978.41500 | 99 |
| | 4 | 953.14379 | 99 |
| | 5 | 984.18557 | 102 |
| | 6 | 956.73023 | 100 |

TABLE 8F-continued

5° C. for 8 days to 25° C./60% RH (Batch 1)

| Time Point | Preparation | Iloprost (ng/mL) | % Initial |
|---|---|---|---|
| 5° C. for 8 days 25° C./60% RH for 8 hr | 1 | 963.52003 | 99 |
| | 2 | 955.94360 | 99 |
| | 3 | 967.83409 | 98 |
| | 4 | 938.70012 | 98 |
| | 5 | 1032.99481 | 107 |
| | 6 | 961.84780 | 100 |
| 5° C. for 8 days 25° C./60% RH for 12 hr | 1 | 980.47291 | 101 |
| | 2 | 964.06225 | 100 |
| | 3 | 986.44359 | 100 |
| | 4 | 967.53103 | 101 |
| | 5 | 964.22470 | 100 |
| | 6 | 952.01922 | 99 |

TABLE 8G

5° C. for 8 days to 25° C./60% RH (Batch 2)

| Time Point | Preparation | Iloprost (ng/mL) | % Initial |
|---|---|---|---|
| Initial (T = 0) | 1 | 979.57170 | — |
| | 2 | 983.59476 | |
| | 3 | 998.93472 | |
| | 4 | 1008.63220 | |
| | 5 | 1025.59384 | |
| | 6 | 992.74821 | |
| 5° C. for 5 days | 1 | 970.13301 | 99 |
| | 2 | 957.91301 | 97 |
| | 3 | 1019.54124 | 102 |
| | 4 | 1006.94224 | 100 |
| | 5 | 993.60327 | 97 |
| | 6 | 1014.48560 | 102 |
| 5° C. for 8 days 25° C./60% RH for 8 hr | 1 | 983.93098 | 100 |
| | 2 | 964.53372 | 98 |
| | 3 | 1004.08143 | 101 |
| | 4 | 997.60330 | 99 |
| | 5 | 1010.96396 | 99 |
| | 6 | 1010.24659 | 102 |
| 5° C. for 8 days 25° C./60% RH for 12 hr | 1 | 967.45808 | 99 |
| | 2 | 964.40986 | 98 |
| | 3 | 1006.95543 | 101 |
| | 4 | 1011.04730 | 100 |
| | 5 | 1012.62453 | 99 |
| | 6 | 1008.92483 | 102 |

During the study, three unknown peaks in chromatograms were observed; however, all of these unknown peaks were present in control or stressed blank IV bag samples indicating that all unknown peaks were IV bag or saline related and were not caused by Iloprost drug product. The unknown peaks did not interfere with quantitation of Iloprost peaks and therefore the administration stability study is not considered to be impacted by the presence of the peaks.

These results indicate that the iloprost drug product exhibits suitable stability in the IV bags to support IV bag treatment and administration design.

Example 4. Study of Microbial Attribute of Iloprost 100 g/mL Injection Formulation The aim of this in-use stability study is to provide data reflecting the microbiological quality of iloprost 100 g/mL injection formulation and iloprost placebo injection formulation after their preparation and storage under controlled storage conditions for a specific period of time. These formulation preparation and storage simulates their preparation and storage conditions in compounding pharmacy prior to patient administration.

Iloprost 100 µg/mL injection formulation and iloprost placebo injection formulation samples are prepared (diluted in saline IV bags), stored under controlled conditions and tested at specific time points (day 0, day 10, and day 16). The prepared samples are assessed side-by-side with prepared samples that have been inoculated with a low level of bioburden (10-100 CFU/mL). The low level of bioburden is intended to simulate a microbial contamination at the time of container closure penetration. This microbial challenge study helps determine if the diluted ready to use products have any growth-promoting properties. Growth-promoting properties of these two drug products are assessed according to the USP <51>guidance.

Microbial counts of the inoculated products at time zero is compared to their microbial counts at day 10 and day 16. If the microbial counts on day 10 and day 16 are not higher than 0.5 log 10 unit compared to the starting microbial counts then, the drug products are considered non-growth-promoting and the storage conditions (time and temperature) are deemed appropriate for ensuring that the diluted ready to use drug products are safe.

This in-use stability study is designed and executed per the following guidelines:
- The current United States Pharmacopeia General Chapters USP <51>, "Antimicrobial Effectiveness testing"
- The CDER guidance on the subject by Metcalfe John W. (2009)
- The CDER Microbiology Issues: A deep Dive by Candace Gomez-Broughton, "Aseptic Processing of Biological Products: Current Regulatory Issues", August 2018
- The World Health Organization guidance on the subject: WHO Technical Report Series, No. 863, 1996, Annex 5
- The procedures outlined in this protocol Scope: This protocol applies to microbiological testing in support of the microbiological stability of the diluted ready to use iloprost 100 µg/mL injection formulation and iloprost placebo injection formulation. The stability of these two drug products are assessed after penetration of the container and closure system for dose preparation and storage under controlled conditions. The preparation and storage conditions of the two drug products simulate the preparation and storage prior to patient administration. This protocol describes the study design and Bioburden testing using representative samples of iloprost 100 µg/mL injection formulation and iloprost placebo injection formulation samples.

Interpretation of Results: Initial microbial count (CFU/mL) for each inoculated sample is defined as the microbial count of that sample at time zero and determined by filtration test method. Growth or its absence thereof for a sample/microorganism combination at a specific time point is assessed in relation to time zero. Microbial count is determined for each microorganism at time zero and the log 10 of that microbial count will be calculated. Microbial count for each test sample will be determined at the specific time point, log 10 of that microbial count is calculated and compared to its microbial count log 10 value at time zero. If the difference between the two log 10 values is not more than half log 10 unit, the sample is not displaying microbial growth increase.

Iloprost 100 µg/mL injection formulation preparation: Two 50 mL syringes with 18-gauge needles are assembled. 1.0 ml syringe with 18-gauge needle is assembled. Using a 50 mL syringe, 49 mL of 0.9% NaCl is transferred into an empty IV bag using the injection port. Using a second 50 mL syringe, 50 mL of 0.9% NaCl is transferred into the same IV bag using the injection port. Using the 1 mL syringe, 1.0 mL of iloprost 100 µg/mL injection product is transferred into the IV bag using the injection port. The needle was removed and the port was securely closed. The IV bag is gently inverted several times to mix. During inversion, occasionally paused to squeeze the injection port area to ensure liquid rinsed into area several times. Prepare total of 7 IV bags by this method.

Microbial Inoculation

*S. aureus, B. subtilis, P. aeruginosa, C. albicans, A. brasiliensis,* and *E. coli* are used. Patheon frozen cultures, freshly harvested suspensions, or enumerated lyophilized microorganism preparations are used. Microorganisms that are not more than five passages removed from the master seed lot are used.

Test Samples: Using the appropriate syringe size and an 18-gauge needle, inoculate (inject through injection port) each IV bag and each IV bag of positive control with the appropriate microorganism suspension so that the inoculated IV bag contains between 5-10 CFU/mL (for a total of 500 to 1000 CFU/IV bag). Gently invert each IV bag several times to mix. During inversion, pause occasionally to squeeze the injection port area to ensure liquid rinses into area several times.

Inoculum Verification (perform in duplicate for each microorganism at time zero): Add 1 mL from each positive control sample to each of two 100×15 mm Petri dishes. Pour approximately 25 mL Letheen agar cooled to ≤45° C. into each of two Petri dishes and swirl to mix. Allow the agar to solidify and invert the plates to incubate. Incubate the bacteria plates at 30 to 35° C. for 3-5 days. Incubate Candia albicans plates at 20-25° C. for 3 to 5 days, and incubate the Aspergillus brasiliensis plates at 20-25° C. for 3 to 7 days.

Sampling: Day 0 samples are taken immediately after the IV bags were prepared. Test samples are taken after 10 days and 16 days storage of the inoculated bags at 2-8° C. At the specified time point, assemble a 50 mL syringe with 18-gauge needle. Using the 50 mL syringe, withdraw 25 mL from each of the inoculated IV bags through the injection port and transfer to an appropriate size sterile test tube with cap. After taking the test samples, place the inoculated IV bags at 2-8° C. until the next sampling time point.

Testing Samples: Test the inoculated product samples, positive controls, product negative controls (iloprost and diluent), and diluent negative control. Each sample is tested in duplicate (two filters will be used). Prewash each of two sterile filter membranes with 100 mL Dilution Fluid D. Add a 10 mL aliquot of the test sample (inoculated drug product, product negative control, positive control or diluent negative control) to each filter unit and filter through. Wash each filter with 3×100 mL aliquots of Dilution Fluid D. Aseptically transfer the two filters to two separate Letheen Agar plates. Allow the agar to solidify and incubate as follows:
 a. The inoculated product samples, and the positive control samples containing bacteria at 30 to 35° C. for 3 to 5 days.
 b. The inoculated product samples, and the positive control samples containing Candia albicans at 20-25° C. for 3 to 5 days
 c. The inoculated product samples, and the positive control samples containing Aspergillus brasiliensis at 20-25° C. for 3 to 7 days.
 d. The product and diluent negative controls: From each set, incubate one plate at 30-35° C. and one plate at 20-25° C. for as long as the test samples but not more than 7 days.

Rinse Fluid Negative Controls: Add 100 mL Dilution Fluid D to each of 2 sterile filter units and filter through. Aseptically transfer the two filters to two plates of Letheen agar. Incubate one plate at 30-35° C. and the other plate at 20-25° C. for as long as the test samples but not more than 7 days.

Agar Negative Controls: Incubate one plate of Letheen agar at 30-35° C. and the other plate at 20-25° C. for as long as the test samples but not more than 7 days.

Analysis: Count the Colony Forming Units (CFU) on each plate per SOP-QC-280 and calculate the arithmetic mean for each set of two plates. Calculate the percent recovery by dividing the mean of the product plate counts (CFU) by the mean of the positive control plate counts (CFU). Multiply by 100 and round to the nearest whole number.

$$\% \text{ Recovery} = \frac{\text{Mean of inoculated Product plates count}(CFU) \times 100}{\text{Mean of inoculated positive controls plates count}(CFU)}$$

Acceptance Criteria

The percent recovery of the product test plates, at time zero, should be at least 50% of the positive controls mean. If lower recoveries (less than 50%) are observed, modify the method in order to overcome inhibition by utilizing one or more of the following:
 Incorporate neutralizing/dispersing agents into the plating medium or rinse fluid
 Utilize different media
 Each inoculum verification plate must have ≥ 1 CFU and ≤100 CFU There must be no growth on the agar and rinse fluid negative controls. A media or rinse fluid negative control failure requires an investigation to evaluate the impact to the testing described herein.

Results

Microbial Enumeration Test Method Suitability. Suitability of the microbial enumeration test method was assessed at time zero by comparing the microbial recoveries from the diluted-ready-to use products to the microbial recoveries from the diluent (positive control). The method was considered suitable if the following criteria were met:
 11. Each inoculum verification plate must have ≥1 CFU and ≤100 CFU
 2. There must be no growth on the product negative controls, agar negative controls and rinse fluid negative controls.
 3. The microbial recovery from the diluted-ready-to use products is at least 50% of the recovery from the diluent (positive control)

Each of the inoculum verification plate (*S. aureus, B. subtilis, P. aeruginosa, C. albicans, A. brasiliensis,* and *E. coli*) counts met the acceptance criteria: ≥1 and ≤100 CFU. All media, diluent and dilution fluid D negative controls exhibited no growth. All product negative controls exhibited no growth.

The recoveries of *S. aureus, B. subtilis, P. aeruginosa, C. albicans, A. brasiliensis,* and *E. coli* from iloprost 100 μg/mL injection formulation and iloprost placebo injection formulation samples, respectively, were all above 50% of the positive control recovery.

Assessment of growth-promoting properties of iloprost 100 kg/mL injection formulation and iloprost placebo injection formulation samples. Microbial counts were determined for each sample/microorganism combination at each time point, and the log 10 of the microbial count mean was calculated. The difference between the log 10 value (time X and time zero) was used to assess if the product is growth-promoting or not. The products were deemed non-growth promoting as assessed by this testing if the following criteria were met:

1. In accordance to USP <51>, for each tested microorganism there must be no microbial count increase that is higher than 0.5 log 10 relative to microbial counts at time zero.
2. There must be no growth on the product negative controls, agar negative controls and rinse fluid negative controls.

Results for each microorganism are summarized in the Tables 9A-9F.

$Log_{10}$ difference = $log_{10}$ value at time $X$ - $log_{10}$ value at time 0

For each of S. aureus, B. subtilis, P. aeruginosa, C. albicans, A. brasiliensis, and E. coli, the $log_{10}$ difference for each time point was not greater than 0.5 log 10 unit from time zero. Ready-to use iloprost 100 µg/mL injection formulation and iloprost placebo injection formulation do not promote S. aureus, B. subtilis, P. aeruginosa, C. albicans, A. brasiliensis, and E. coli growth when stored at 2-8° C. for up to 16 days.

The results presented in Tables 9A-9F show that the tested ready-to use iloprost 100 µg/mL injection formulation and iloprost placebo injection formulation do not display any growth-promoting properties towards the tested microorganisms: S. aureus, B. subtilis, P. aeruginosa, C. albicans, A. brasiliensis, and E. coli. This test meets the acceptance criteria for the assessment of growth-promoting properties of both iloprost 100 µg/mL injection formulation and iloprost placebo injection formulation.

TABLE 9A $Log_{10}$ comparison for A. brasiliensis

| Batch | Time point | Mean Microbial Count (CFU) | $Log_{10}$ of Microbial Count | Log difference compared to Time 0 |
|---|---|---|---|---|
| 1 | Day 0 | 50 | 1.6990 | |
| | Day 10 | 45 | 1.6532 | −0.0458 |
| | Day 16 | 47 | 1.6721 | −0.0269 |
| 2 | Day 0 | 47 | 1.6721 | |
| | Day 10 | 50 | 1.6990 | 0.0269 |
| | Day 16 | 47 | 1.6721 | 0 |
| 3 | Day 0 | 44 | 1.6435 | |
| | Day 10 | 57 | 1.7559 | 0.1124 |
| | Day 16 | 48 | 1.6812 | 0.0377 |
| 4 | Day 0 | 48 | 1.6812 | |
| | Day 10 | 45 | 1.6532 | −0.0280 |
| | Day 16 | 59 | 1.7709 | 0.0897 |

TABLE 9B $Log_{10}$ comparison for C. albicans

| Batch | Time point | Mean Microbial Count (CFU) | $Log_{10}$ of Microbial Count | Log difference compared to Time 0 |
|---|---|---|---|---|
| 1 | Day 0 | 30 | 1.4771 | |
| | Day 10 | 5 | 0.6990 | −0.7781 |
| | Day 16 | 1 | 0 | −1.4771 |
| 2 | Day 0 | 48 | 1.6812 | |
| | Day 10 | 2 | 0.3010 | −1.3802 |
| | Day 16 | 1 | 0 | −1.6812 |
| 3 | Day 0 | 44 | 1.6435 | |
| | Day 10 | 2 | 0.3010 | −1.3425 |
| | Day 16 | 0 | No growth | N/A |
| 4 | Day 0 | 38 | 1.5798 | |
| | Day 10 | 1 | 0 | −1.5798 |
| | Day 16 | 1 | 0 | −1.5798 |

TABLE 9C.

$Log_{10}$ comparison for E. coli

| Batch | Time point | Mean Microbial Count (CFU) | $Log_{10}$ of Microbial Count | Log difference compared to Time 0 |
|---|---|---|---|---|
| 1 | Day 0 | 61 | 1.7853 | |
| | Day 10 | 26 | 1.4150 | −0.3703 |
| | Day 16 | 16 | 1.2041 | −0.5812 |
| 2 | Day 0 | 58 | 1.7634 | |
| | Day 10 | 30 | 1.4771 | −0.2863 |
| | Day 16 | 12 | 1.0792 | −0.6842 |
| 3 | Day 0 | 32 | 1.5051 | |
| | Day 10 | 12 | 1.0792 | −0.4259 |
| | Day 16 | 9 | 0.9542 | −0.5509 |
| 4 | Day 0 | 73 | 1.8633 | |
| | Day 10 | 22 | 1.3424 | −0.5209 |
| | Day 16 | 11 | 1.0414 | −0.8219 |

TABLE 9D $Log_{10}$ comparison for P. aeruginosa

| Batch | Time point | Mean Microbial Count (CFU) | $Log_{10}$ of Microbial Count | Log difference compared to Time 0 |
|---|---|---|---|---|
| 1 | Day 0 | 31 | 1.4914 | |
| | Day 10 | 0 | No growth | N/A |
| | Day 16 | 0 | No growth | N/A |
| 2 | Day 0 | 26 | 1.4150 | |
| | Day 10 | 1 | 0 | −1.4150 |
| | Day 16 | 0 | No growth | N/A |
| 3 | Day 0 | 25 | 1.3979 | |
| | Day 10 | 1 | 0 | −1.3979 |
| | Day 16 | 0 | No growth | N/A |
| 4 | Day 0 | 33 | 1.5185 | |
| | Day 10 | 0 | No growth | N/A |
| | Day 16 | 0 | No growth | N/A |

TABLE 9E $Log_{10}$ comparison for S. aureus

| Batch | Time point | Mean Microbial Count (CFU) | $Log_{10}$ of Microbial Count | Log difference compared to Time 0 |
|---|---|---|---|---|
| 1 | Day 0 | 48 | 1.6812 | |
| | Day 10 | 16 | 1.2041 | −0.4771 |
| | Day 16 | 8 | 0.9031 | −0.7781 |
| 2 | Day 0 | 39 | 1.5911 | |
| | Day 10 | 18 | 1.2553 | −0.3358 |
| | Day 16 | 3 | 0.4771 | −1.114 |

TABLE 9E-continued

Log$_{10}$ comparison for *S. aureus*

| Batch | Time point | Mean Microbial Count (CFU) | Log$_{10}$ of Microbial Count | Log difference compared to Time 0 |
|---|---|---|---|---|
| 3 | Day 0 | 52 | 1.7160 | |
| | Day 10 | 15 | 1.1761 | −0.5399 |
| | Day 16 | 6 | 0.7782 | −0.9378 |
| 4 | Day 0 | 51 | 1.7076 | |
| | Day 10 | 20 | 1.3010 | −0.4066 |
| | Day 16 | 2 | 0.3010 | −1.4066 |

TABLE 9F

Log$_{10}$ comparison for *B. subtilis*

| Batch | Time point | Mean Microbial Count (CFU) | Log$_{10}$ of Microbial Count | Log difference compared to Time 0 |
|---|---|---|---|---|
| 1 | Day 0 | 67 | 1.8261 | |
| | Day 10 | 32 | 1.5051 | −0.3210 |
| | Day 16 | 15 | 1.1761 | −0.6500 |
| 2 | Day 0 | 68 | 1.8325 | |
| | Day 10 | 30 | 1.4771 | −0.3554 |
| | Day 16 | 14 | 1.1461 | −0.6864 |
| 3 | Day 0 | 53 | 1.7243 | |
| | Day 10 | 23 | 1.3617 | −0.3626 |
| | Day 16 | 15 | 1.1761 | −0.5482 |
| 4 | Day 0 | 55 | 1.7404 | |
| | Day 10 | 26 | 1.4150 | −0.3254 |
| | Day 16 | 11 | 1.0414 | −0.6990 |

The disclosures of all publications, patents, patent applications and published patent applications referred to herein by an identifying citation are hereby incorporated herein by reference in their entirety.

In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A pharmaceutical composition formulated for injection, comprising a pre-dilution formulation comprising:
   i. about 0.1 mg/mL of iloprost, or a pharmaceutically acceptable salt thereof or a stereoisomer thereof, relative to a total volume of the pre-dilution formulation;
   ii. about 0.24 mg/mL of tromethamine, relative to a total volume of the pre-dilution formulation;
   iii. sodium chloride; and
   iv. ethanol;
   wherein the pre-dilution formulation has a pH of about 8 to about 9; and
   wherein the pre-dilution formulation is diluted by about 100-fold prior to injection to form the composition for injection, said composition for injection being stable for up to 4 hours at 20° C. to 25° C.

2. The pharmaceutical composition of claim 1, wherein the composition for injection comprises about 1 µg/mL of iloprost, or a pharmaceutically acceptable salt or a stereoisomer thereof, relative to a total volume of the composition for injection.

3. The pharmaceutical composition of claim 2, wherein the composition for injection comprises about 1 mL of the pre-dilution formulation in about 100 mL of 0.9% sodium chloride.

4. The pharmaceutical composition of claim 3, wherein the composition for injection is for intravenous infusion.

5. A kit, comprising:
   the pre-dilution formulation of claim 1; and
   an IV bag comprising 0.9% sodium chloride for diluting the pre-dilution formulation.

6. The kit of claim 5, wherein the IV bag comprises about 100 ml of the 0.9% sodium chloride.

7. The kit of claim 5, wherein the IV bag is made of polyvinyl chloride (PVC).

8. The pharmaceutical composition of claim 1, wherein the pre-dilution formulation is provided as a single-use vial, and wherein each single use vial contains about 1 mL of the pre-dilution formulation.

9. The pharmaceutical composition of claim 1, wherein the pre-dilution formulation comprises about 0.242 mg/mL of tromethamine, relative to a total volume of the pre-dilution formulation.

10. The pharmaceutical composition of claim 1, wherein the pre-dilution formulation is formulated as a sterile solution.

11. The pharmaceutical composition of claim 1, wherein the pre-dilution formulation comprises no preservatives.

12. The pharmaceutical composition of claim 1, wherein the pre-dilution formulation comprises about 9.0 mg/mL of sodium chloride, relative to a total volume of the pre-dilution formulation.

* * * * *